(12) United States Patent
Kroemer et al.

(10) Patent No.: US 8,129,340 B2
(45) Date of Patent: Mar. 6, 2012

(54) INHIBITORS OF PROTEIN PHOSPHATASE 1, GADD34 AND PROTEIN PHOSPHATASE 1/GADD34 COMPLEX, PREPARATION AND USES THEREOF

(75) Inventors: Guido Kroemer, Antony (FR); Laurence Zitvogel, Antony (FR)

(73) Assignees: Institut Gustave Roussy, Villejuif Cedex (FR); Institut National de la Sante et de la Recherche Medicale (Inserm), Paris Cedex (FR)

( * ) Notice: Subject to any disclaimer, the term of this patent is extended or adjusted under 35 U.S.C. 154(b) by 214 days.

(21) Appl. No.: 12/438,833

(22) PCT Filed: Sep. 7, 2007

(86) PCT No.: PCT/EP2007/059409
§ 371 (c)(1),
(2), (4) Date: Feb. 25, 2009

(87) PCT Pub. No.: WO2008/028965
PCT Pub. Date: Mar. 13, 2008

(65) Prior Publication Data
US 2010/0016235 A1    Jan. 21, 2010

(30) Foreign Application Priority Data

Sep. 8, 2006 (EP) .................................. 06291427
Feb. 21, 2007 (EP) .................................. 07300806

(51) Int. Cl.
*A61K 31/675* (2006.01)
*A61K 38/10* (2006.01)
(52) U.S. Cl. .......................................... 514/7.6; 514/92
(58) Field of Classification Search .................. 514/7.6, 514/92
See application file for complete search history.

(56) References Cited

U.S. PATENT DOCUMENTS

2004/0142345 A1   7/2004   Ron et al.
2008/0214452 A1*  9/2008   Obeid ............................ 514/12

FOREIGN PATENT DOCUMENTS

| EP | 1 736 154 | 12/2006 |
|---|---|---|
| WO | WO 99/54447 | 10/1999 |
| WO | WO 2004/011595 | 2/2004 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Bruserud, O. et al. "Use of marine toxins in combination with cytotoxic drugs for induction of apoptosis in acute myelogenous leukaemia cells" *Expert Opin. Biol. Ther.*, 2002, pp. 197-210, vol. 2, No. 2, XP-008066422.
Connor, J. H. et al. "Growth Arrest and DNA Damage-Inducible Protein GADD34 Assembles a Novel Signaling Complex Containing Protein Phosphatase 1 and Inhibitor 1" *Molecular and Cellular Biology*, Oct. 2001, pp. 6841-6850, vol. 21, No. 20, XP-002439322.
Guergnon, J. et al. "Use of Penetrating Peptides Interacting with PP1/PP2A Proteins as a General Approach for a Drug Phosphatase Technology" *Molecular Pharmacology*, 2006, pp. 1115-1124, vol. 69, No. 4, XP-002439305.

* cited by examiner

*Primary Examiner* — Lynn Bristol
(74) *Attorney, Agent, or Firm* — Saliwanchik, Lloyd & Eisenschenk

(57) ABSTRACT

The present invention relates to the use of a protein phosphatase inhibitor selected from an inhibitor of the catalytic subunit of the protein phosphatase 1 (PP1), an inhibitor of GADD34 and an inhibitor of the PP1/GADD34 complex to prepare a pharmaceutical composition to prevent or treat a cancer in a mammal, wherein the pharmaceutical composition is intended for administration in combination with a product used in a treatment of a cancer.

10 Claims, 29 Drawing Sheets

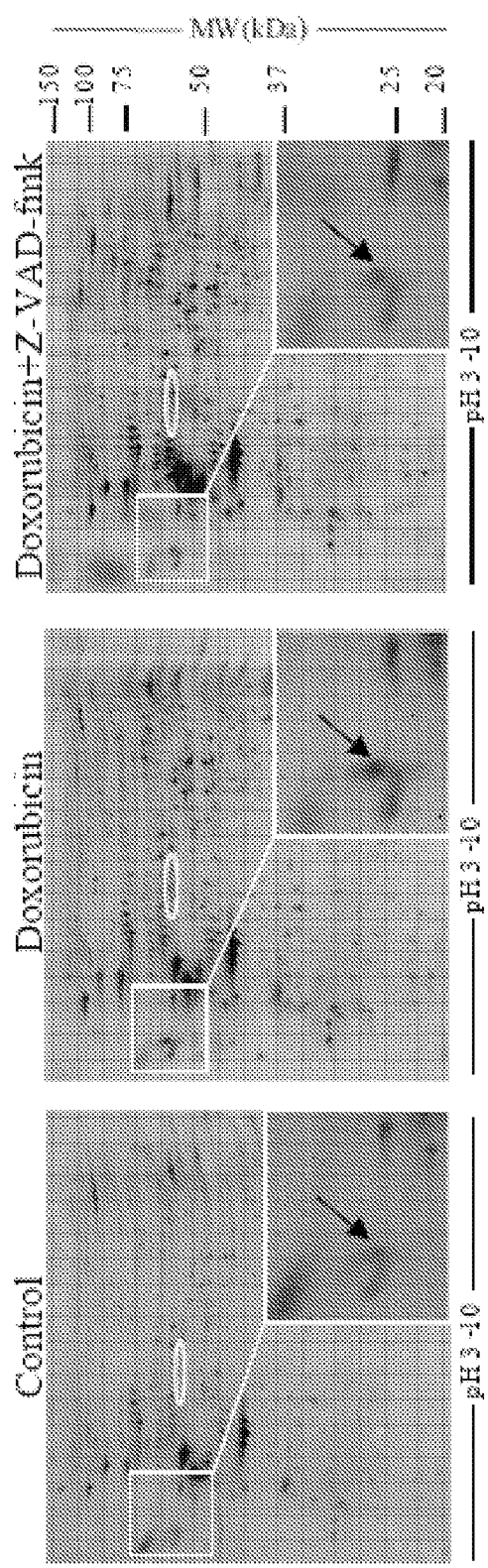
FIGURE 2A                    FIGURE 2B

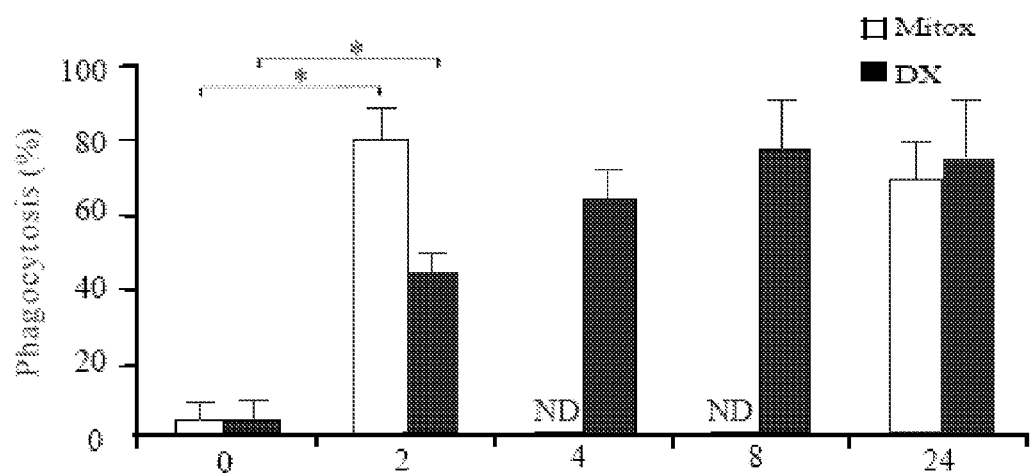
FIGURE 2SA
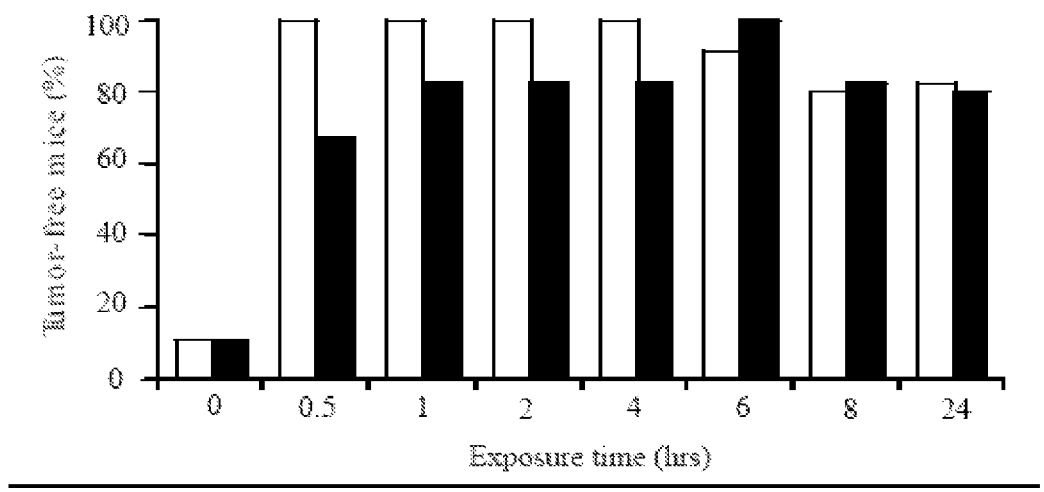
FIGURE 2S B

SEQUENCE LISTING

```
<160> NUMBER OF SEQ ID NOS: 19

<210> SEQ ID NO 1
<211> LENGTH: 674
<212> TYPE: PRT
<213> ORGANISM: Artificial
<220> FEATURE:
<223> OTHER INFORMATION: Human GADD34

<400> SEQUENCE: 1

Met Ala Pro Gly Gln Ala Pro His Gln Ala Thr Pro Trp Arg Asp Ala
1               5                   10                  15

His Pro Phe Phe Leu Leu Ser Pro Val Met Gly Leu Leu Ser Arg Ala
            20                  25                  30

Trp Ser Arg Leu Arg Gly Leu Gly Pro Leu Glu Pro Trp Leu Val Glu
        35                  40                  45

Ala Val Lys Gly Ala Ala Leu Val Glu Ala Gly Leu Glu Gly Glu Ala
    50                  55                  60

Arg Thr Pro Leu Ala Ile Pro His Thr Pro Trp Gly Arg Arg Pro Gly
65                  70                  75                  80

Glu Glu Ala Glu Asp Ser Gly Gly Pro Gly Glu Asp Arg Glu Thr Leu
                85                  90                  95

Gly Leu Lys Thr Ser Ser Ser Leu Pro Glu Ala Trp Gly Leu Leu Asp
            100                 105                 110

Asp Asp Asp Gly Met Tyr Gly Glu Arg Glu Ala Thr Ser Val Pro Arg
        115                 120                 125

Gly Gln Gly Ser Gln Phe Ala Asp Gly Gln Arg Ala Pro Leu Ser Pro
    130                 135                 140

Ser Leu Leu Ile Arg Thr Leu Gln Gly Ser Asp Lys Asn Pro Gly Glu
145                 150                 155                 160

Glu Lys Ala Glu Glu Gly Val Ala Glu Glu Gly Val Asn Lys
                165                 170                 175

Phe Ser Tyr Pro Pro Ser His Arg Glu Cys Cys Pro Ala Val Glu Glu
            180                 185                 190

Glu Asp Asp Glu Glu Ala Val Lys Lys Glu Ala His Arg Thr Ser Thr
        195                 200                 205

Ser Ala Leu Ser Pro Gly Ser Lys Pro Ser Thr Trp Val Ser Cys Pro
    210                 215                 220

Gly Glu Glu Glu Asn Gln Ala Thr Glu Asp Lys Arg Thr Glu Arg Ser
225                 230                 235                 240

Lys Gly Ala Arg Lys Thr Ser Val Ser Pro Arg Ser Ser Gly Ser Asp
                245                 250                 255

Pro Arg Ser Trp Glu Tyr Arg Ser Gly Glu Ala Ser Glu Glu Lys Glu
```

-continued

```
                260                 265                 270
Glu Lys Ala His Glu Thr Gly Lys Gly Glu Ala Pro Gly Pro
            275                 280                 285

Gln Ser Ser Ala Pro Ala Gln Arg Pro Gln Leu Lys Ser Trp Trp Cys
            290                 295                 300

Gln Pro Ser Asp Glu Glu Ser Glu Val Lys Pro Leu Gly Ala Ala
305                 310                 315                 320

Glu Lys Asp Gly Glu Ala Glu Cys Pro Pro Cys Ile Pro Pro Ser
                325                 330                 335

Ala Phe Leu Lys Ala Trp Val Tyr Trp Pro Gly Glu Asp Thr Glu Glu
            340                 345                 350

Glu Glu Asp Glu Glu Glu Asp Glu Asp Ser Asp Ser Gly Ser Asp Glu
            355                 360                 365

Glu Glu Gly Glu Ala Glu Ala Ser Ser Ser Thr Pro Ala Thr Gly Val
            370                 375                 380

Phe Leu Lys Ser Trp Val Tyr Gln Pro Gly Glu Asp Thr Glu Glu Glu
385                 390                 395                 400

Glu Asp Glu Asp Ser Asp Thr Gly Ser Ala Glu Asp Glu Arg Glu Ala
                405                 410                 415

Glu Thr Ser Ala Ser Thr Pro Pro Ala Ser Ala Phe Leu Lys Ala Trp
            420                 425                 430

Val Tyr Arg Pro Gly Glu Asp Thr Glu Glu Glu Asp Glu Asp Val
            435                 440                 445

Asp Ser Glu Asp Lys Glu Asp Ser Glu Ala Ala Leu Gly Glu Ala
            450                 455                 460

Glu Ser Asp Pro His Pro Ser His Pro Asp Gln Ser Ala His Phe Arg
465                 470                 475                 480

Gly Trp Gly Tyr Arg Pro Gly Lys Glu Thr Glu Glu Glu Ala Ala
                485                 490                 495

Glu Asp Trp Gly Glu Ala Glu Pro Cys Pro Phe Arg Val Ala Ile Tyr
            500                 505                 510

Val Pro Gly Glu Lys Pro Pro Pro Trp Ala Pro Pro Arg Leu Pro
            515                 520                 525

Leu Arg Leu Gln Arg Arg Leu Lys Arg Pro Glu Thr Pro Thr His Asp
            530                 535                 540

Pro Asp Pro Glu Thr Pro Leu Lys Ala Arg Lys Val Arg Phe Ser Glu
545                 550                 555                 560

Lys Val Thr Val His Phe Leu Ala Val Trp Ala Gly Pro Ala Gln Ala
                565                 570                 575

Ala Arg Gln Gly Pro Trp Glu Gln Leu Ala Arg Asp Arg Ser Arg Phe
            580                 585                 590

Ala Arg Arg Ile Ala Gln Ala Gln Glu Glu Leu Ser Pro Cys Leu Thr
            595                 600                 605

Pro Ala Ala Arg Ala Arg Ala Trp Ala Arg Leu Arg Asn Pro Pro Leu
            610                 615                 620

Ala Pro Ile Pro Ala Leu Thr Gln Thr Leu Pro Ser Ser Ser Val Pro
625                 630                 635                 640

Ser Ser Pro Val Gln Thr Thr Pro Leu Ser Gln Ala Val Ala Thr Pro
                645                 650                 655

Ser Arg Ser Ser Ala Ala Ala Ala Ala Leu Asp Leu Ser Gly Arg
            660                 665                 670

Arg Gly
```

```
<210> SEQ ID NO 2
<211> LENGTH: 12
<212> TYPE: PRT
<213> ORGANISM: artificial
<220> FEATURE:
<223> OTHER INFORMATION: Fragment of GADD34

<400> SEQUENCE: 2

Leu Lys Ala Arg Lys Val Arg Phe Ser Glu Lys Val
1               5                   10

<210> SEQ ID NO 3
<211> LENGTH: 12
<212> TYPE: PRT
<213> ORGANISM: artificial
<220> FEATURE:
<223> OTHER INFORMATION: N-terminal DPT-sh1 sequence

<400> SEQUENCE: 3

Val Lys Lys Lys Lys Ile Lys Arg Glu Ile Lys Ile
1               5                   10

<210> SEQ ID NO 4
<211> LENGTH: 24
<212> TYPE: PRT
<213> ORGANISM: artificial
<220> FEATURE:
<223> OTHER INFORMATION: Artificial sequence including a fragment of
      GADD34 and a translocation motif.

<400> SEQUENCE: 4

Val Lys Lys Lys Lys Ile Lys Arg Glu Ile Lys Ile Leu Lys Ala Arg
1               5                   10                  15

Lys Val Arg Phe Ser Glu Lys Val
            20

<210> SEQ ID NO 5
<211> LENGTH: 21
<212> TYPE: DNA
<213> ORGANISM: artificial
<220> FEATURE:
<223> OTHER INFORMATION: Sense siRNA specific for human Bax.

<400> SEQUENCE: 5
ggugccggaa cugaucagat t                                             21

<210> SEQ ID NO 6
<211> LENGTH: 21
<212> TYPE: DNA
<213> ORGANISM: artificial
<220> FEATURE:
<223> OTHER INFORMATION: Anti-sense siRNA specific for human Bax.

<400> SEQUENCE: 6
ucugaucagu uccggcacct t                                             21

<210> SEQ ID NO 7
<211> LENGTH: 23
<212> TYPE: DNA
<213> ORGANISM: artificial
<220> FEATURE:
<223> OTHER INFORMATION: Sense siRNA specific for Bak.

<400> SEQUENCE: 7
accgacgcka tgactcagag ttc                                           23

<210> SEQ ID NO 8
```

-continued

<211> LENGTH: 18
<212> TYPE: DNA
<213> ORGANISM: artificial
<220> FEATURE:
<223> OTHER INFORMATION: Anti-sense siRNA specific for Bak.

<400> SEQUENCE: 8
acacggcacc aattgatg 18

<210> SEQ ID NO 9
<211> LENGTH: 19
<212> TYPE: DNA
<213> ORGANISM: artificial
<220> FEATURE:
<223> OTHER INFORMATION: Sense siRNA control sequence.

<400> SEQUENCE: 9
gccgguaugc cgguuaagu 19

<210> SEQ ID NO 10
<211> LENGTH: 19
<212> TYPE: DNA
<213> ORGANISM: artificial
<220> FEATURE:
<223> OTHER INFORMATION: Anti-sense siRNA control sequence.

<400> SEQUENCE: 10
acuuaaccgg cauaccggc 19

<210> SEQ ID NO 11
<211> LENGTH: 35
<212> TYPE: DNA
<213> ORGANISM: artificial
<220> FEATURE:
<223> OTHER INFORMATION: Sense siRNA specific for CRT.

<400> SEQUENCE: 11
rcrcrgrcur grgrgurcrg raraurcrrr aratt 35

<210> SEQ ID NO 12
<211> LENGTH: 38
<212> TYPE: DNA
<213> ORGANISM: artificial
<220> FEATURE:
<223> OTHER INFORMATION: siRNA specific for GADD34.

<400> SEQUENCE: 12
rcrargrgra rgrcrargra urcrargrau rargratt 38

<210> SEQ ID NO 13
<211> LENGTH: 36
<212> TYPE: DNA
<213> ORGANISM: artificial
<220> FEATURE:
<223> OTHER INFORMATION: siRNA specific for PPICalpha.

<400> SEQUENCE: 13
rgrcurgrgr crcuraurar argraurcra rgratt 36

<210> SEQ ID NO 14
<211> LENGTH: 35
<212> TYPE: DNA
<213> ORGANISM: artificial
<220> FEATURE:
<223> OTHER INFORMATION: siRNA control.

<400> SEQUENCE: 14
rgrcrcrgrg uraurgrcrc rgrguurara rgutt    35

<210> SEQ ID NO 15
<211> LENGTH: 416
<212> TYPE: PRT
<213> ORGANISM: artificial
<220> FEATURE:
<223> OTHER INFORMATION: CRT protein sequence.

<400> SEQUENCE: 15

```
Met Leu Leu Ser Val Pro Leu Leu Gly Leu Leu Gly Leu Ala Ala
1               5                   10                  15

Ala Asp Pro Ala Ile Tyr Phe Lys Glu Gln Phe Leu Asp Gly Asp Ala
            20                  25                  30

Trp Thr Asn Arg Trp Val Glu Ser Lys His Lys Ser Asp Phe Gly Lys
        35                  40                  45

Phe Val Leu Ser Ser Gly Lys Phe Tyr Gly Asp Leu Glu Lys Asp Lys
    50                  55                  60

Gly Leu Gln Thr Ser Gln Asp Ala Arg Phe Tyr Ala Leu Ser Ala Lys
65                  70                  75                  80

Phe Glu Pro Phe Ser Asn Lys Gly Gly Thr Leu Val Val Gln Phe Thr
            85                  90                  95

Val Lys His Glu Lys Asn Ile Asp Cys Gly Gly Gly Tyr Val Lys Leu
        100                 105                 110

Phe Pro Ser Gly Leu Asp Gln Lys Asp Met His Gly Asp Ser Glu Tyr
    115                 120                 125

Asn Ile Met Phe Gly Pro Asp Ile Cys Gly Pro Gln Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
            165                 170                 175

Arg Pro Asp Asn Thr Tyr Glu Val Lys Ile Asp Asn Ser Gln Val Glu
        180                 185                 190

Ser Gly Ser Leu Glu Asp Asp Trp Asp Phe Leu Pro Pro Lys Lys Ile
    195                 200                 205

Lys Asp Pro Asp Ala Ala Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
            245                 250                 255

Met Asp Gly Glu Trp Glu Pro Pro Val Ile Gln Asn Pro Glu Tyr Lys
        260                 265                 270

Gly Glu Trp Lys Pro Arg Gln Ile Asp Asn Pro Asp Tyr Lys Gly Thr
    275                 280                 285

Trp Ile His Pro Glu Ile Asp Asn Pro Glu Tyr Ser Pro Asp Ala Asn
290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
            325                 330                 335

Ala Tyr Ala Glu Glu Phe Gly Asn Glu Thr Trp Gly Val Thr Lys Ala
        340                 345                 350

Ala Glu Lys Gln Met Lys Asp Lys Gln Asp Glu Glu Gln Arg Leu Lys
    355                 360                 365
```

```
Glu Glu Glu Glu Asp Lys Lys Arg Lys Glu Glu Glu Ala Glu Asp
        370                 375                 380

Lys Glu Asp Asp Asp Arg Asp Glu Asp Glu Asp Glu Glu Asp Glu
385                 390                 395                 400

Lys Glu Glu Asp Glu Glu Glu Ser Pro Gly Gln Ala Lys Asp Glu Leu
                405                 410                 415

<210> SEQ ID NO 16
<211> LENGTH: 4
<212> TYPE: PRT
<213> ORGANISM: Artificial sequence
<220> FEATURE:
<223> OTHER INFORMATION: retention sequence

<400> SEQUENCE: 16

Lys Asp Glu Leu
1

<210> SEQ ID NO 17
<211> LENGTH: 24
<212> TYPE: PRT
<213> ORGANISM: Artificial sequence
<220> FEATURE:
<223> OTHER INFORMATION: Artificial sequence including a fragment of
      GADD34 and a translocation motif

<400> SEQUENCE: 17

Val Lys Lys Lys Lys Ile Lys Arg Glu Ile Lys Ile Leu Lys Ala Arg
1               5                   10                  15

Ala Val Ala Phe Ser Glu Lys Val
            20

<210> SEQ ID NO 18
<211> LENGTH: 24
<212> TYPE: PRT
<213> ORGANISM: Artificial sequence
<220> FEATURE:
<223> OTHER INFORMATION: Artificial sequence including a fragment of
      GADD34 and a translocation motif

<400> SEQUENCE: 18

Val Lys Lys Lys Lys Ile Lys Arg Glu Ile Lys Ile Leu Lys Ala Arg
1               5                   10                  15

Ala Val Arg Phe Ser Glu Lys Val
            20

<210> SEQ ID NO 19
<211> LENGTH: 416
<212> TYPE: PRT
<213> ORGANISM: Artificial sequence
<220> FEATURE:
<223> OTHER INFORMATION: CRT protein sequence

<400> SEQUENCE: 19

Met Leu Leu Ser Val Pro Leu Leu Gly Leu Leu Gly Leu Ala Ala
1               5                   10                  15

Ala Asp Pro Ala Ile Tyr Phe Lys Glu Gln Phe Leu Asp Gly Asp Ala
                20                  25                  30

Trp Thr Asn Arg Trp Val Glu Ser Lys His Lys Ser Asp Phe Gly Lys
            35                  40                  45

Phe Val Leu Ser Ser Gly Lys Phe Tyr Gly Asp Leu Glu Lys Asp Lys
        50                  55                  60

Gly Leu Gln Thr Ser Gln Asp Ala Arg Phe Tyr Ala Leu Ser Ala Lys
```

|   |   |   |   |   |   |   |   |   |   |   |   |   |   |   |
|---|---|---|---|---|---|---|---|---|---|---|---|---|---|---|
| | | | | 65 | | | | 70 | | | | 75 | | 80 |
| Phe | Glu | Pro | Phe | Ser | Asn | Lys | Gly | Gln | Thr | Leu | Val | Val | Gln | Phe | Thr |
| | | | | 85 | | | | 90 | | | | 95 | | |
| Val | Lys | His | Glu | Gln | Asn | Ile | Asp | Cys | Gly | Gly | Gly | Tyr | Val | Lys | Leu |
| | | | 100 | | | | 105 | | | | 110 | | | |
| Phe | Pro | Ser | Gly | Leu | Asp | Gln | Lys | Asp | Met | His | Gly | Asp | Ser | Glu | Tyr |
| | | 115 | | | | 120 | | | | 125 | | | | |
| Asn | Ile | Met | Phe | Gly | Pro | Asp | Ile | Cys | Gly | Pro | Gly | Thr | Lys | Lys | Val |
| | 130 | | | | 135 | | | | 140 | | | | | |
| His | Val | Ile | Phe | Asn | Tyr | Lys | Gly | Lys | Asn | Val | Leu | Ile | Asn | Lys | Asp |
| 145 | | | | 150 | | | | 155 | | | | 160 | | | |
| Ile | Arg | Cys | Lys | Asp | Asp | Glu | Phe | Thr | His | Leu | Tyr | Thr | Leu | Ile | Val |
| | | | 165 | | | | 170 | | | | 175 | | | | |
| Arg | Pro | Asp | Asn | Thr | Tyr | Glu | Val | Lys | Ile | Asp | Asn | Ser | Gln | Val | Glu |
| | | 180 | | | | 185 | | | | 190 | | | | | |
| Ser | Gly | Ser | Leu | Glu | Asp | Asp | Trp | Asp | Phe | Leu | Pro | Pro | Lys | Lys | Ile |
| | 195 | | | | 200 | | | | 205 | | | | | | |
| Lys | Asp | Pro | Asp | Ala | Ala | Lys | Pro | Glu | Asp | Trp | Asp | Glu | Arg | Ala | Lys |
| 210 | | | | 215 | | | | 220 | | | | | | | |
| Ile | Asp | Asp | Pro | Thr | Asp | Ser | Lys | Pro | Glu | Asp | Trp | Asp | Lys | Pro | Glu |
| 225 | | | 230 | | | | 235 | | | | 240 | | | | |
| His | Ile | Pro | Asp | Pro | Asp | Ala | Lys | Lys | Pro | Glu | Asp | Trp | Asp | Glu | Glu |
| | | 245 | | | | 250 | | | | 255 | | | | | |
| Met | Asp | Gly | Glu | Trp | Glu | Pro | Pro | Val | Ile | Gln | Asn | Pro | Glu | Tyr | Lys |
| | 260 | | | | 265 | | | | 270 | | | | | | |
| Gly | Glu | Trp | Lys | Pro | Arg | Gln | Ile | Asp | Asn | Pro | Asp | Tyr | Lys | Gly | Thr |
| | 275 | | | | 280 | | | | 285 | | | | | | |
| Trp | Ile | His | Pro | Glu | Ile | Asp | Asn | Pro | Glu | Tyr | Ser | Pro | Asp | Ala | Asn |
| 290 | | | | 295 | | | | 300 | | | | | | | |
| Ile | Tyr | Ala | Tyr | Asp | Ser | Phe | Ala | Val | Leu | Gly | Leu | Asp | Leu | Trp | Gln |
| 305 | | | 310 | | | | 315 | | | | 320 | | | | |
| Val | Lys | Ser | Gly | Thr | Ile | Phe | Asp | Asn | Phe | Leu | Ile | Thr | Asn | Asp | Glu |
| | | | 325 | | | | 330 | | | | 335 | | | | |
| Ala | Tyr | Ala | Glu | Glu | Phe | Gly | Asn | Glu | Thr | Trp | Gly | Val | Thr | Lys | Ala |
| | | | 340 | | | | 345 | | | | 350 | | | | |
| Ala | Glu | Lys | Gln | Met | Lys | Asp | Lys | Gln | Asp | Glu | Glu | Arg | Leu | Lys |
| | | 355 | | | | 360 | | | | 365 | | | | | |
| Glu | Glu | Glu | Glu | Asp | Lys | Lys | Arg | Lys | Glu | Glu | Glu | Ala | Glu | Asp |
| 370 | | | | 375 | | | | 380 | | | | | | | |
| Lys | Glu | Asp | Asp | Asp | Asp | Arg | Asp | Glu | Asp | Glu | Asp | Glu | Glu | Asp | Glu |
| 385 | | | | 390 | | | | 395 | | | | 400 | | | |
| Lys | Glu | Glu | Asp | Glu | Glu | Ser | Pro | Gly | Gln | Ala | Lys | Asp | Glu | Leu |
| | | | 405 | | | | 410 | | | | 415 | | | | |

INHIBITORS OF PROTEIN PHOSPHATASE 1, GADD34 AND PROTEIN PHOSPHATASE 1/GADD34 COMPLEX, PREPARATION AND USES THEREOF

CROSS-REFERENCE TO RELATED APPLICATION

This application is the U.S. national stage application of International Patent Application No. PCT/EP2007/059409, filed Sept. 7, 2007, the disclosure of which is hereby incorporated by reference in its entirety, including all figures, tables and amino acid or nucleic acid sequences.

DOMAIN OF THE INVENTION

The present invention relates to isolated and purified proteins, such as calreticulin (CRT), KDEL receptor and ERp57, as well as to any compound that allows or enhances CRT, KDEL receptor and/or ERp57 exposure at the surface of a dying cell and thus induces a reaction from the immune system. Inventors have in particular discovered that said proteins and compounds can be used in combination with a cytotoxic compound or an apoptosis inducer to prepare a pharmaceutical composition to prevent or treat a cancer or an infection in a mammal, in particular to improve the efficiency of a therapy, preferably a therapy of cancer, in a mammal in need thereof.

The present invention further provides kits, methods for detecting CRT, KDEL receptor, and/or ERp57 exposure at the surface of a cell, methods for selecting a compound of interest, as well as pharmaceutical compositions.

BACKGROUND OF THE INVENTION

Cancer is the major cause of mortality in most industrialized countries. Different ways of cancer treatment can be used: surgery, radiotherapy, immunotherapy, hormonotherapy and chemotherapy. Numerous research laboratories lead works to find cancer therapy improvements. Chemotherapy leads to the cell death. Two type of cell death are known: the apoptosis and the necrosis.

It has long been hypothesized that apoptotic cell death would be poorly immunogenic (or even tolerogenic) whereas necrotic cell death would be truly immunogenic (Bellamy, C. O., Malcomson, R. D., Harrison, D. J. & Wyllie, A. H. *Semin Cancer Biol* 6, 3-16 (1995); Thompson, C. B. *Science* 267, 1456-1462 (1995); Igney, F. H. & Krammer, P. H. *Nat Rev Cancer.* 2, 277-88 (2002)).

This difference was thought to result from the intrinsic capacity of cells dying from non-apoptotic cell death to stimulate the immune response, for example by stimulating local inflammatory responses ('danger signals') and/or by triggering the maturation of dendritic cells (DCs) (Steinman, R. M., Turley, S., Mellman, I. & Inaba, K. *J Exp Med.* 191, 411-6 (2000); Liu, K. et al. *J Exp Med* 196, 1091-1097. (2002).

In contrast to necrosis (which is defined by brisk plasma membrane rupture), apoptosis is associated with a series of subtle alterations in the plasma membrane that render the dying cells palatable to phagocytic cells (Kroemer, G. et al. *Cell Death Differ* 12, 1463-1467 (2005)). Such "eat me" signals, which include the adsorption of soluble proteins from outside the cell (such as C1q and thrombospondin) and the translocation of molecules from inside the cell to the surface (such as phosphatidylserine, PS, and calreticulin, CRT), as well as the suppression of "don't eat me" signals (such as CD47) (Savill, J. & Fadok, V. *Nature* 407, 784-(2000); Lauber, K., Blumenthal, S. G., Waibel, M. & Wesselborg, S. *Mol Cell.* 14, 277-87 (2004); Yoshida, H. et al. *Nature* 437, 754-8 (2005); Gardai, S. J. et al. *Cell* 123, 321-34 (2005); Henson, P. M. & Hume, D. A. *Trends Immunol* 27, 244-50 (2006)) elicit the recognition and removal of apoptotic cells by professional and non-professional phagocytes. Suboptimal clearance of apoptotic cells can trigger unwarranted immune reactions and lead to autoimmune disease (Hanayama, R. et al. *Science* 3004, 1147-50. (2004); Gaipl, U. S. et al. *Curr Top Microbiol Immunol* 305, 161-76 (2006)).

Nonetheless, it seems that the dichotomy between immunogenic necrosis versus tolerogenic apoptosis is an oversimplification. Thus, unscheduled (necrotic) tumour cell death may induce local immunosuppression (Vakkila, J. & Lotze, M. T *Nat Rev Immunol* 4, 641-8 (2004)). Moreover, the capacity of apoptotic tumour cells to trigger the immune response was found to depend on the apoptosis inducer, leading to the identification of two morphologically undistinguishable subcategories of apoptosis, namely immunogenic versus non-immunogenic apoptosis (Casares, N. et al. *J. Exp. Med.* 202, 1691-701 (2005); Blachere, N. E., Darnell, R. B. & Albert, M. L. *PLoS Biol.* 3, e185 (2005)).

Most of standard chemotherapies induce a non-immunogenic apoptosis (Zitvogel, L., Casares, N., Pequignot, M., Albert, M. L. & Kroemer, G. *Adv. Immunol.* 84, 131-79 (2004); Steinman, R. M. & Mellman, I. *Science* 305, 197-200 (2004); Lake, R. A. & van der Most, R. G. *N Engl J Med* 354, 2503-4 (2006)). Thus, even after an initially efficient chemotherapy, patients do not develop an efficient antitumourous immune response and then are overcome by chemotherapy-resistant tumourous variants. To improve anticancer chemotherapy, a promising way is brought by the immunogenic cancer-cell death. Indeed, induction of immunogenic cancer-cell death should be very interesting in that the immune system can contribute through a "bystander effect" to eradicate chemotherapy-resistant cancer cells and cancer stem cells (Steinman, R. M. & Mellman, I. *Science* 305, 197-200 (2004); Lake, R. A. & van der Most, R. G. *N Engl J Med* 354, 2503-4 (2006); Zitvogel, L., Tesniere, A. & Kroemer, G. *Nat Rev Immunol* in press (2006)).

The efficiency of chemotherapy and the responsiveness is linked to the drugs used and to the molecules involved in the chemotherapy. The main drugs used in anti-tumourous chemotherapy can be divided in four groups: cytotoxic agents, hormones, immune response modulators, and inhibitors of the tyrosine kinase activity. Among cytotoxic agents, one can find cytotoxic antibiotics such as anthracyclins (doxorubicin, idarubicin, mitoxantrone which are apoptosis inducers). Inventors have shown for the first time that anthracyclins are capable of eliciting immunogenic apoptosis (Casares, N., Pequignot, M. O., Tesniere, A., Ghiringhelli, F., Roux, S., Chaput, N., Schmitt, E., Hamai, A., Hervas-Stubbs, S., Obeid, M., Coutant, F., Métivier, D., Pichard, E., Aucouturier, P., Pierron, G., Garrido, C., Zitvogel, L., and Kroemer, G. *J Exp Med.* 202, 1691-701 (2005)). Indeed, while most apoptosis inducers, including agents that target the endoplasmic reticulum (ER) (thapsigargin, tunicamycin, brefeldin), mitochondria (arsenite, betulinic acid, C2 ceramide) or DNA (Hoechst 33343, camptothecin, etoposide, mitomycin C), failed to induce immunogenic apoptosis, anthracyclins elicited immunogenic cell death (as shown in FIGS. 1B,C). Despite a growing body of research, under which circumstances an immune response is triggered against dying tumour cells remains an open question (Zitvogel, L., Casares, N., Pequignot, M., Albert, M. L. & Kroemer, G. *Adv. Immunol.* 84, 131-79 (2004)).

The present invention is based on the observation that the proteins named calreticulin (CRT), KDEL receptor (KDEL receptor is a CRT receptor) and ERp57 are exposed on cells that succumb to immunogenic cell death, yet lacks on the surface of cells that undergo non-immunogenic cell death.

CRT has been already described for modulating the hormonal response, another way to treat cancer. Proteins which modulate hormone receptor induced gene transcription are present in the nucleus of the cell and inhibit or promote the binding of a hormone to its receptor. The invention described in the patent US 2003/0060613 A1 presents a purified protein, efficient in anti-cancer therapy, which is used to modulate hormone responsiveness. US 2003/0060613 A1 describes CRT as a synthetic protein, a mimetic protein thereof, a DNA molecule encoding CRT, a method of treating a disease such as cancer, and a kit containing a pharmaceutical comprising one of said proteins. CRT is described to be present either in the endoplasmic reticulum or in the nucleus of a cell. This patent application describes mechanism of action of nuclear CRT on gene transcription.

ERp57 is a lumenal protein of the endoplasmic reticulum (ER) and a member of the protein disulfide isomerase (PDI) family. In contrast to archetypal PDI, ERp57 is known to interact specifically with newly synthesized glycoproteins including CRT. Oliver et al. (MBC online, Vol. 10, Issue 8, 2573-2582, August 1999) indicates that ERp57 interacts with calnexin and CRT within the ER lumen to modulate glycoprotein folding.

The majority of endoplasmic reticulum resident proteins are retained in the endoplasmic reticulum (ER) through a retention motif. This motif is composed of four amino acids at the end of the protein sequence. The most common retention sequence is KDEL (Lys-Asp-Glu-Leu) (SEQ ID NO:16). There are three KDEL receptors in mammalian cells, and they have a very high degree of sequence identity. The KDEL receptor (KDEL-R) is usually present within the ER. Inventors have shown that KDEL receptor can also interact with the KDEL motif of CRT.

The inventors have more particularly identified a particular alteration in the plasma membrane of dying cells: the surface exposure of calreticulin (CRT), KDEL receptor and/or ERp57, This event only occurs in immunogenic cancer cell death, i.e., in cancer cell death implying a reaction of the immune system. In immunogenic cancer cell death, the immune system thus participates to the dying cells elimination in addition to the other physiological cell destruction mechanisms. Exogenous CRT, KDEL receptor and/or ERp57, or external provision of signals that induces CRT, KDEL receptor and/or ERp57 exposure, confers immunogenicity to otherwise non-immunogenic cell death, i.e., mobilize and activate the immune system, to allow an optimal anti-cancer chemotherapy.

DETAILED DESCRIPTION OF THE INVENTION

"Immunogenic Cell Death"

The present invention is based on the identification of CRT, KDEL receptor and/or ERp57 exposure(s) as essential to induce a response from the immune system directed against dying cells and delineate a new strategy to prevent or treat a disease, such as a cancer or an infection.

The response from the immune system is herein called an "anti-cancer immune response" when it is directed against tumour cells.

The new treatment strategy is further herein called "immunogenic treatment of cancer", when it is directed against a cancer.

CRT and/or ERp57 are able to induce a response from the immune system directed against any dying cells, when at least one of them is exposed on their surface. This response from the immune system favours the destruction of the dying cells. This phenomenon is called an "immunogenic cell death" or "immunogenic apoptosis".

Inventors thus herein demonstrate that when CRT is exposed on the surface of dying cells, it promotes their destruction by phagocytes such as dendritic cells. Phagocytes then interact with the immune system which is in turn responsible for the immune response.

Inventors further demonstrate that this effect is amplified when CRT is present in an increased amount on the surface of dying cells. They herein demonstrate that CRT is present in an increased amount on the surface of most tumour cells that have been contacted with a cell death inducer (apoptosis inducer).

Inventors have further discovered that the kinetics of CRT, KDEL receptor (CRT receptor) and ERp57 cell surface exposures are identical and that all three proteins are induced by the same pattern of stimuli.

Double immunofluorescence stainings indeed reveal that CRT, KDEL receptor and ERp57 largely co-immunolocalize when they appear together on the surface o MTX-treated cells (FIG. 8 and FIG. 10). Inventors found that mouse embryonic fibroblasts (MEF) lacking CRT fail to expose ERp57 on the surface after MTX treatment. Conversely, MEF lacking ERp57 failed to expose ecto-CRT on the surface after MTX treatment (not shown). Altogether, these results indicate that ERp57 and CRT translocate together to the cell surface and that the determination of ERp57 surface exposure by immunological techniques accurately reflects the surface exposure of CRT (ecto-CRT). Accordingly, inventors found for instance that treatment with tautomycin, which also induces ecto-CRT exposure (Obeid et al. Nat. Med. 2007) also stimulates the surface exposure or ERp57, as determined by immunofluorescence staining followed by cytofluorometric analysis (FIG. 9).

The location or exposure of CRT, KDEL receptor and/or ERp57 at the cellular surface could be the result of the translocation of intracellular CRT, intracellular KDEL receptor and/or intracellular ERp57 to the cell surface and/or the result of the translocation of extracellular CRT, extracellular KDEL receptor and/or extracellular ERp57 to the cell surface.

Inventors also herein demonstrate that both CRT and ERp57 can confer immunogenic properties to the apoptosis phenomenon. KDEL receptor also can confer immunogenic properties to the apoptosis phenomenon.

In the present invention, CRT may be a recombinant CRT, an endogenous CRT or a mimetic or a homologous variant thereof.

In the present invention, ERp57 may be a recombinant ERp57, an endogenous ERp57 or a mimetic or a homologous variant thereof.

In the present invention, KDEL receptor may be a recombinant KDEL receptor, an endogenous KDEL receptor or a mimetic or a homologous variant thereof.

In the present invention, the term "endogenous" means that CRT, KDEL receptor and ERp57 are produced by the cell respectively as wild-type CRT, KDEL receptor and wild-type ERp57. The wild-type proteins have to be distinguished from the recombinant CRT (rCRT), KDEL receptor (rKDEL receptor) and ERp57 (rERp57) whose activities, in particular regarding the immune system, are respectively substantially identical to that of the previously mentioned wild-type proteins but which need a human intervention to be produced by the cell.

In the present invention, the term "homologous variant" is used to designate any CRT, KDEL receptor or ERp57 protein that comprises deleted or substituted amino acid(s), for example any wild-type or recombinant CRT, KDEL receptor or ERp57 protein fragment that exhibits the properties of the corresponding wild-type protein, in particular that is able to induce a response from the immune system, for example an immunogenic cell death or apoptosis as previously defined.

In a particular embodiment of the present invention, CRT, KDEL receptor and/or ERp57 can be used to prevent or treat an infection, preferably selected from a viral, a bacterial, a fungal and a parasitic infection.

In another particular embodiment of the present invention, CRT, KDEL receptor and/or ERp57 can be used to prevent or treat any kind of cancer or neoplasia.

In the present invention, the targeted cancer is preferably a cancer that is sensitive to one of the following therapies: (i) a chemotherapy, (ii) a radiotherapy, (iii) a hormonotherapy, (iv) an immunotherapy, (v) a specific kinase inhibitor-based therapy, (vi) an antiangiogenic agent based-therapy, and (vii) an antibody-based therapy, preferably a monoclonal antibody-based therapy.

Cancers sensitive to chemotherapy are conventionally treated using a compound such as any cytotoxic agent or cell death inducer, in particular a genotoxic agent. In a particular embodiment of the present invention, the cytotoxic agent is a chemotherapeutic agent, preferably selected for example from an anthracyclin, an antimitotic agent, a DNA intercalating agent, a taxane, gemcitabine, etoposide, mitomycine C, an alkylating agent, a platin based component such as cis-platinum and preferably oxaliplatinum and a TLR-3 ligand.

A preferred anthracyclin may be selected for example from doxorubicin, daunorubicin, idarubicin and mitoxantrone.

Cancers sensitive to radiotherapy are conventionally treated using an irradiation selected for example from X-rays, gamma irradiation and/or UVC irradiation.

Cancers sensitive to a hormonotherapy, i.e., to a therapy leading to apoptosis or Fas ligands or soluble /membrane bound TRAIL or soluble/membrane bound TNF alpha (TNFa), are conventionally treated using a compound such as an antiaromatase for example.

Cancers sensitive to an immunotherapy are conventionally treated using a compound selected for example from IL-2, IFN alpha (IFNa), and a vaccine.

Cancers sensitive to a specific kinase inhibitor-based therapy are conventionally treated using a compound selected for example from a tyrosine kinase inhibitor, a serine kinase inhibitor and a threonine kinase inhibitor.

Cancers sensitive to an antibody-based therapy, preferably to a monoclonal antibody-based therapy, are conventionally treated using a specific antibody such as for example anti-CD20 or anti-Her2/Neu.

The term "conventionally" means that the therapy is applied or, if not routinely applied, is appropriate and at least recommended by health authorities. The "conventional" treatment is selected by the cancerologist depending on the specific cancer to be prevented or treated.

In the present invention, the targeted cancer can thus for example be a cancer that is sensitive to at least one of the above mentioned therapeutic product, in particular to at least one of the following product: (i) a cytotoxic agent, (ii) a kinase inhibitor, (iii) an anti-angiogenic agent, (vi) a monoclonal antibody.

The cancer is, in the present invention, preferably selected from a breast cancer, a prostate cancer, a colon cancer, a kidney cancer, a lung cancer, an osteosarcoma, a GIST, a melanoma, a leukaemia and a neuroblastoma.

A preferred breast cancer is a breast cancer conventionally treated with anthracyclins, taxanes, Herceptin and/or a TLR-3 ligand.

A preferred prostate cancer is a prostate cancer conventionally treated with anthracyclins and X-Rays.

A preferred colon cancer is a colon cancer conventionally treated with oxaliplatinum.

A preferred kidney cancer is a kidney cancer conventionally treated with cytokines or anti-angiogenic drugs (sorafenib).

A preferred lung cancer is a lung cancer conventionally treated with X-Rays and platine.

A preferred osteosarcoma and a preferred GIST are respectively an osteosarcoma and a GIST conventionally treated with anthracyclins and/or Glivec.

A preferred melanoma is a melanoma conventionally treated with electrochemotherapy or isolated limb perfusion of high doses of TNFalpha.

The tumour cell mentioned in the present invention is preferably selected from a carcinoma, a sarcoma, a lymphoma, a melanoma, a paediatric tumour and a leukaemia tumour.

Inventors have discovered, in the present invention, that if the patient tumour cells do not spontaneously expose CRT, KDEL receptor and/or ERP57 on their surface, an additional treatment should be administered to said patient to favour a reaction from the immune system against said tumour cells. The exposure can be observed or determined before or after administration of any conventional therapy as described previously. The spontaneous exposure of CRT, KDEL receptor and/or ERP57 on the surface of a tumour cell is preferably observed following the administration of such an appropriate conventional therapy. Again, said conventional therapy directly depends on the nature of the tumour.

The above mentioned additional treatment can be, according to the present invention, an exogenous supply of CRT, KDEL receptor and/or ERp57, and/or the administration of a compound that allows or enhances CRT, KDEL receptor and/or ERp57 exposure at the surface of a tumour cell (such as a PP1/GADD34 inhibitor as explained below), preferably together with a conventional therapeutic agent used in a treatment as described above (in order to obtain a synergistic effect), said conventional treatment being easily selected by the cancerologist, as exemplified previously, according to the nature of the cancer to be prevented or treated.

As indicated previously, an object of the present invention is thus the use of CRT, KDEL receptor and/or ERp57 to prepare a pharmaceutical composition that is preferably intended for administration in combination with a product used in a treatment of cancer, in particular in a conventional treatment of cancer as mentioned previously, to prevent or treat a cancer as defined above, in a mammal, preferably a human.

The pharmaceutical composition is preferably administered during and/or after the above mentioned treatment of cancer.

Another object of the present invention is the use of CRT, KDEL receptor and/or ERp57 to prepare a pharmaceutical composition to prevent or treat an infection as defined above, in a mammal, preferably a human.

The present invention also provides a method for screening or selecting a compound that is able to modify the activity of the immune system towards a cell, the method comprising a step of detecting and/or measuring the level of exposure of CRT, KDEL receptor and/or Erp57 at the surface of the cell in the presence of a test compound, wherein a modified exposure in comparison with a control cell that has not been exposed to or contacted with the test compound is indicative of the capacity of said compound to modify the activity of the immune system towards said cell.

Another object of the present invention is the use of any compound or therapeutic agent that allows or enhances CRT, KDEL receptor and/or ERp57 exposure at the surface of a dying cell, in particular a tumour cell, to prepare a pharmaceutical composition to prevent or treat a cancer or an infection in a mammal, preferably a human. This pharmaceutical composition is preferably intended for administration in combination with a treatment of cancer, and as explained previously, preferably with a treatment that naturally does not induce the exposure of CRT and/or ERp57 on the surface of the tumour cell.

Although different chemotherapeutic agents may kill tumour cells through an apparently homogeneous apoptotic pathway, they differ in their capacity to stimulate immunogenic cell death. Thus, inventors have discovered that anthracyclins and gamma-irradiation cause immunogenic cell death and induce CRT and/or ERp57 exposure on the surface of tumour cells (respectively herein called ecto-CRT and ecto-ERp57), while other pro-apoptotic agents that induce non-immunogenic cell death (such as mitomycin C and etoposide) fail to induce ecto-CRT and/or ecto-Erp57. Depletion of CRT and/or ERp57 abolishes the immunogenicity of cell death elicited by anthracyclins, while exogenous supply of CRT and/or ERp57 or enforcement of CRT and/or ERp57 exposure(s) by pharmacological agents that favour CRT and/or ERp57 translocation to the surface of tumour cells can induce a reaction from the immune system directed against tumour cells, i.e., can enhance the immunogenicity of cell death.

CRT exposure is known to be induced by UVC light (Gardai, S. J. et al. *Cell* 123, 321-34 (2005)). Inventors now demonstrate that CRT exposure is also triggered by anthracyclins (as shown in FIG. 2) and PP1/GADD34 inhibitors (as shown in FIG. 5), and involves the translocation of intracellular CRT to the cell surface through a molecular mechanism involving in particular KDEL and that likewise involves the presence of other saturable CRT receptors (Henson, P. M. & Hume, D. A. *Trends Immunol* 27, 244-50 (2006)) on the cell surface, that can bind exogenous CRT as well as endogenous, preformed CRT.

Inventors herein demonstrate that this CRT protein is strongly (by a factor of 6) induced by doxorubicin and anthracyclin in general (as shown in FIG. 2B and 2C). Immunoblot analyses of 2D gels (not shown) and conventional electrophoreses of purified plasma membrane surface proteins (as shown in FIG. 2C) confirmed the surface exposure of CRT after treatment with anthracyclins. This CRT surface exposure is also detectable by immunofluorescence staining of anthracyclin-treated live cells (as shown in FIG. 2D). Induction of CRT exposure by anthracyclins is a rapid process, detectable as soon as one hour after treatment (as shown in FIG. 1S A,B), and hence precedes the apoptosis-associated phosphatidylserine (PS) exposure (as shown in FIG. 1S C,D). Of note, there was a strong positive linear correlation (p<0.001) between the appearance of CRT at the cell surface (measured at four hours) and the immunogenicity elicited by the panel of 20 distinct apoptosis inducers (FIG. 2E).

The immunogenicity and the immune response can be mediated by specific cells such as dendritic cells (DC). Inventors have shown that anthracyclin-treated tumour cells acquired the property to be phagocytosed by DC few hours after treatment with doxorubicin or mitoxantrone (as shown in FIG. 3A, supplementary FIG. 2A), correlating with the rapid induction of CRT (as shown in FIG. 3B, FIG. 1S A, B) and the acquisition of immunogenicity (as shown in supplementary FIG. 2B).

In response to the mitoxantrone (MTX) anthracylin, a variety of human tumour cell lines expose CRT and/or ERp57 on the surface of their cells. CRT and ERp57 are usually only found within the cell, mostly associated with the endoplasmic reticulum. However, after short exposure with anthracyclins (5 min or longer), CRT and/or ERp57 can be detected on the surface of tumour cells using immunofluorescence staining methods applied to unfixed cells (FIGS. 7A and 7B). Very similar results are obtained upon gamma-irradiation or UVC radiation or exposure to other anthracyclins selected from idarubicin, daunorubicin or doxorubicin.

Accordingly, blockade of the CRT present on the surface of mitoxantrone-treated cancer cells by means of a specific antibody inhibits their phagocytosis by DC (as shown in FIG. 3C). Inversely, addition of recombinant CRT protein (rCRT), which binds to the surface of the cells, reverses the defect induced by antibodies. Hence, ecto-CRT (CRT exposed on the surface of cells) elicits phagocytosis of said cells by DC. Moreover, absorption of rCRT to the plasma membrane surface greatly enhances the immunogenicity of cells that usually fail to induce an immune response such as mitomycin-treated cells (as shown in FIG. 4C) or etoposide-treated cells coated with rCRT and elicits a vigorous anti-tumour immune response in vivo (as shown in FIG. 4D). However, absorption of rCRT to the cell surface without prior treatment with a cell death inducer failed to elicit an anti-cancer immune response.

The inventors have observed that CRT exposure induced by anthracyclins and PP1/GADD34 inhibitors was abolished by latrunculin A, an inhibitor of the actin cytoskeleton (as shown in supplementary FIG. 4). They have shown that PP1/GADD34 inhibition induces CRT exposure and also that this inhibition can improve the anti-tumour immune response as well as the antitumour effects mediated by conventional therapies, in particular chemotherapies, which are non effective when used in the absence of such an inhibition of the PP1/GADD34.

Inventors have discovered that CRT, KDEL receptor and/or ERp57, as well as any compound or therapeutic agent that allows or enhances CRT, KDEL receptor and/or ERp57 exposure at the surface of a tumour cell, are able to improve the efficiency of a therapy of cancer, in particular of a conventional therapy as described above, in a mammal in need thereof, by inducing exposure, preferably an increased exposure of CRT, KDEL receptor and/or ERp57 on the surface of the tumour cell, said exposure being responsible for the induction of an immunogenic apoptosis.

A compound or therapeutic agent usable in the present invention that allows or enhances CRT, KDEL receptor and/or ERp57 exposure at the surface of a tumour cell can be a cytotoxic agent or cell death inducer as described previously.

A preferred compound or therapeutic agent usable in the present invention that allows or enhances CRT, KDEL receptor and/or ERp57 exposure at the surface of a tumour cell, can be selected from (i) CRT, (ii) KDEL receptor, (iii) ERp57, (iv) an inhibitor of the catalytic subunit of the protein phosphatase 1 (PP1), (v) an inhibitor of the protein phosphatase 1 regulatory subunit 15A (GADD34), (vi) an inhibitor of the PP1/GADD34 complex, and (vii) an anthracyclin.

A preferred inhibitor of the catalytic subunit of PP1 can be selected for example from tautomycin, calyculin A and an appropriate siRNA (i.e., a siRNA inhibiting the translation of PP1 or GADD34).

A preferred inhibitor of the PP1/GADD34 complex can be selected for example from salubrinal and particular peptides, as further explained below.

A preferred anthracyclin can be selected for example from doxorubicin, daunorubicin, idarubicin and mitoxantrone.

The present invention thus encompasses the use of at least one compound selected from i) CRT, (ii) KDEL receptor, (iii) ERp57, (iv) an inhibitor of the catalytic subunit of the protein phosphatase 1 (PP1), (v) an inhibitor of the protein phosphatase 1 regulatory subunit 15A (GADD34), (vi) an inhibitor of the PP1/GADD34 complex, and (vii) an anthracyclin, to prepare a pharmaceutical composition to prevent or treat a cancer or an infection, as defined previously in the present application, in a mammal, in particular in a human. The pharmaceutical composition intended to prevent or treat a cancer, is preferably intended to be administered with a product used in a treatment of cancer as explained previously.

In a further embodiment, the present application provides below further compounds that allow or enhance CRT, KDEL receptor and/or ERp57 exposure at the surface of a dying cell, in particular of a tumour cell.

Protein Phosphatase Inhibitors

The present application in particular relates to the use of a protein phosphatase inhibitor selected from an inhibitor of the catalytic subunit of the protein phosphatase 1 (PP1), an inhibitor of GADD34 and an inhibitor of the PP1/GADD34 complex to prepare a pharmaceutical composition to prevent or treat a cancer in a mammal, wherein the pharmaceutical composition is intended for administration in combination with a product used in a treatment of a cancer.

The protein phosphatase inhibitor is preferably selected from:
  an inhibitor of the catalytic subunit of the protein phosphatide 1 (PP1), that can be selected for example from tautomycin, calyculin A and an appropriate siRNA (i.e., a siRNA inhibiting the translation of PP1),
  an inhibitor of GADD34, such as an appropriate siRNA (i.e., a siRNA inhibiting the translation of GADD34), and
  an inhibitor of the PP1/GADD34 complex, such as salubrinal or a peptide as described below, in particular a peptide in the form of a fragment of GADD34 as described below.

This pharmaceutical composition is preferably intended to be used in combination with a therapeutic product, as described above, usable in a conventional therapeutic treatment of cancer, in particular with a chemotherapeutic agent or product, preferably with a chemotherapeutic agent that naturally does not induce the exposure of CRT and/or ERp57 on the surface of a tumour cell.

Also herein disclosed is a protein phosphatase inhibitor selected from an inhibitor of the catalytic subunit of the protein phosphatase 1 (PP1), an inhibitor of GADD34 and an inhibitor of the PP1/GADD34 complex, in combination with a product used in a treatment of a cancer, to prevent or treat a cancer in a mammal.

Inventors indeed herein demonstrate that protein phosphatases have a broader catalytic spectrum than kinases. Phosphatases specificity is indeed increased by their non-covalent interaction with non-catalytic co-factors that determine substrate recognition. Inventors more particularly studied protein phosphatase 1 (PP1) and its subunit GADD34. They surprisingly discovered that an inhibition of PP1, of GADD34 or of their complex (PP1/GADD34) induced an increased location of CRT and/or ERp57 at the cellular surface (as shown in FIG. 5 for CRT).

In a particular embodiment, the present invention relates to the use of anyone of the above mentioned protein phosphatase inhibitors to prepare a pharmaceutical composition intended to be used in combination with a therapeutic product, preferably used in a conventional treatment of cancer, in particular in a chemotherapy, to prevent or treat a cancer (as previously defined), in a mammal, in particular in a human.

A particular pharmaceutical composition of the invention comprises a protein phosphatase inhibitor selected from an inhibitor of PP1, an inhibitor of GADD34 and an inhibitor of the PP1/GADD34 complex, in association with a pharmaceutically acceptable excipient or diluent.

This pharmaceutical composition is preferably intended for administration in combination with a product used in a treatment of cancer for the reasons explained previously.

In a particular embodiment, the present invention relates to the use of anyone of the above mentioned protein phosphatase inhibitors to prepare a pharmaceutical composition to prevent or treat an infectious disease as described previously, in a mammal, in particular in a human. The pharmaceutical composition preferably further comprises a product used in a treatment of a cancer, as defined previously, preferably in a chemotherapy as defined previously.

Particular protein phosphatase inhibitor of the present invention may be selected from tautomycin, calyculin A, salubrinal, appropriate siRNA (as defined previously) and peptidic inhibitors of the PP1/GADD34 complex described below.

Peptidic PP1/GADD34 Inhibitors

Another protein phosphatase inhibitor of the present invention is a peptide consisting in or comprising a fragment of GADD34, wherein said peptide inhibits the formation or activity of the PP1/GADD34 complex in a cell, or a homologous variant thereof comprising substituted amino acid(s) that does not affect its ability to inhibit the formation or activity of the PP1/GADD34 complex.

In the sense of the present invention, a peptide inhibiting the formation of the PP1/GADD34 complex, is a peptide able to compete with GADD34 to form a complex with PP1 and thereby render said complex non functional, i.e., not able to be expressed on the surface of a cell and then to induce a reaction from the immune system.

In the sense of the present invention, a peptide inhibiting the activity of the PP1/GADD34 complex, is a peptide that is responsible for the non expression of said complex on the surface of a cell and/or for the non induction of a reaction of the immune system or for a decreased reaction of the immune system compared with its reaction in the absence of said peptide.

The fragment, as previously mentioned, of GADD34 is preferably a fragment of SEQ ID NO: 1 (human GADD34), i.e., mapgqaphqa tpwrdahpff llspvmglls rawsrlrglg plepwlveav kgaalveagl egeartplai phtpwgrrpg eeaedsggpg edretlglkt ssslpeawgl lddddgmyge reatsvprgq gsqfadgqra plspsllirt lqgsdknpge ekaeeegvae eegvnkfsyp pshreccpav eeeddeeavk keahrtstsa lspgskpstw vscpgeeenq atedkrters kgarktsysp rssgsdprsw eyrsgeasee keekaheetg kgeaapgpqs sapaqrpqlk swwcqpsdee esevkplgaa ekdgeaecpp cipppsaflk awvywpgedt eeeedeeede dsdsgsdeee geaeassstp atgvflkswv yqpgedteee ededsdtgsa edereaetsa stppasaflk awvyrpgedt eeeededvds edkeddseaa lgeaesdphp shpdqsahfr gwgyrpgket eeeeaaedwg eaepcpfrva iyvpgekppp pwapprlplr lqrrlkrpet pthdpdpetp lkarkvrfse kvtvhflavw agpaqaarqg pweqlardrs rfarriaqaq eelspcltpa ararawarlr npplapipal tqtlpsssvp sspvqttpls qavatpsrss aaaaaaldls grrg (SEQ ID NO:1).

The fragment of GADD34 is preferably comprised between amino acid positions 500 and 600, preferably between amino acids positions 530 and 580, even more preferably between positions 540 and 570, in particular between positions 550 and 565, preferably between positions 551 and 562 of SEQ ID NO: 1.

The sequence of the fragment of GADD34 preferably comprises between 5 and 35 amino acids, preferably between 10 and 35 amino acids, even more preferably between 5 and 15 amino acids of SEQ ID NO: 1.

In a preferred embodiment, the inhibitor of the PP1/GADD34 complex is a fragment of GADD34 consisting in a sequence comprised between 5 and 35 amino acids of SEQ ID NO: 1.

A particularly preferred peptide according to the present invention comprises the following sequence: LKARKVRF-SEKV (SEQ ID NO: 2) which is a fragment of GADD34.

The above mentioned peptide according to the invention can further comprise a plasma membrane translocation motif that is capable of binding to the plasma membrane on the surface of a cell. This motif can be used to address the peptide according to the invention to a target cell, for example a tumour cell or an infected cell if required.

The targeted tumour cell is preferably from a carcinoma, a sarcoma, a lymphoma, a melanoma, a paediatric tumour or a leukaemia tumour.

A translocation motif usable in the present invention to target a tumour cell comprises the following sequence: VKKKKIKREIKI (SEQ ID NO: 3) which is a N-terminal DPT-sh1 sequence.

A particular peptide according to the invention comprises the following sequence: VKKKKIKREIKI-LKARKVRF-SEKV (SEQ ID NO: 4) which includes a fragment of GADD34 and a translocation motif.

This peptide has been tested for its capacity to stimulate the exposure of CRT (ecto-CRT), KDEL receptor and/or ERp57 (ecto-ERp57) on the surface of cells, which is, as explained previously, one of the rapid biochemical consequences of PP1/GADD34 inhibition.

As reflected by FIGS. 7A and 7B, the above described peptide comprising SEQ ID NO:4, is capable of inducing the exposure of calreticulin (as measured by immunofluorescence staining of cells, followed by cytofluorometric analysis) in two different cell lines, namely human HCT116 colon cancer cell and murine CT26 colon cancer cells. Similar results were obtained with HeLa cells and mouse embryonic fibroblasts (not shown). As an internal control, inventors generated a mutant peptide (complete sequence: VKKK-KIKREIKI-lkaravafsekv) (SEQ ID NO: 17) in which two amino acids of the GADD34-derived sequence were replaced by alanines. This mutant control peptide did not induce calreticulin exposure, confirming the specificity of the reaction.

The present invention further provides a method, advantageously an in vitro method for screening or selecting a peptide as defined above, capable of inhibiting the formation or activity of the PP1/GADD34 complex in a cell. This method comprises the steps of:
a) providing a test peptide comprising a fragment sequence within SEQ ID NO: 1 or a homologous fragment thereof,
b) contacting the test peptide of step a) with the cell, and
c) detecting and/or measuring the level of exposure of calreticulin (CRT), KDEL receptor and/or ERp57 on the surface of said cell, wherein an enhanced exposure in comparison with a control cell that has not been contacted with or exposed to the test peptide or has been contacted with or exposed to a mutant of said test peptide is indicative of an inhibition of the formation or activity of the PP1/GADD34 complex in the cell.

The fragment sequence of step a) is selected within SEQ ID NO: 1. Said sequence is preferably comprised between amino acids positions 500 and 600, preferably between positions 530 and 580, even more preferably between positions 540 and 570, in particular between positions 550 and 565, preferably between positions 551 and 562 of SEQ ID NO: 1, as described above.

As described above, the fragment sequence selected within SEQ ID NO: 1 preferably comprises between 5 and 35 amino acids, preferably between 10 and 35 amino acids, even more preferably between 5 and 15 amino acids of SEQ ID NO: 1.

The present invention further provides a method to improve the activity of the peptide selected with a method as described above comprising a step of substituting at least one amino acid by a different amino acid that enhances the ability of the sequence to inhibit the formation or activity of the PP1/GADD34 complex.

The at least one different amino acid that enhances the ability of the sequence to inhibit the formation or activity of the PP1/GADD34 complex can be any amino acid (i) providing the peptide with an increased resistance against enzymes such as peptidases or proteases, (ii) improving the peptide bioavailability and/or (iii) enhancing its inhibitory function against the formation or activity of the PP1/GADD34 complex.

Several Methods usable to detect CRT, KDEL receptor and/or ERp57 on the cell surface are well-known from the skilled man of the art.

In order to detect CRT, KDEL receptor and/or ERp57 on the cell surface, immunoblotting (in particular Western blot) or proteomics as well as any other method known from the man of the art, can be applied to a tumour specimen (such as for example a biopsy, a cell aspirate harvested from tumour bed, cytospins or circulating tumour cells in the case of a leukaemia).

Regarding proteomics, the exposure of CRT, KDEL receptor and/or ERp57 may be detected using an antibody-based biosensors, prepared with an antibody selected from an anti-CRT antibody, an anti-KDEL receptor antibody and an anti-Erp57 antibody, said antibody being able to detect the endogenous form of CRT, KDEL receptor and/or Erp57, their recombinant forms as well as their homologous variants or mimetics. The antibody is advantageously coupled with a detectable conjugate.

To detect CRT, KDEL receptor and/or Erp57, the present invention provides a kit allowing the detection of said proteins on the cell surface.

This kit comprises at least an anti-CRT antibody, an anti-KDEL receptor antibody or an anti-ERp57 antibody.

Immunofluorescence staining or FACS (Fluorescent Activated Cell Sorting) analyses (flow cytometry analyses) is an example of an appropriate method to detect the translocation of CRT, KDEL receptor and/or Erp57 from the inside to the surface of a tumour cell, in particular of a tumour cell that has been previously submitted to a therapeutic treatment of cancer.

The selected peptide obtainable with a method as described above may further be modified to incorporate a plasma membrane translocation motif as defined previously.

The present invention thus also provides a method for preparing such a modified peptide, comprising the fusion of (i) a selected peptide comprising a fragment of SEQ ID NO: 1, or of a homologous variant thereof, and of (ii) a plasma membrane translocation motif that binds to the surface of a cell.

The above described peptides according to the present invention as well as the peptides obtainable by a method of screening as described previously, or their homologous variants, are each herein provided as new medicaments.

The present invention further includes the use of a protein phosphatase inhibitor as described previously, in particular of an inhibitor of the catalytic subunit of the protein phosphatase 1 (PP1) such as tautomycin and calyculin A, an inhibitor of GADD34, and/or an inhibitor of the PP1/GADD34 complex such as salubrinal and a peptide as defined above, to prepare a pharmaceutical composition to prevent or treat a cancer, in particular a cancer selected from a breast cancer, a prostate cancer, a colon cancer, a kidney cancer, a lung cancer, an osteosarcoma, a GIST, a melanoma, a leukaemia and a neuroblastoma.

Also herein disclosed is a protein phosphatase inhibitor as defined above, in combination with a product used in a treatment of a cancer, as defined previously, to prevent or treat a cancer preferably selected from a breast cancer, a prostate cancer, a colon cancer, a kidney cancer, a lung cancer, an osteosarcoma, a GIST, a melanoma, a leukaemia and a neuroblastoma, in a mammal.

The pharmaceutical compositions herein disclosed are preferably, for the reasons provided before, intended for administration in combination with a product used in a conventional treatment of cancer as defined before, in particular with a conventional treatment of cancer, such as a chemotherapeutic agent.

Also herein provided, is a pharmaceutical composition comprising such a protein phosphatase inhibitor and, preferably a product used in a treatment of a cancer, as defined previously, in association with a pharmaceutically acceptable excipient or diluent.

Appropriate excipient, diluent or carrier usable in the all present invention may be selected for example from saline, isotonic, sterile or buffered solutions, etc. They can further comprise stabilizing, sweetening and/or surface-active agents, etc. They can be formulated in the form of ampoules, flasks, tablets, or capsules, by using techniques of galenic known per se.

The conventional treatment of cancer is, as explained previously, preferably selected from (i) a chemotherapy, (ii) a radiotherapy, (iii) a hormonotherapy, (iv) an immunotherapy, (v) a specific kinase inhibitor-based therapy, (vi) an antiangiogenic agent based-therapy, and (vii) a monoclonal antibody-based therapy. A particularly preferred treatment of cancer is chemotherapy. The chemotherapy preferably uses a product selected from an anthracyclin, an immune response modulator, a hormone and a tyrosine kinase inhibitor. The anthracyclin is preferably selected from doxorubicin, daunorubicin, idarubicin and mitoxantrone.

In a particular embodiment, the present invention relates to the use of anyone of the above mentioned protein phosphatase inhibitors to prepare a pharmaceutical composition to prevent or treat a cancer (as previously defined) or an infection (as previously defined), in a mammal, in particular in a human.

In a particular embodiment, the protein phosphatase inhibitor or the pharmaceutical composition comprising such a protein phosphatase inhibitor or a mixture of several protein phosphatase inhibitors, is intended for administration in combination with a treatment of cancer as defined above, preferably a conventional treatment of cancer as defined previously.

Kinase Activators

On the other hand, eIF2alpha is a protein that is typically hyperphosphorylated under endoplasmic reticulum stress due to the activation of stress kinases (Zhang, K. & Kaufman, R. J. *J Biol Chem* 279, 25935-8 (2004)). In a further aspect of the invention, inventors have thus observed that kinases, known to phosphorylate eIF2alpha could be involved in the increased CRT, KDEL receptor and/or ERp57. translocation and exposure at the cell surface. They have discovered that such kinases can be selected from the eukaryotic translation initiation factor 2-alpha kinases, for example heme-regulated inhibitor (HRI, also called Hemin-sensitive initiation factor 2-alpha kinase or eukaryotic translation initiation factor 2-alpha kinase 1), RNA activated protein kinase (PKR, also called eukaryotic translation initiation factor 2-alpha kinase 2), PKR-like ER-localized eIF2alpha kinase (PERK, also called eukaryotic translation initiation factor 2-alpha kinase 3) and GCN2 (also called eukaryotic translation initiation factor 2-alpha kinase 4).

The present invention also concerns a kinase activator selected from a compound activating (i) an eukaryotic translation initiation factor 2-alpha kinase (HRI), (ii) a RNA activated protein kinase (PKR) such as the Toll Like Receptor 3 (TLR-3) ligands, (iii) a PKR-like ER-localized eIF2alpha kinase and (iv) GCN2, as a medicament.

In a particular embodiment, the present invention encompasses the use of a kinase activator as mentioned above to prepare a pharmaceutical composition to prevent or treat a cancer or an infection, as defined previously in the present application, in a mammal, in particular in a human.

Also herein disclosed is a kinase activator as mentioned above to prevent or treat a cancer or an infection in a mammal, in particular in a human.

The pharmaceutical composition to prevent or treat a cancer, is preferably a composition that is intended for administration in combination with a product used in a treatment of cancer, preferably in a conventional treatment of cancer as defined previously.

Although CRT adsorbed to the surface of live cells enhances the phagocytosis by dendritic cells (DC) in vitro (as shown in FIG. 3E), CRT had indeed to be combined with a cell death inducer to elicit a local (as shown in FIG. 4C) or systemic immune response in vivo (as shown in FIG. 4D, FIG. 6). Inventors have demonstrated that the combination of a cell death inducer (etoposide or mitomycin C) and recombinant calreticulin (rCRT), recombinant KDEL receptor or recombinant ERp57 (rERp57) was able to cause tumour regression, in immunocompetent (but not in immunodeficient) animals. Similarly, etoposide or mitomycin C can be combined with drugs that induce CRT, KDEL receptor and/or ERp57 exposure (salubrinal or tautomycin), leading to stable disease or complete tumour regression in immunocompetent (but not in athymic) hosts (as shown in FIG. 6A, B). Live CT26 cells failed to grow in animals that had been cured from CT26 tumours, indicating the establishment of a permanent anti-tumour immune response. As demonstrated herein, this knowledge can be employed to stimulate an efficient anti-tumour immune response in which a non-immunogenic chemotherapeutic agent (selected from a therapeutic agent used in a conventional treatment of cancer as exemplified previously) becomes immunogenic when combined with one of the above described compounds, for example rCRT, rKDEL receptor, rERp57 and/or a PP1/GADD34 inhibitor. These results delineate a strategy of "immunogenic chemotherapy" to cure an established cancer such as those mentioned before or to cure an infection such as a viral, bacterial, fungal or parasitic infection.

Anti-CRT and Anti-ERp57 Antibodies

In autoimmune disorders such as Systemic Lupus Erythematosus (SLE), rheumatoid arthritis, dermatitis, allergy, graft versus host disease, transplant rejection, or too-strong-immunogenicity in forced apoptosis, i.e., excessive and undesired immunogenicity induced by one of the compounds described above that favour CRT and/or ERp57 exposure at the surface of a dying cell, it is, contrary to the previously described aims, interesting to limit the action of the immune system on cell death.

Inventors have observed that this could be obtained by a decreased translocation of CRT and/or ERp57 to the cell surface using blocking or neutralising anti-calreticulin and/or anti-ERp57 antibodies. An inhibitory or competitive peptide interfering with the translocation of CRT and/or ERp57 could also decrease the amount of CRT and/or ERp57 at the cell surface and then reduce the immune response in those situations.

The present invention thus also encompasses blocking or neutralizing anti-CRT and/or anti-ERp57 antibody(ies) and an inhibitory/competitive peptide interfering with the increased translocation of CRT and/or ERp57 as medicaments, and in particular their respective use to prepare a pharmaceutical composition to prevent or treat in particular an autoimmune disorder as described above, an allergy, a graft versus host disease or a transplant rejection in a mammal, preferably in a human.

The present invention further describes a particular pharmaceutical composition comprising a blocking or neutralizing anti-CRT, anti-KDEL receptor or anti-Erp57 antibody, or an inhibitory/competitive peptide interfering with the increased translocation of CRT and/or Erp57 on the cell surface, in association with a pharmaceutically acceptable excipient or diluent.

This pharmaceutical composition is preferably intended for administration in combination with a treatment of cancer for the reasons explained previously.

Method to Prevent or Treat a Disease

The present invention also relates to a method to prevent or treat a disease, in particular a cancer or an infection, as defined herein, comprising the administration to a mammal, in particular a human, in need thereof, of at least one compound selected from i) CRT, (ii) KDEL receptor, (iii) ERp57, (iv) an inhibitor of the catalytic subunit of the protein phosphatase 1 (PP1), (v) an inhibitor of the protein phosphatase 1 regulatory subunit 15A (GADD34), (vi) an inhibitor of the PP1/GADD34 complex, (vii) an anthracyclin, and (viii) a kinase activator selected from the above mentioned kinases.

This method may be applied in combination with a distinct treatment of cancer, such as those previously described.

The above method to prevent or treat a disease may comprise a step of directly injecting the selected compound(s) in the tumour of the subject in need thereof.

DISCLOSURE OF THE INVENTION

Hence, the present invention concerns the calreticulin for its use as a medication for the treatment of a disease in a mammal, said medication inducing an increased location of calreticulin at the cellular surface.

The present invention is based on the identification of CRT exposure as a determining feature of anti-cancer immune responses and delineates a strategy of immunogenic chemotherapy.

The location of the CRT at the cellular surface could be the result of the translocation of intracellular CRT to the cell surface or the result of the translocation of extracellular CRT to the cell surface. So, the present invention concerns the application as a medication wherein the calreticulin (endogenous form or recombinant form or mimetic form) translocation is from the cytoplasm to the membrane of cells or from the extracellular medium to the membrane of cells. As mimetic form, it should be understood a truncated form of the calreticulin or part(s) of calreticulin or hybrids, exhibiting same properties as native form of calreticulin (ie location at the cellular surface).

Furthermore, the inventors have shown that the calreticulin present in an increased amount at the cell surface renders the dying cells palatable to phagocytic cells such as dendritic cells. These cells interact with the immune system and then induce an immune response, that render the calreticulin as an inducer of immunogenic apoptosis. The present invention also concerns calreticulin for its use as a medication for the treatment of a disease in a mammal, said medication inducing an immunogenic apoptosis.

Preferably, by this application as a medication, the disease treated is a cancer such as breast cancer, prostate cancer, melanoma, colon cancer, etc., or an infection like viral or bacterial or fungal or parasitic infection.

The present invention exposes calreticulin for its use as a medication for the treatment of a disease in a mammal, said medication improving the efficiency of chemotherapy in a mammal in need of such chemotherapy by inducing an increased location of CRT at cell surface and/or induction of immunogenic apoptosis.

CRT exposure is known to be induced by UVC light (Gardai, S. J. et al. Cell 123, 321-34 (2005)).

But it appears that CRT exposure is also triggered by anthracyclins (as shown in FIG. 2) and PP1/GADD34 inhibitors (as shown in FIG. 5), involving the translocation of intracellular CRT to the cell surface through a molecular mechanism that is not fully understood and that likewise involves the presence of saturable CRT receptors (Henson, P. M. & Hume, D. A. Trends Immunol 27, 244-50 (2006)) on the cell surface that can bind exogenous CRT as well as endogenous, preformed CRT.

Indeed, the inventors have shown that this CRT protein was strongly (by a factor of 6) induced by doxorubicin and anthracyclin in general (as shown in FIGS. 2B and 2C). Immunoblot analyses of 2D gels (not shown) and conventional electrophoreses of purified plasma membrane surface proteins (as shown in FIG. 2C) confirmed the surface exposure of CRT after treatment with anthracyclins. This CRT surface exposure was also detectable by immunofluorescence staining of anthracyclin-treated live cells (as shown in FIG. 2D). The induction of CRT exposure by anthracyclins was a rapid process, detectable as soon as 1 h after treatment (as shown in FIG. 1S A,B), and hence preceded the apoptosis-associated phosphatidylserine (PS) exposure (as shown in FIG. 1S C,D). Of note, there was a strong positive linear correlation ($p<0.001$) between the appearance of CRT at the cell surface (measured at 4 h) and the immunogenicity elicited by the panel of 20 distinct apoptosis inducers (FIG. 2E).

The immunogenicity and the immune response could be mediated by specific cells: dendritic cells (DC). The inventors have shown that anthracyclin-treated tumour cells acquired the property to be phagocytosed by DC a few hours after treatment with doxorubicin or mitoxantrone (as shown in FIG. 3A, supplementary FIG. 2A), correlating with the rapid induction of CRT (as shown in FIG. 3B, FIG. 1S A, B) and the acquisition of immunogenicity (as shown in supplementary FIG. 2B).

Accordingly, blockade of the CRT present on the surface of mitoxantrone-treated cancer cells by means of a specific antibody inhibited their phagocytosis by DC (as shown in FIG. 3C). Inversely, addition of recombinant CRT protein (rCRT), which binds to the surface of the cells, could reverse the defect induced by the blockade of CRT by antibodies. Hence, surface CRT elicits phagocytosis by DC. Moreover, absorption of rCRT to the plasma membrane surface greatly enhanced the immunogenicity of cells that usually fail to induce an immune response such as mitomycin-treated cells (as shown in FIG. 4C) or etoposide-treated cells coated with rCRT and elicited a vigorous anti-tumour immune response in vivo (as shown in FIG. 4D). However, absorption of rCRT to the cell surface without prior treatment with cell death inducers failed to elicit an anti-cancer immune response. The present invention deals with the recombinant calreticulin for its use as a medication for the treatment of a disease in a mammal, said medication, after the administration of a cell-death inducer (such as etoposide or mitomycine C), inducing an immunogenic apoptosis.

Accordingly, the present invention also concerns the protein phosphatase inhibitor, as the catalytic subunit of the protein phosphatase 1 (PP1) inhibitor, the GADD34 inhibitor or the complex PP1/GADD34 inhibitor, for its use as a medication for the treatment of a disease in a mammal, said inhibitor inducing an increased location of endogenous calreticulin at the cellular surface.

Furthermore, the present invention is directed to the protein phosphatase inhibitor, as the catalytic subunit of the protein phosphatase 1 (PP1) inhibitor, the GADD34 inhibitor or the complex PP1/GADD34 inhibitor, for its use as a medication for the treatment of a disease in a mammal, said inhibitor inducing an immunogenic apoptosis by increased calreticulin translocation at the cellular surface (as shown in FIG. 5).

The inventors have observed that CRT exposure induced by anthracyclins and PP1/GADD34 inhibitors was abolished by latrunculin A, an inhibitor of the actin cytoskeleton and exocytose (as shown in supplementary FIG. 4). They have also shown not only that PP1/GADD34 inhibition induces CRT exposure but also that this process can then improve the anti-tumour immune response.

This present invention also concerns the protein phosphatase inhibitor, as the catalytic subunit of the protein phosphatase 1 (PP1) inhibitor, the GADD34 inhibitor or the complex PP1/GADD34 inhibitor, for its use as a medication for the treatment of a disease in a mammal, said inhibitor improving the efficiency of chemotherapy in a mammal in need of such chemotherapy by inducing an increased location of calreticulin at the cellular surface and/or an immunogenic apoptosis.

Moreover, an amount of such inhibitor of PP1 or GADD34 or the complex PP1/GADD34 described above can be used in a pharmaceutical composition promoting an increased translocation of the calreticulin protein from the cytoplasm to the cell membrane which thus induces an immune response during apoptosis in a mammal.

Said inhibitor-comprised pharmaceutical composition promoting an increased translocation of the calreticulin from the cytoplasm to the cell surface can also ameliorate chemotherapy response in a mammal.

The inhibitor of PP1 or GADD34 or PP1/GADD34 is advantageously chosen among tautomycin, calyculin A or salubrinal.

On the other hand, eIF2alpha is a typically hyperphosphorylated in endoplasmic reticulum stress due to the activation of stress kinases (Zhang, K. & Kaufman, R. J. *J Biol Chem* 279, 25935-8 (2004)). The inventors have observed that kinases, known to phosphorylate eIF2alpha could be involved in the increased calreticulin translocation and exposure at the cell surface. These kinases are the eukaryotic translation initiation factor 2-alpha kinases, for example heme-regulated inhibitor (HRI, also called Hemin-sensitive initiation factor 2-alpha kinase or eukaryotic translation initiation factor 2-alpha kinase 1), protein kinase RNA activated (PKR, also called eukaryotic translation initiation factor 2-alpha kinase 2), PKR-like ER-localized eIF2alpha kinase (PERK, also called eukaryotic translation initiation factor 2-alpha kinase 3) and GCN2 (also called eukaryotic translation initiation factor 2-alpha kinase 4).

The present invention concerns also kinase activator, such as a compound activating one of the eukaryotic translation initiation factor 2-alpha kinases, for example heme-regulated inhibitor (HRI, also called Hemin-sensitive initiation factor 2-alpha kinase or eukaryotic translation initiation factor 2-alpha kinase 1), protein kinase RNA activated (PKR, also called eukaryotic translation initiation factor 2-alpha kinase 2), PKR-like ER-localized eIF2alpha kinase (PERK, also called eukaryotic translation initiation factor 2-alpha kinase 3) and GCN2 (also called eukaryotic translation initiation factor 2-alpha kinase 4), for its use as a medication for the treatment of a disease such as a cancer or a viral infection in a mammal, said activator inducing an increased location of endogenous calreticulin at the cellular surface.

The disease treated by such use of medication comprising this activator is a cancer (breast cancer, prostate cancer, melanoma, colon cancer, etc.) or an infection (viral, bacterial, fungal or parasitic infection).

The present invention also provides the application as a medication, comprising at least calreticulin or inhibitor of PP1, GADD34 or PP1/GADD34 or anthracyclin or an activator of said four kinases or anti-calreticulin antibodies or inhibitory/competitive peptide, said medication improves cancer treatment such as tumours sensitive to VP16/etoposide, radiotherapy or immunotherapy ie melanoma, kidney cancer, colon cancer, breast or lung tumours, osteosarcoma.

During autoimmune disorders such as Systemic Lupus Erythematosus (SLE), rheumatoid arthritis, dermatitis, allergy, graft versus host, transplant rejection, or too-strong-immunogenicity in forced apoptosis, it will be interesting to limit the immunogenicity of cell death. The inventors have observed that this could be obtained by a decreased translocation of calreticulin to the cell surface by the use of blocking or neutralising antibodies anti-calreticulin. An inhibitory or competitive peptide interfering with the translocation of calreticulin could also decrease the amount of calreticulin at the cell surface and then reduce the immunogenicity and the immune response in those diseases.

Thus, the present invention also relates to blocking or neutralizing antibody anti-calreticulin or inhibitory/competitive peptide, interfering with the increased translocation of calreticulin and therefore in the immunogenicity of cell death for its use as a medication for the treatment of autoimmune disorders (SLE, rheumatoid arthritis, dermatitis), allergy, graft versus host disease, transplant rejection.

In one embodiment of the invention, the anthracyclin as cell death agent can also be used in the preparation of a medication for the treatment of a disease in a mammal, said medication inducing an increased location of calreticulin at the cellular surface.

The anthracyclin can also be used in the preparation of a medication for the treatment of a disease such as cancer or viral infection in a mammal, said medication promoting an induction of immunogenic apoptosis by increased calreticulin translocation at the cellular surface.

The present invention also deals with the use of anthracyclin in the preparation of a medication for the treatment of a disease such as cancer or viral infection in a mammal, said medication improving the efficiency of chemotherapy in a mammal in need of such chemotherapy by inducing an increased location of calreticulin at the cellular surface and/or an immunogenic apoptosis.

Moreover, the present invention concerns also a pharmaceutical composition which comprises an amount of an anthracyclin promoting an increased translocation of the calreticulin protein from the cytoplasm to the cell membrane which thus induces an immune response during apoptosis in a mammal.

Said anthracyclin-comprised pharmaceutical composition promoting an increased translocation of the calreticulin from the cytoplasm to the cell surface can also improve chemotherapy response in a mammal.

The present invention also provides a method promoting the chemotherapy treatment response in a mammal including administration of the pharmaceutical composition comprising an amount of anthracyclin to a mammal in need by inducing an increased location of calreticulin at the cellular surface and/or an immunogenic apoptosis.

The anthracyclin can be doxorubicin, idarubicin or mitoxantrone.

Although CRT adsorbed to the surface of live cells did enhance their phagocytosis by DC in vitro (as shown in FIG. 3E), CRT had to be combined with a cell death inducer to elicit a local (as shown in FIG. 4C) or systemic immune response in vivo (as shown in FIG. 4D, FIG. 6). In therapeutics, the inventors have shown that the combination of a cell death inducer (etoposide or mitomycin C) plus calreticulin (rCRT) was able to cause tumour regression, in immunocompetent (but not in immunodeficient) animals. Similarly, etoposide or mitomycin C could be combined with drugs that induce CRT exposure (salubrinal or tautomycin), leading to stable disease or complete tumour regression in immunocompetent (but not in athymic) hosts (as shown in FIG. 6A, B). Live CT26 cells failed to grow in animals that had been cured from CT26 tumours, indicating the establishment of a permanent anti-tumour immune response. As shown here, this knowledge can be employed to stimulate an efficient antitumour immune response in which a non-immunogenic chemotherapeutic agent becomes immunogenic when combined with rCRT or PP1/GADD34 inhibitors. These results delineate a strategy of immunogenic chemotherapy for the cure of established cancer such as breast cancer, prostate cancer, melanoma, colon cancer, etc.) or for cure of an infection (viral, bacterial, fungal or parasitic infection).

The present invention also concerns a product containing a chemotherapeutic agent and recombinant calreticulin as a combination product for its use in the treatment of disease.

The present invention also deals with product containing a chemotherapeutic agent and the inhibitors (such as the catalytic subunit of the protein phosphatase 1 (PP1) inhibitor, the GADD34 inhibitor or the complex PP1/GADD34 inhibitor) as a combination product for its use in the treatment of disease. This combination product could be used for the treatment of a disease such as a cancer (breast cancer, prostate cancer, melanoma, colon cancer, etc.) or an infection (viral, bacterial, fungal or parasitic infection).

The chemotherapeutic agent could be etoposide, mitomycin C, anthracyclin and others well known in therapeutics. The present invention also provides a product of combination described just above (chemotherapeutic agent and calreticulin or cell death agent and said inhibitor) wherein said product improves cancer treatment such as tumours sensitive to VP16/etoposide, radiotherapy or immunotherapy i.e. melanoma, kidney cancer, colon cancer, breast or lung tumours, osteosarcoma.

The present invention would also be directed to a method inducing increased calreticulin translocation from the cytoplasm to the cell surface to enhance an immune response in the apoptosis phenomenon in a mammal, said method comprising administering pharmaceutically effective amount of an inhibitor as the catalytic subunit of the protein phosphatase 1 (PP1) inhibitor, the GADD34 inhibitor or the complex PP1/GADD34 inhibitor.

Differently, the present invention includes also a method inducing increased calreticulin translocation from the cytoplasm to the cell surface to enhance an immune response in the apoptosis phenomenon in a mammal, said method comprising administering pharmaceutically effective amount of an anthracyclin.

The increased calreticulin translocation is preferably from cytoplasm to the membrane of tumourous cells.

This method improves cancer treatment, preferably those tumours sensitive to VP16/etoposide, radiotherapy, or immunotherapy i.e. melanoma, kidney cancer, colon cancer, breast or lung tumours, osteosarcoma etc.

Preferably, this method is directed to treat chemosensitive cancers as much as immunosensitive cancers.

This method shows increased efficiency of chemotherapy in a mammal in need of such chemotherapy.

Preferably, the mammal treated is a human.

Furthermore, the location of calreticulin protein at the cell surface may be realised by antibodies anti-calreticulin which detect the endogenous form of calreticulin, a recombinant form and the mimetic form. A method of detection of all forms of calreticulin protein at the cellular surface is also an object of the present invention. This could be done in vitro, ex vivo or in vivo. The methods used to detect this calreticulin protein at the cell surface are well-known by the skilled man of the art. These methods comprise immunochemistry on tissue sections (frozen or paraffined), EIA assays such as ELISA on tumour lysates, confocal immunofluoresence or flow cytometry analyses of cytospins, cell aspirates harvested from tumour beds or autoimmune lesions. One object of the present invention is also to develop a method of quantitative detection of the calreticulin (all forms) at the cellular surface. The immunogenicity of the apoptosis is correlated to the amount of calreticulin present at the cell surface. The more calreticulin at the cellular surface, the more immunogenic apoptosis. This method of detection can serve to predict the immunogenicity of the apoptosis. In addition, the effectiveness of a chemotherapy is correlated to the efficiency of the immune response, therefore the immunogenicity of the apoptosis. The more the immunogenic apoptosis, the more the therapeutic efficiency of a chemotherapy. This method of detection of calreticulin at the cell surface can be used for prediction of immunogenic apoptosis and also for therapeutic efficiency of a chemotherapy. The calreticulin in these methods is used as a predictive marker of both immunogenic apoptosis and therapeutic efficiency of a chemotherapy. This method of quantitative detection can also be advantageous to predict risks of forced apoptosis that becomes too immunogenic. Inhibition of the translocation of the calreticulin at the cellular surface could decrease the immunogenicity of the calreticulin and thus reduce or block (in the best case) the immune response.

There is a basal amount of calreticulin at the cellular surface and the increased amount of calreticulin allows to predict an immunogenic apoptosis and/or a therapeutic efficiency of a chemotherapy. By comparison between before and after chemotherapy, the amount of calreticulin at the cell surface is generally largely increased and the increase will be a good predictive marker for immunogenic apoptosis, therapeutic efficiency of a chemotherapy, immunogenic viral infection but also for autoimmune diseases or transplantation rejection/GVH disease. The present invention also provides a method of detection of the calreticulin at the cell surface wherein the calreticulin at the cell surface is used as a predictive marker of immunogenic viral infection or autoimmune diseases or transplantation rejection/GVH disease.

Additionally, to detect calreticulin, the present invention also provides a kit of detection of the calreticulin protein at the cell surface, according to the method described above, such kit comprising at least anti-calreticulin antibodies. In an embodiment of the invention, this kit of detection could also bean quantitative one for the detection quantitative of calreticulin at the cellular surface, said kit comprising at least antibodies anti-calreticulin.

The present invention also concerns a kit of prediction of immunogenic apoptosis of tumourous cells and/or of a therapeutic efficiency of a chemotherapy, comprising at least anti-calreticulin antibodies for detection of calreticulin protein at the cell surface. When a large amount of calreticulin is detected, the apoptosis of tumourous cells will be immunogenic and the efficiency of the chemotherapy will be ameliorated. A kit of prediction of immunogenic viral infection or autoimmune diseases or transplantation rejection/GVH disease, said kit comprising at least anti-calreticulin antibodies for detection of calreticulin protein at the cellular surface is also provided by the present invention.

The present invention concerns also a method of detection of the calreticulin protein at the cellular surface for the screening of direct or indirect immunogenic drugs and the method of screening for immunogenic drugs including a step of detection of the calreticulin protein at the cell surface, comprising at least anti-calreticulin antibodies for the screening of direct or indirect immunogenic drugs.

The screening of direct and indirect immunogenic drugs could lead to finding more efficient anti-tumourous agents. For the direct method, human tumour cell lines must be chosen and then their incubation with a drug panel should allow to detect if there is a spontaneous CRT translocation from the cytoplasm to the cellular surface by flow cytometry or confocal. For the indirect method of screening, the inventors chose human tumour cell lines where apoptosis is obtained after etoposide treatment but no CRT translocation at the cellular surface. Then, a drug panel is used to detect which one can reverse this phenomenon. This is used to find new inhibitors of the PP1/GADD34 complex or new activators of kinases GCN2, HRI, PERK, PKR.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1 shows immunogenic cell death induced by anthracyclins.

Figure 1A:
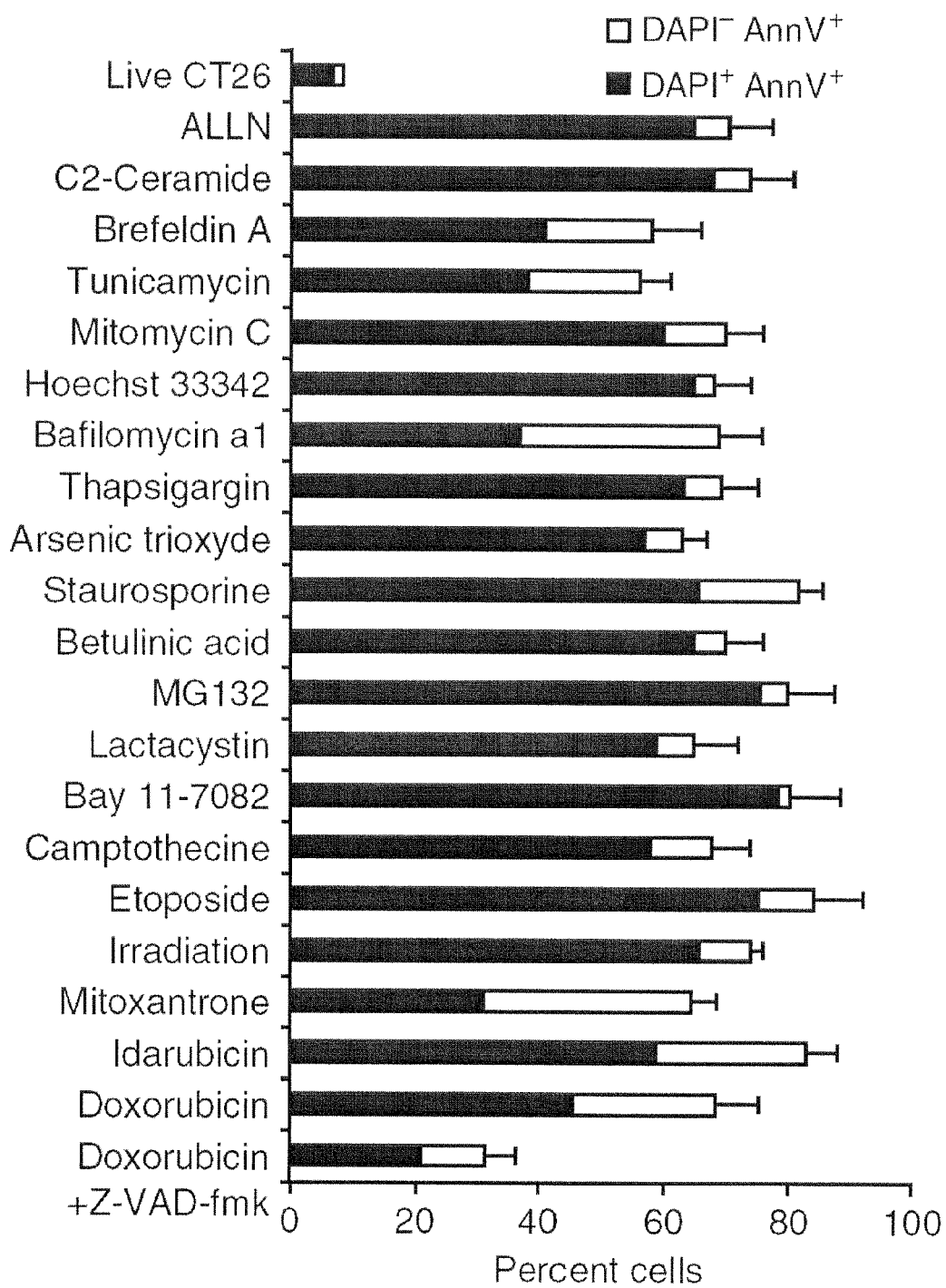
FIG. 1A: Frequency of dead and dying cells after treatment with distinct chemotherapeutic agents. CT26 cells were cultured for 24 hours in the presence of the indicated agents, as described in Materials and Methods, and then were stained with Annexin V-FITC and the vital dye DAPI.

CT26 cells cultured as in FIG. 1A were injected into the left flank, followed by injection of live tumour cells in the right flank 8 days later. The percentage of tumour free mice was determined 120 days later as in FIG. 1C.

Figure 1B:
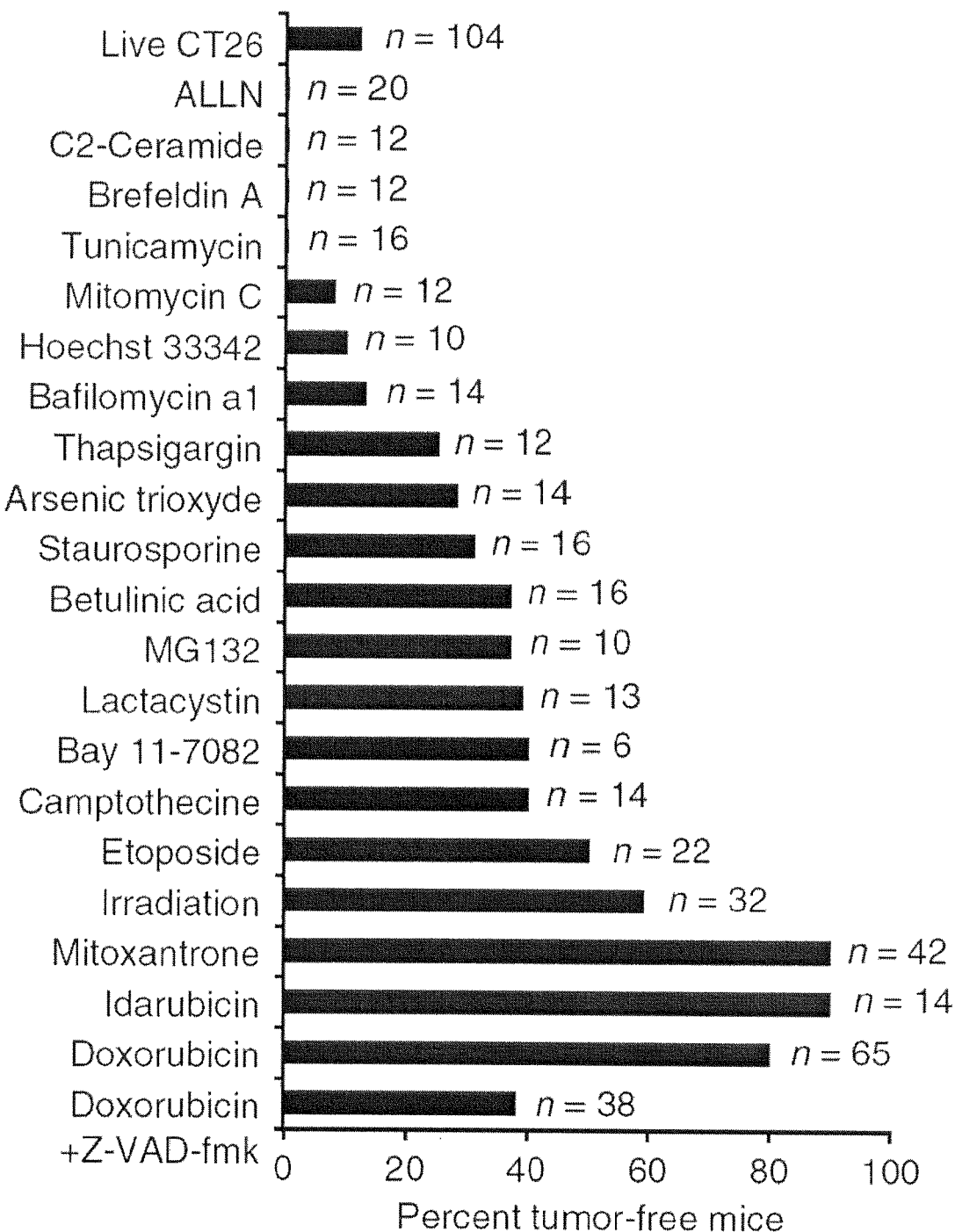
FIG. 1B: Identification of immunogenic cell death inducers.
Figure 1C:
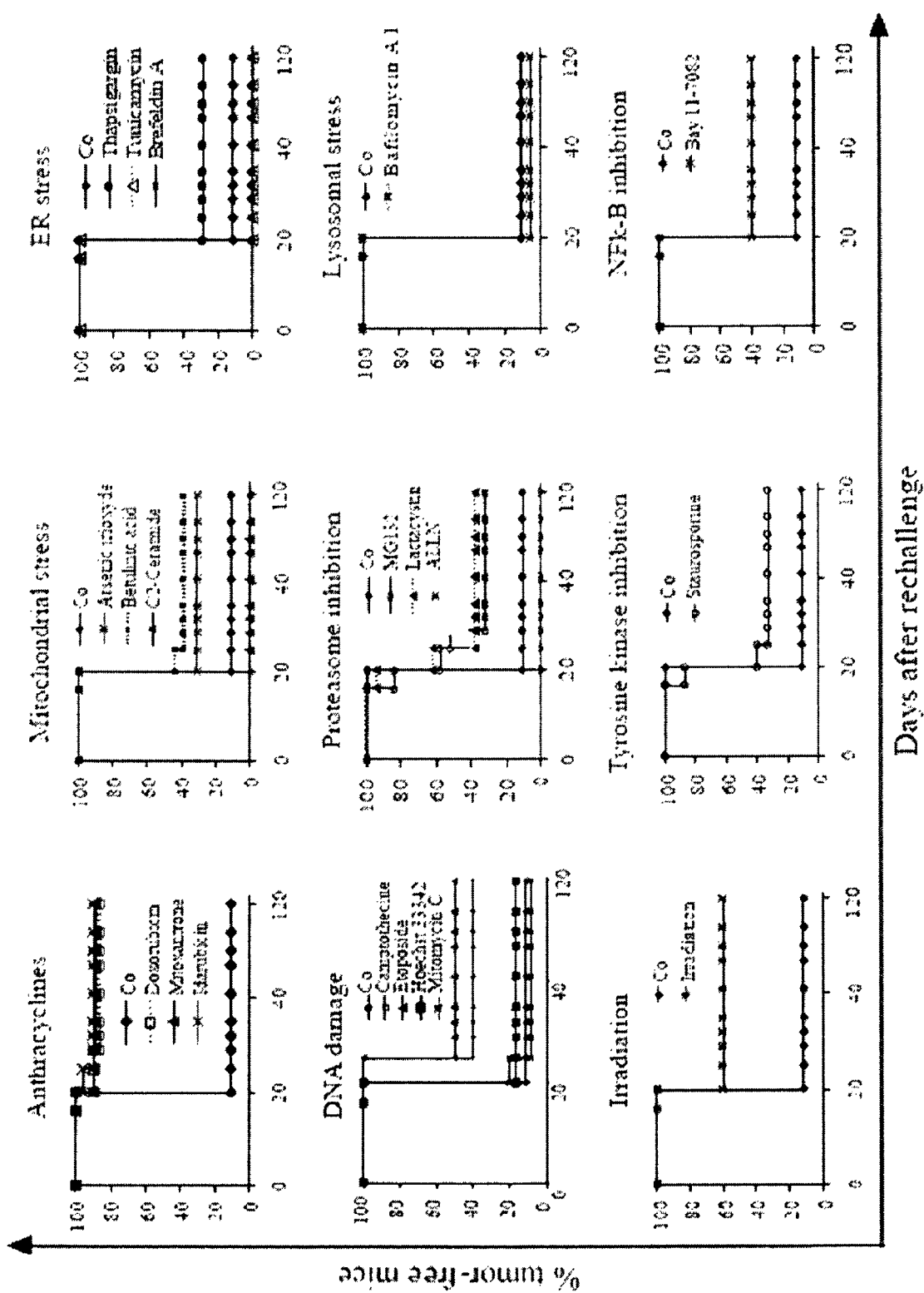
FIG. 1.

FIG. 1C: Incidence of tumours after inoculation of dying cells. The data show the actual frequency of tumour-free mice, for the experiment summarized in FIG. 1B. Day 1 was considered the day of inoculation of dying tumour cells, 1 week before challenge with dying tumour cells.

Figure 1S:
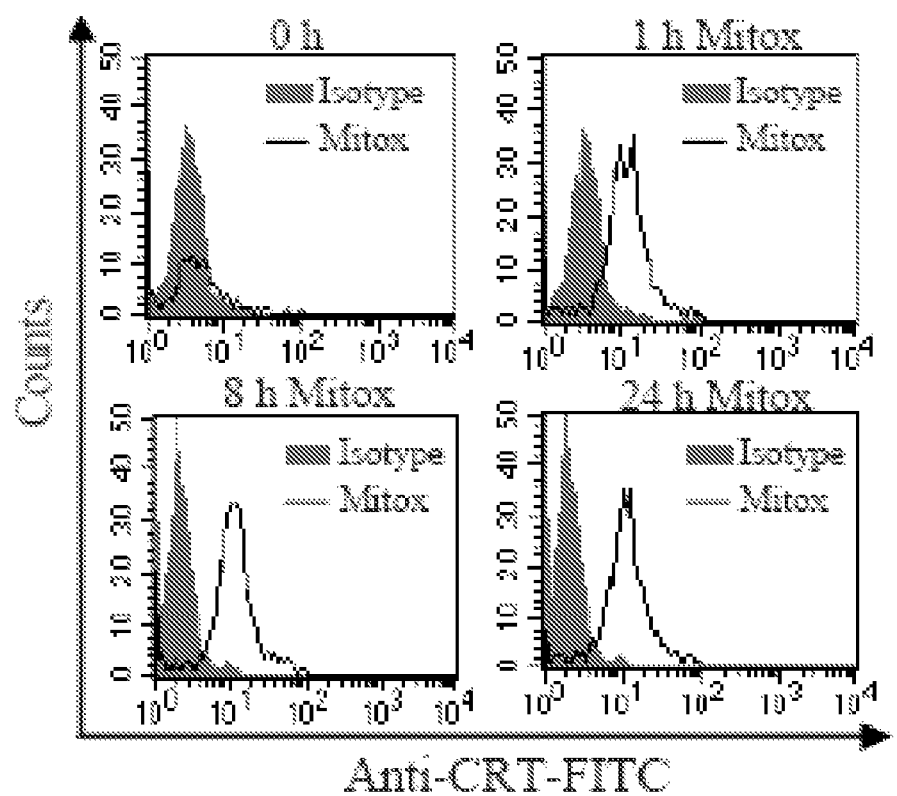
Figure 1S:
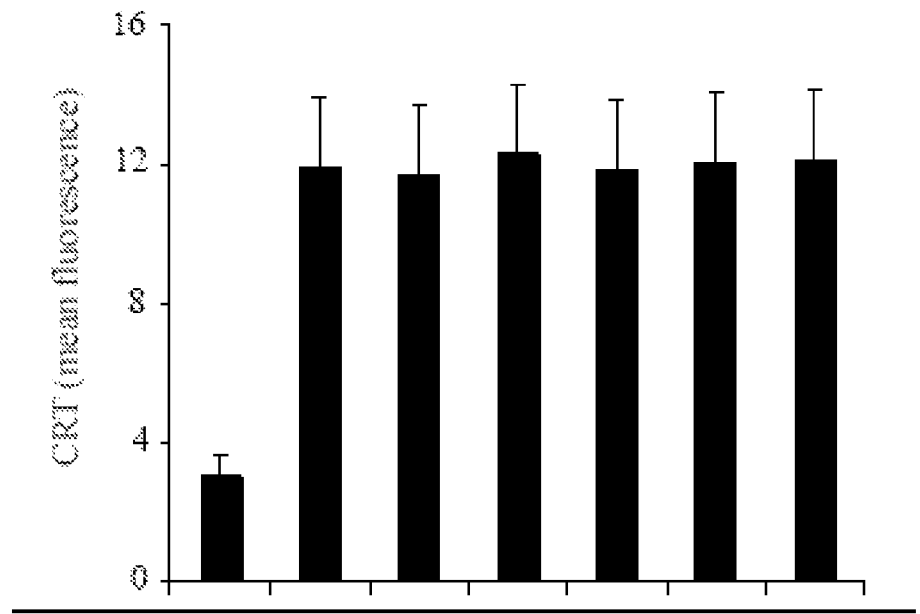
Figure 1S:
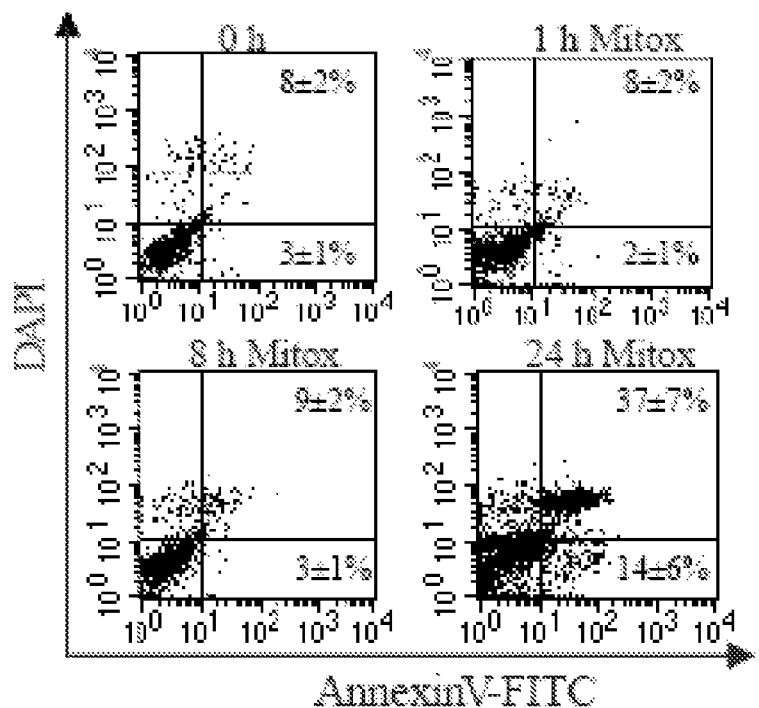
Figure 1S:
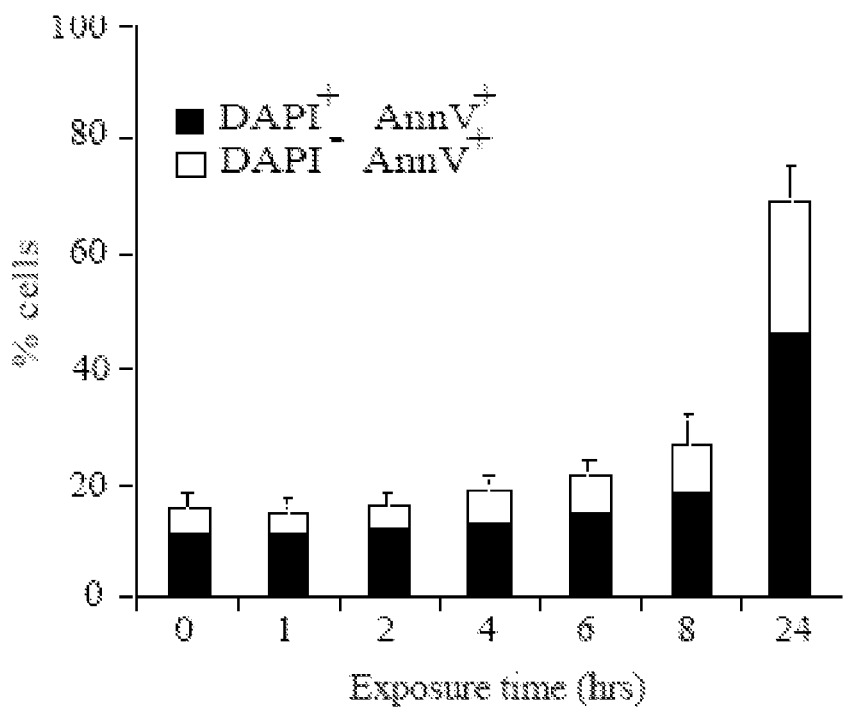

FIG. 1S. Dissociation of CRT exposure and phosphatidyl serine exposure.

FIG. 1SA, FIG. 1SB: Kinetics of CRT exposure. CT26 cells were treated with mitoxantrone for the indicated period, followed by immunofluorescence staining with a CRT-specific antibody and cytofluorometric analysis. Representative pictograms are shown in FIG. 1SA and quantitative data are reported in FIG. 1SB.

FIG. 1SC, FIG. 1SD: Kinetics of PS exposure and cell death. Cells were cultured as in FIG. 1SA and FIG. 1SB for the indicated period, followed by staining with Annexin V (which recognizes phosphatidylserin on the surface of dying cells) plus DAPI (which stains dead cells) and FACS analysis.

FIG. 2: CRT surface exposure in immunogenic cell death.

Figure 2C:
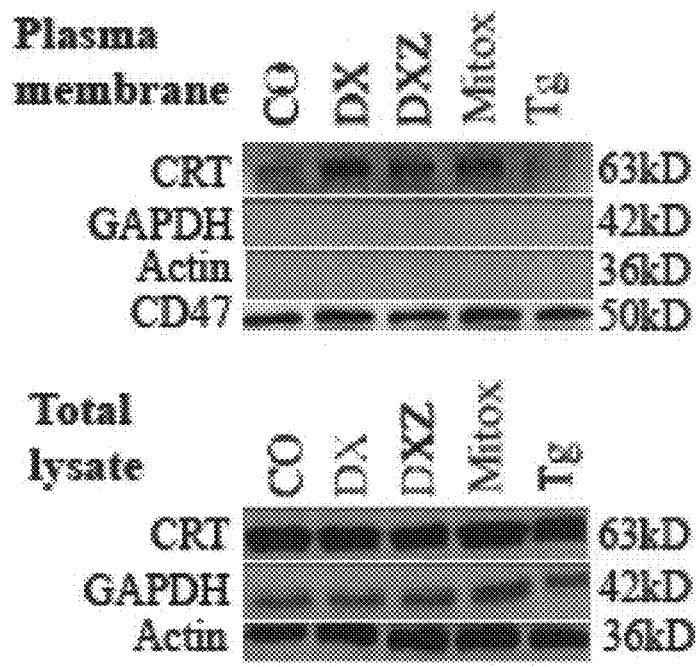
Figure 2D:
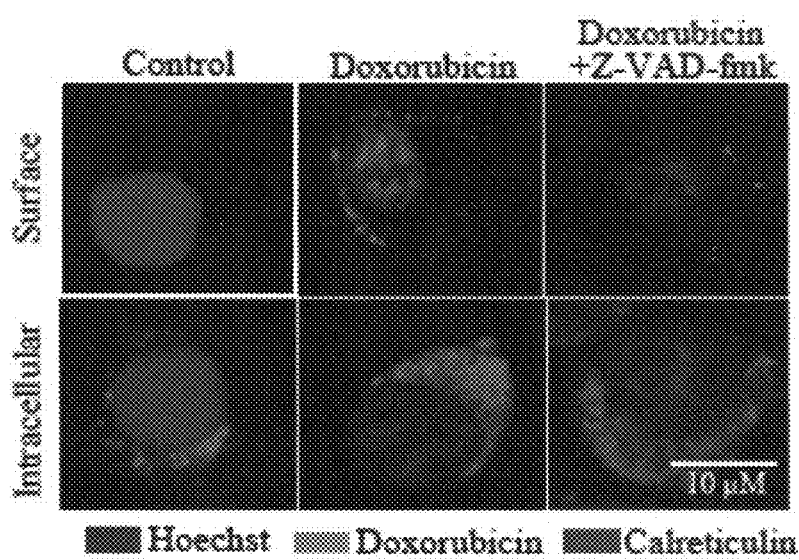

FIG. 2A-FIG. 2D: Identification of CRT as a surface-exposed molecule elicited by anthracycline. Cells were treated for 4 h with doxorubicin alone (DX) or in combination with Z-VAD-fmk (DXZ), followed by biotinylation of the cell surface and purification of biotinylated proteins, 2D gel electrophoresis (FIG. 2A and inserts in FIG. 2A showing part of the gel at higher magnification) and mass-spectroscopic identification of one doxorubicin-induced spot as CRT (arrows in FIG. 2A and underlined peptides in the CRT protein sequence in FIG. 2B, SEQ ID NO: 19), immunoblot detection of CRT in the plasma membrane protein fraction or the total cell lysate (FIG. 2C) or immunofluorescence detection of CRT on the cell surface (in non-permeabilized live cells) or within the cell (after permeabilization and fixation) (FIG. 2D). Note that the nuclei of untreated cells were visualized with Hoechst 33342 (blue), while those of doxorubicin-treated cells emit a red fluorescence (FIG. 2D). Circles in FIG. 2A indicate the position of ERP57.

Figure 2E:
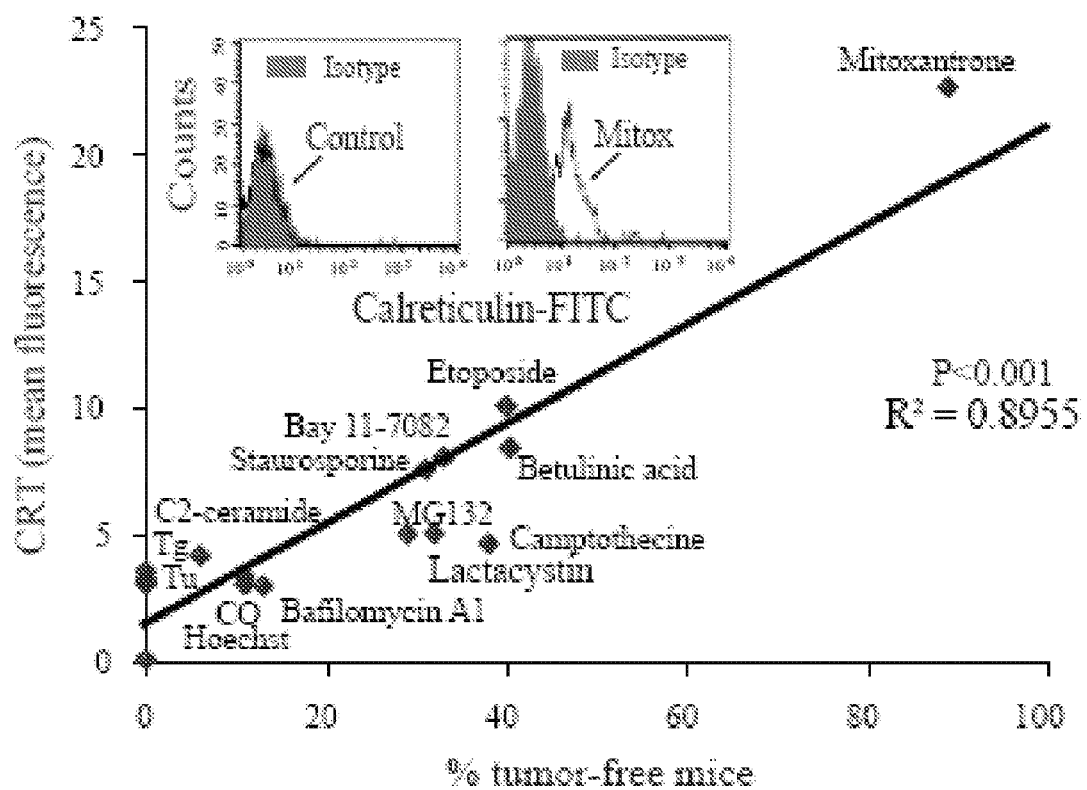

FIG. 2E: Correlation between CRT exposure and immunogenicity. The surface exposure of CRT was determined by immunofluorescence cytometry while gating on viable (propidium iodine-negative) cells (inserts) and was correlated with the immunogenicity of cell death (as determined in FIG. 1). CO, control; Tg, thapsigargin; Tu, tunicamycin.

FIG. 2S: FIG. 2S A, FIG. 2S B: Kinetics of phagocytosis and immunogenicity elicited by anthracyclins.

Figure 3A:
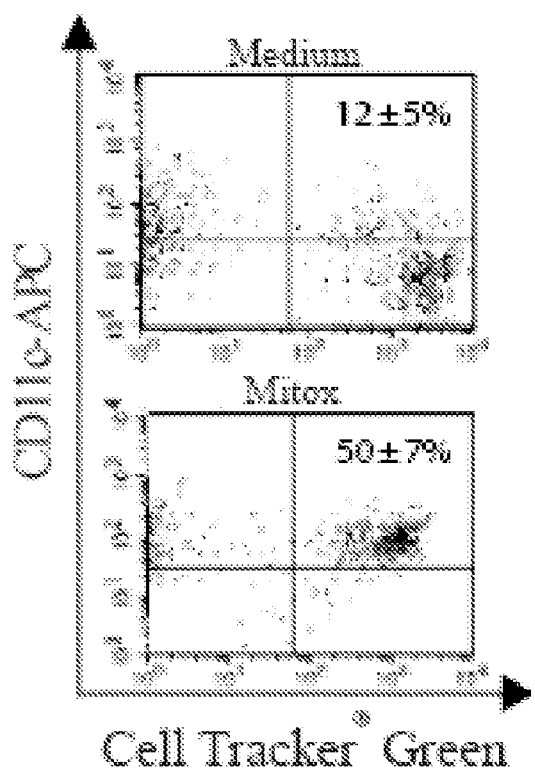

CT26 cells were cultured for different periods with mitoxantrone or doxorubicin and then confronted with DC to measure their phagocytosis (FIG. 2SA), as in FIG. 3A or injected into mice, one week before challenge with live cells (FIG. 2SB). Numbers on each column of FIG. 2SB indicate the number of mice that were immunized.

FIG. 3: Requirement of surface CRT for phagocytosis of tumour cells by DC.

Figure 3B:
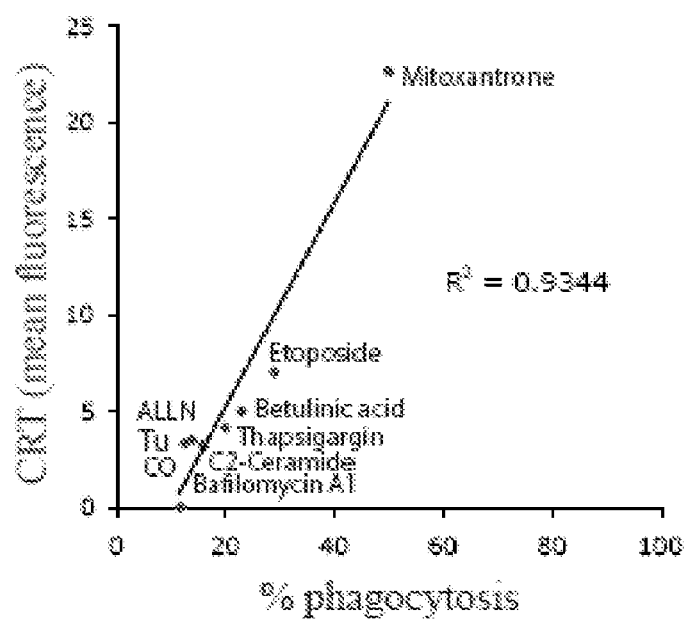

FIG. 3A, FIG. 3B: Correlation between tumour cell phagocytosis and CRT exposure. Tumour cells labelled with Cell Tracker Green were cultured with CD11c-expressing DC and the percentage of DC taking up tumour cells was determined (A) and correlated with the CRT surface exposure (B), measured as in FIG. 2E.

Figure 3C:
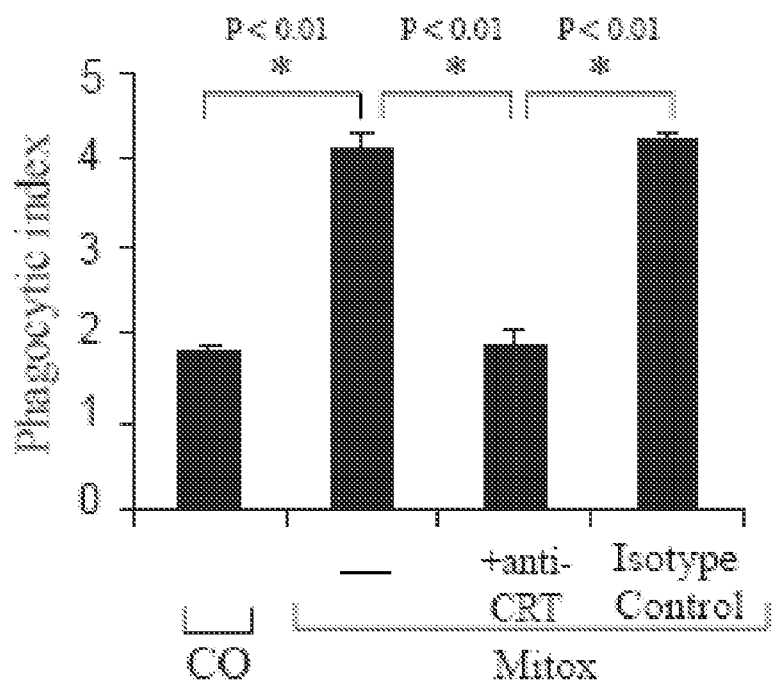

FIG. 3C: Blockade of CRT inhibits DC-mediated phagocytosis. Mitoxantrone-treated or control cells were incubated with a blocking chicken anti-CRT antibody, followed by detection of phagocytosis by CD.

Figure 3D:
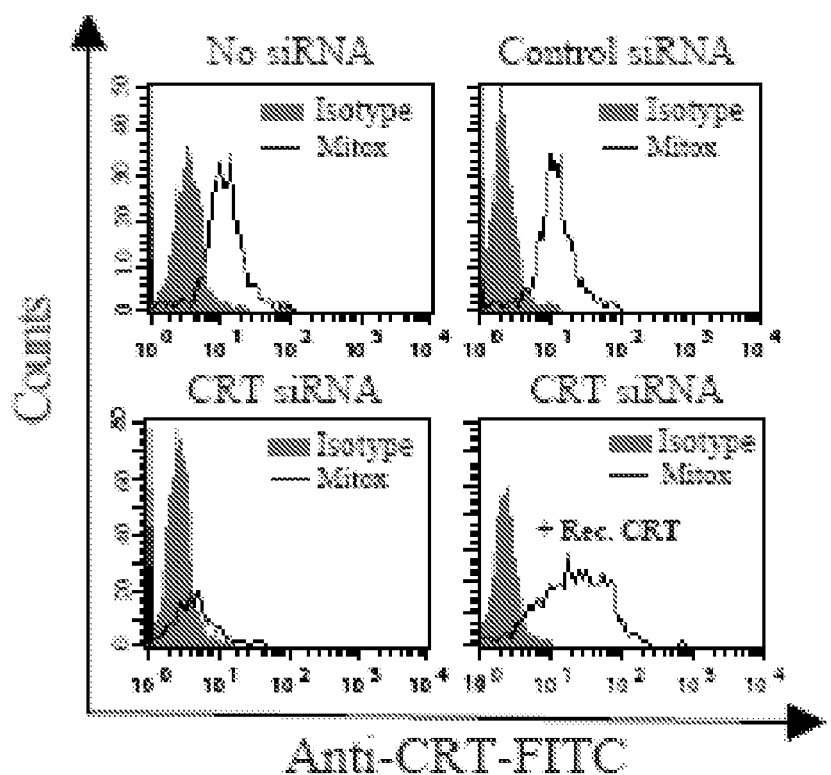
Figure 3E:
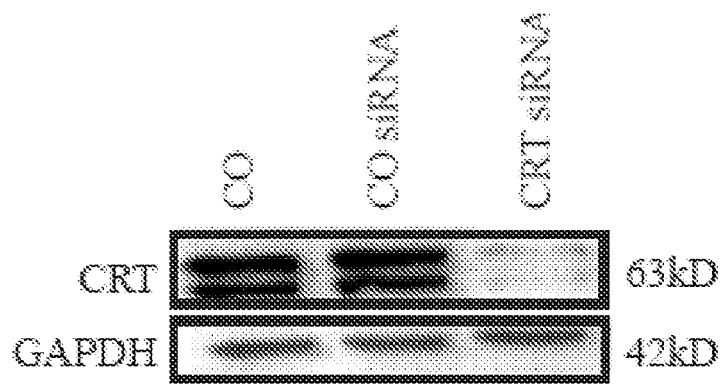
Figure 3F:
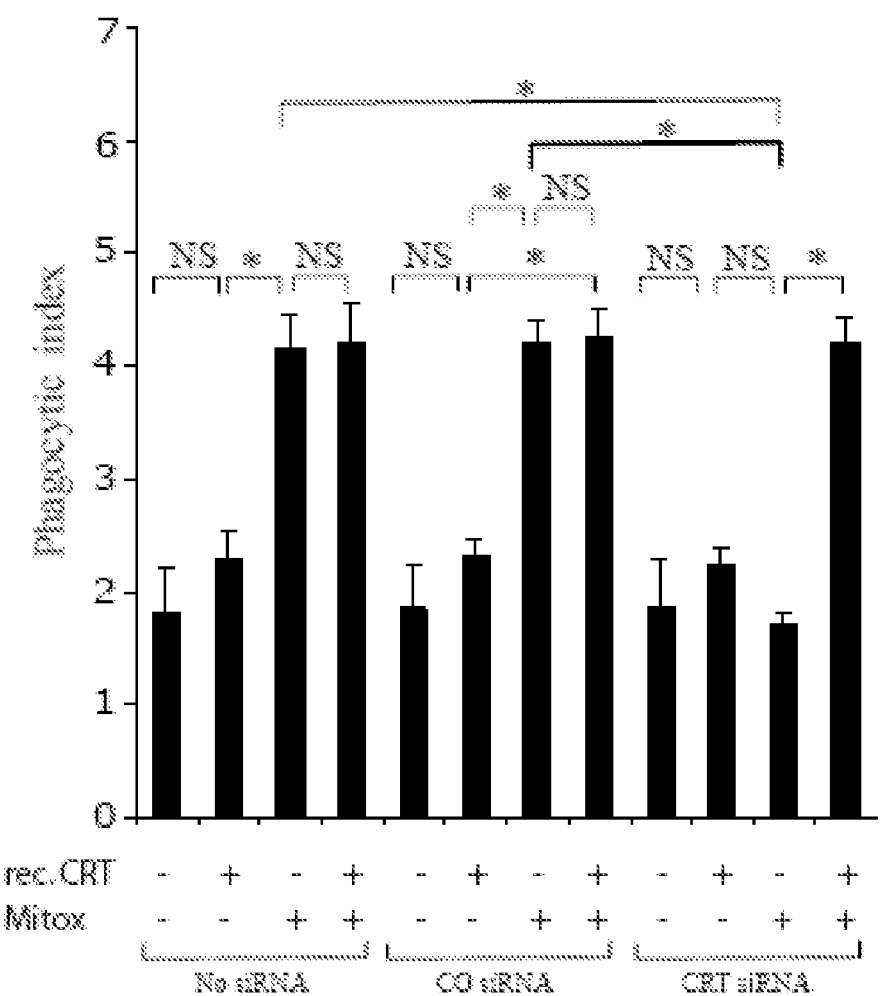

FIG. 3D, FIG. 3E, FIG. 3F: Knock-down of CRT inhibits DC-mediated phagocytosis and rCRT restores phagocytosis. Cells were transfected with the indicated siRNAs and optionally treated with rCRT, followed by immunoblot (FIG. 3D) detection of surface CRT (FIG. 3E) and phagocytosis by DC (FIG. 3F). Results are triplicates (X±SD) and representative of three independent experiments. * denotes statistically significant differences using the Student t' test at $p<0.001$.

Figure 3S:
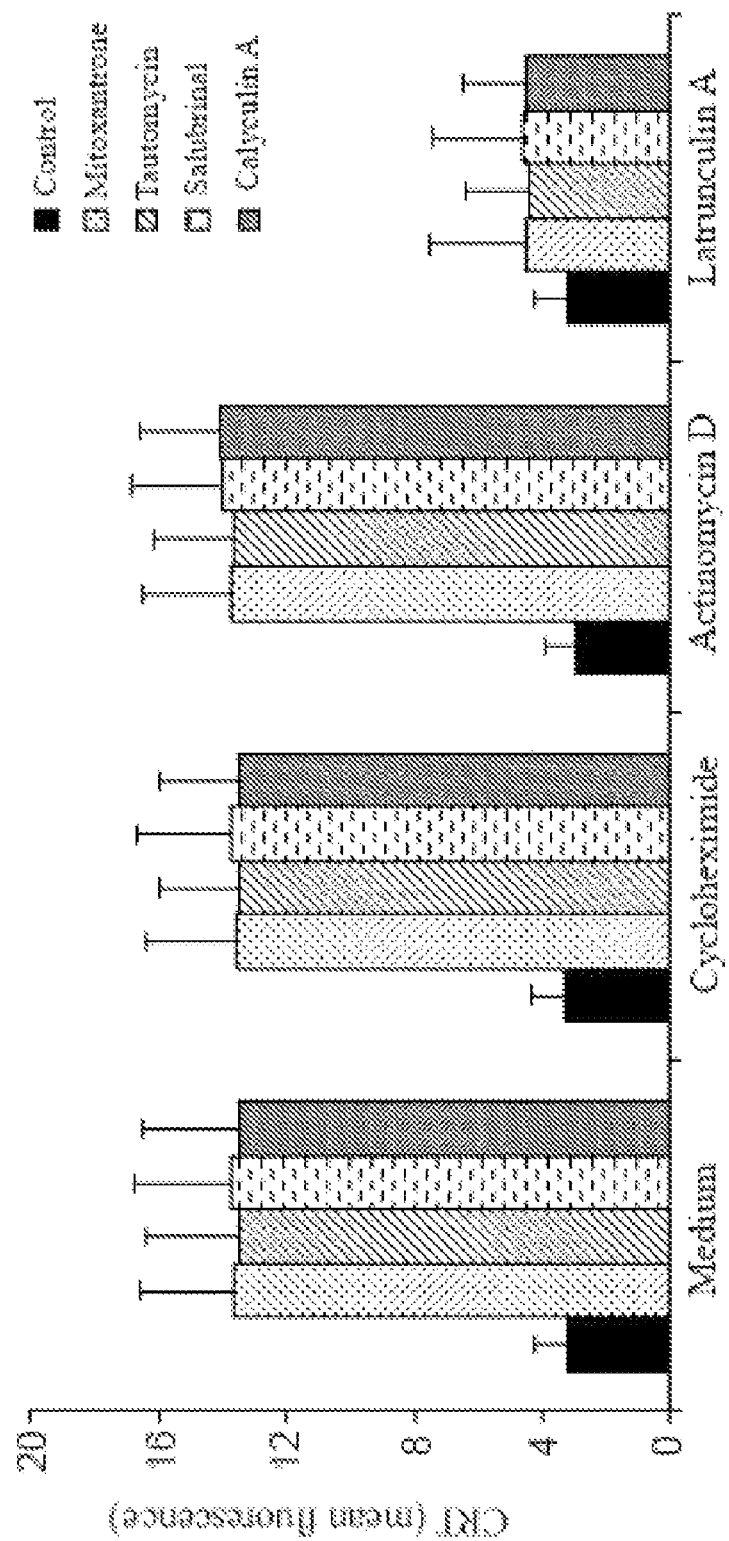

FIG. 3S: Inhibitory profile of CRT exposure. Cells were treated with mitoxantrone or inhibitors of PP1/GADD34, after pre-incubation for 1 h with the indicated inhibitors of protein synthesis (cycloheximide), RNA synthesis (actinomycin D), microtubuli (nocodazol), or the actin cytoskeleton (latrunculin A). Then, CRT expression was determined by immunocytofluorometry. Results are means of triplicates±SD for one representative experiment out of three.

FIG. 4: CRT is required for the immune response against dying tumour cells.

Figure 4A:
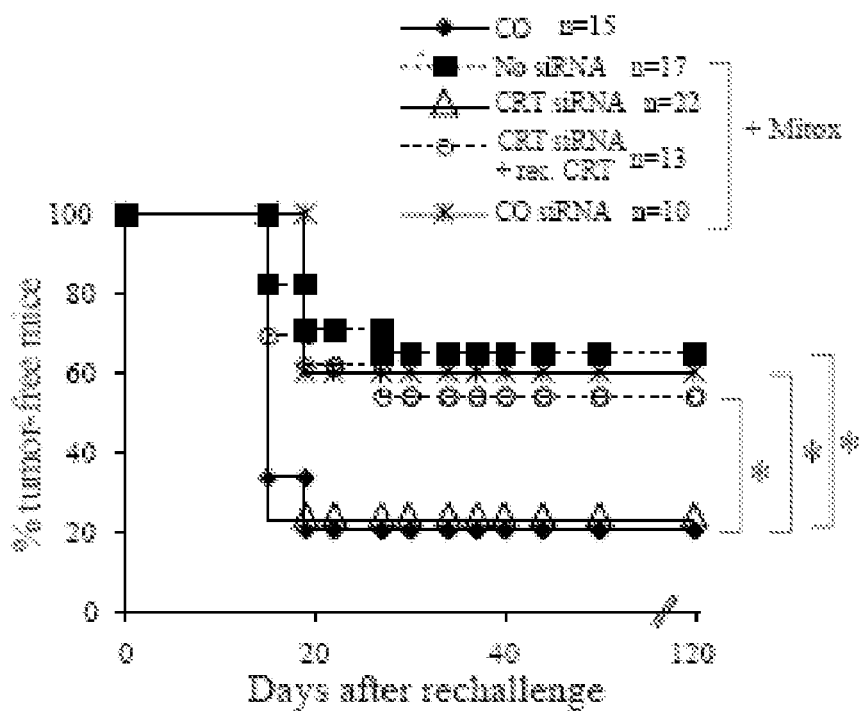

FIG. 4A: In vivo anti-cancer vaccination depends on CRT. CT26 colon cancer cells were transfected with the indicated siRNAs, then treated with rCRT and/or mitoxantrone (as in FIG. 3D) and the anti-tumour response was measured by simultaneously challenging BALB/c mice with mitoxantrone treated tumour cells in one flank and untreated live tumour cells in the opposite flank.

Figure 4B:
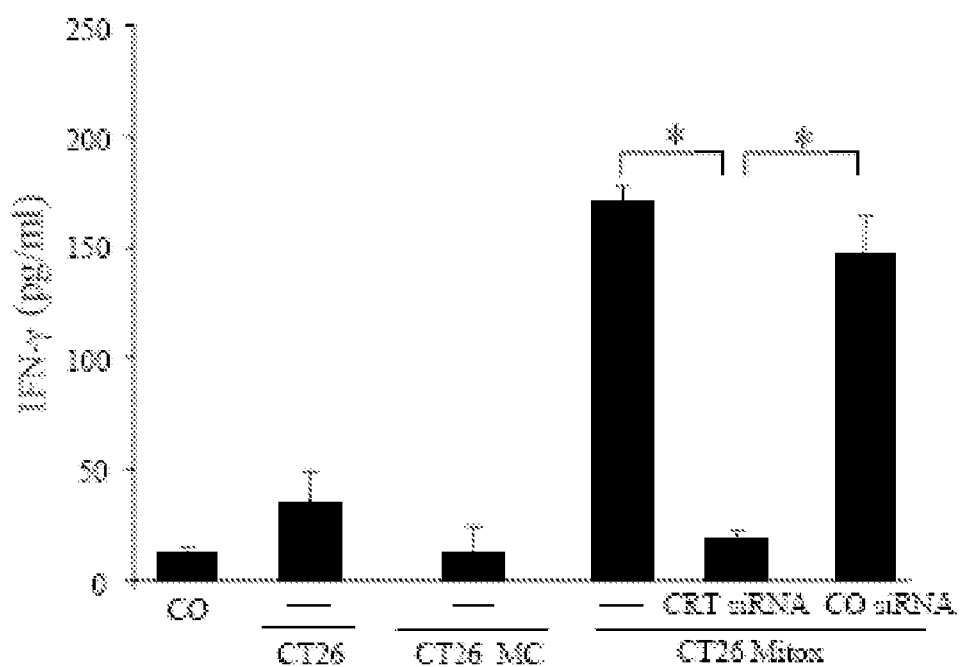

FIG. 4B: Priming of T cell responses depending on CRT. CT26 tumour cells were left untransfected or transfected with the indicated siRNAs, then treated with medium alone, mitomycin C or mitoxantrone and injected into the right food pad of Balb/c mice. Five days later, mononuclear cells from the draining popliteal lymph nodes were challenged with freeze-thawed CT26 cells, and IFN-γ secretion was assessed at 72 hrs.

Figure 4C:
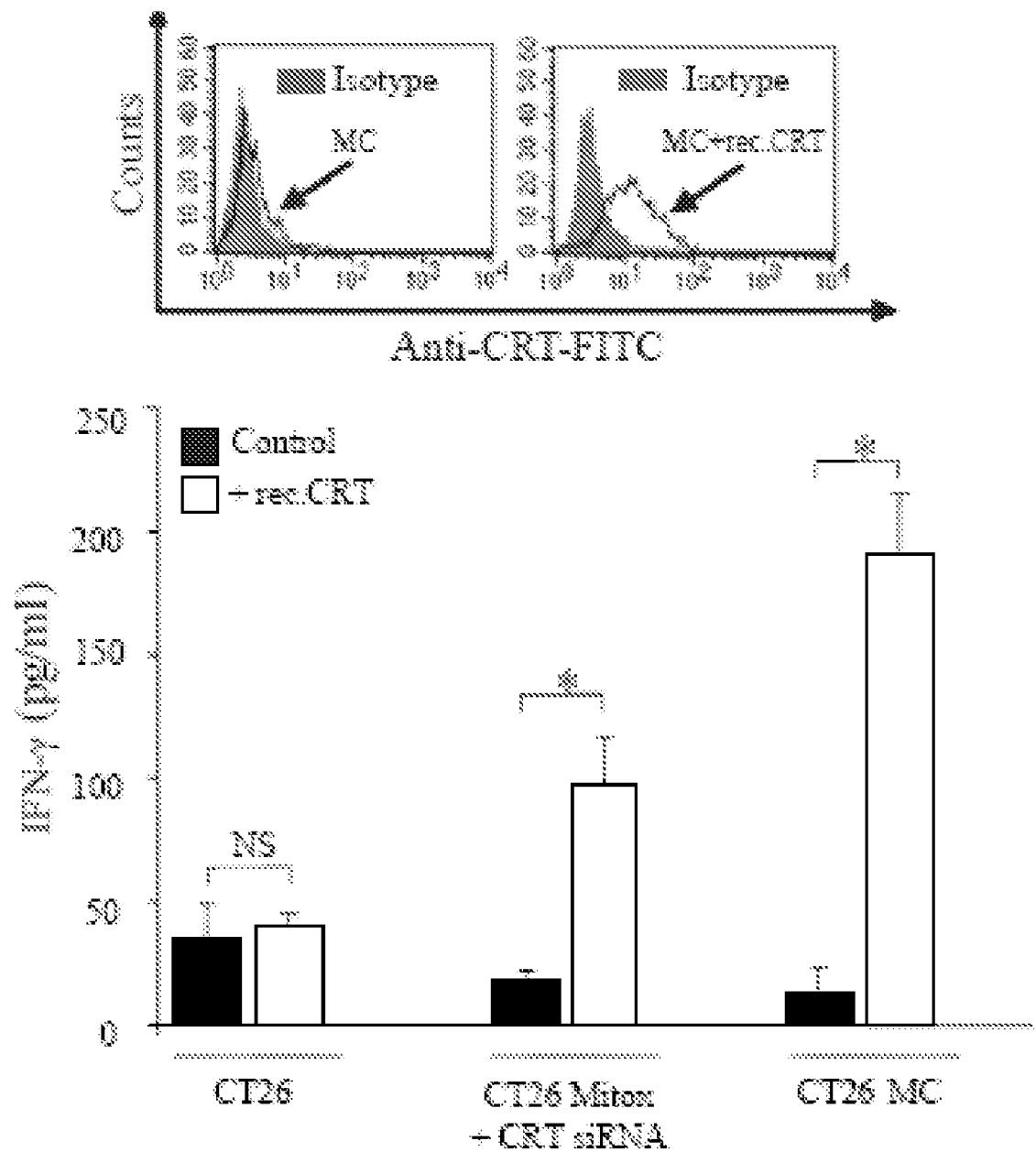

FIG. 4C: Exogenous supply of CRT enhances the immunogenicity of CRT-negative dying cells. CT26 cells lacking CRT expression after depletion of CRT with a siRNA and mitoxantrone treatment or after mitomycin treatment were coated with rCRT (inserts) and then injected in the food pad, followed by assessment of the IFN-γ secretion by cells from the draining lymph nodes as in FIG. 4B.

Figure 4D:
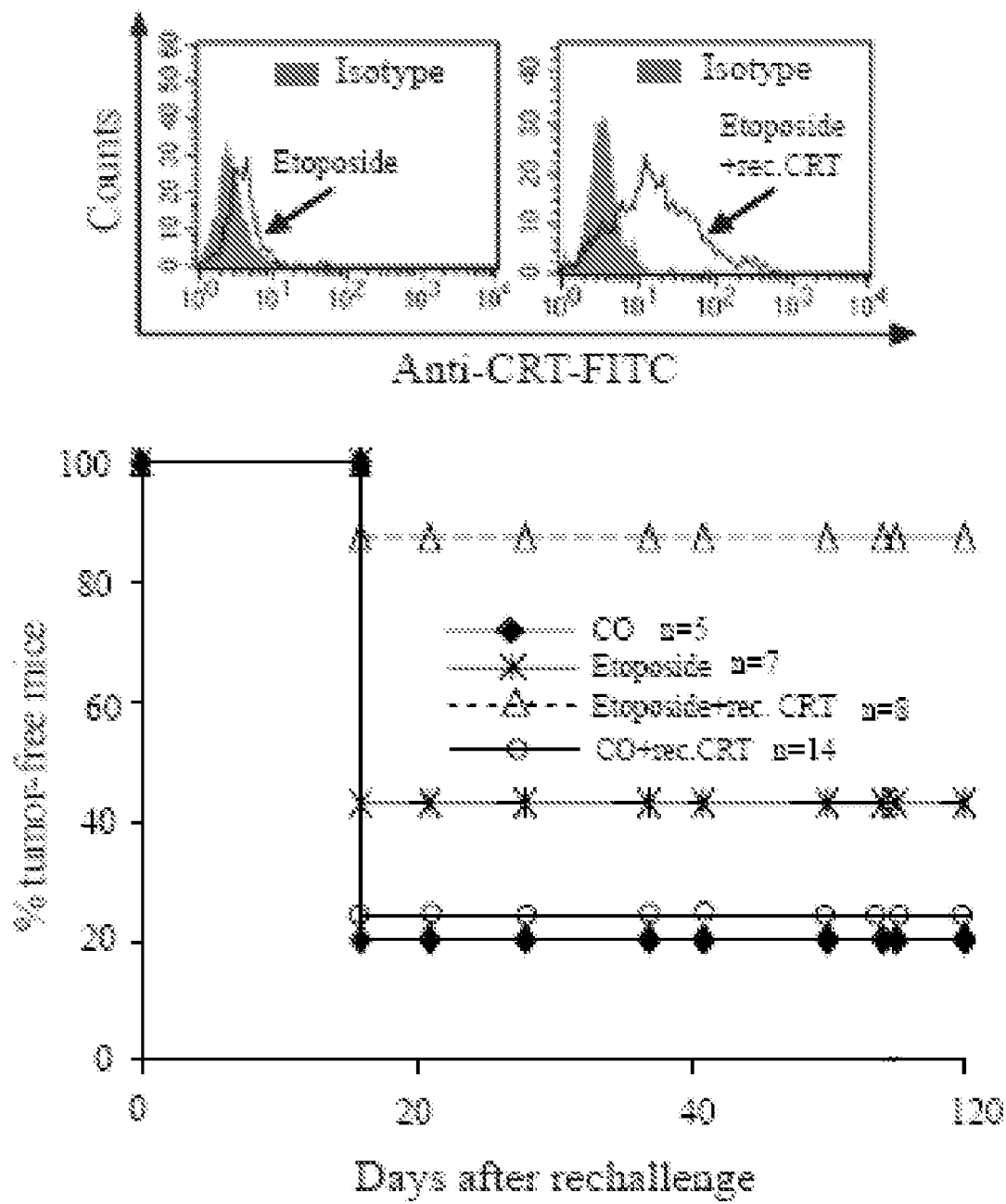

FIG. 4D: CRT-mediated amelioration of the immune response against etoposide-treated tumour cells. CT26 cells were treated for 24 h with etoposide (or PBS) and rCRT was optionally absorbed to the cell surface (inserts), followed by simultaneous injection of the etoposide ±rCRT-treated tumour cells and live tumour cells in opposite flanks and monitoring of tumour growth.

FIG. 5: Induction of calreticulin exposure and immunogenic cell death by inhibition of the PP1/GADD34 complex.

Figure 5A:
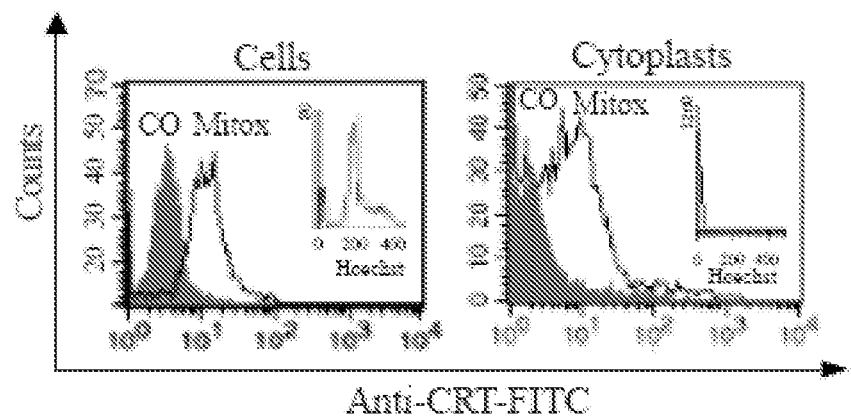

FIG. 5A: CRT exposure after anthracyclin treatment in the absence of a nucleus. Intact cells or enucleated cells (cytoplasts) were treated for 2 hours with mitoxantrone, followed by immunofluorescence detection of CRT exposure. Inserts show the effective removal of Hoechst 33342-stainable nuclei from the cytoplasts.

Figure 5B:
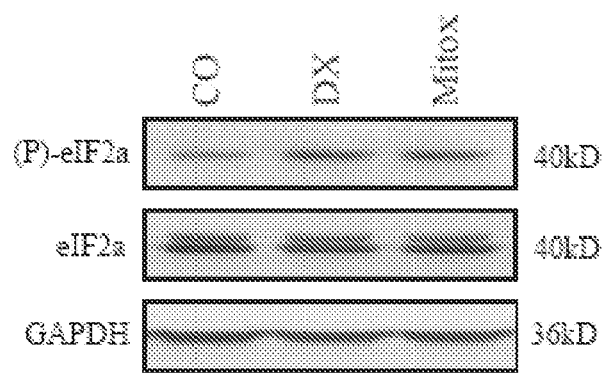

FIG. 5B: Phosphorylation of eIF2alpha after treatment with anthracyclins. Cells were treated for four hours with mitoxantrone or doxorubicine followed by immunoblot detection of phosphorylated eIF2alpha irrespective of its phosphorylation state and GAPDH as a loading control.

Figure 5C:
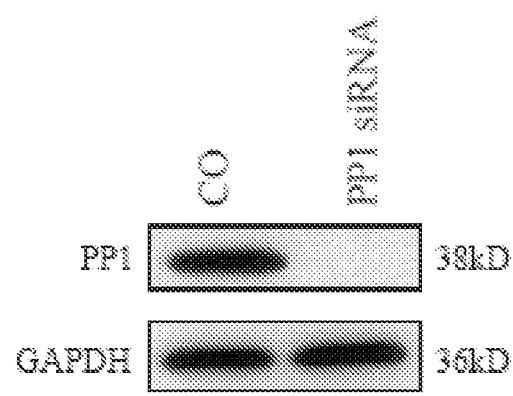
Figure 5D:
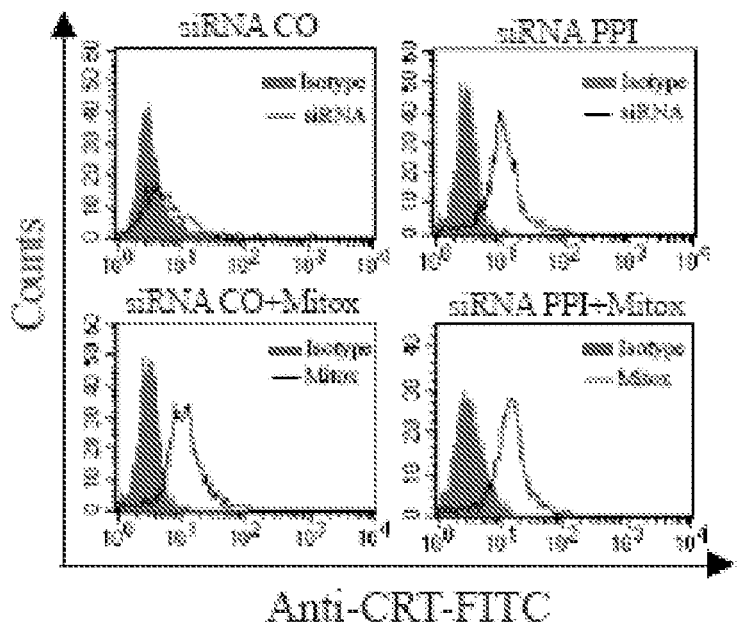

FIG. 5C-FIG. 5D: Induction of CRT exposure by knockdown of PP1. Cells were transfected with siRNAs specific for the indicated transcripts and were treated 36 h later for 2 h with mitoxantrone prior to immunoblot (FIG. 5C) and cell surface staining (FIG. 5D).

Figure 5E:
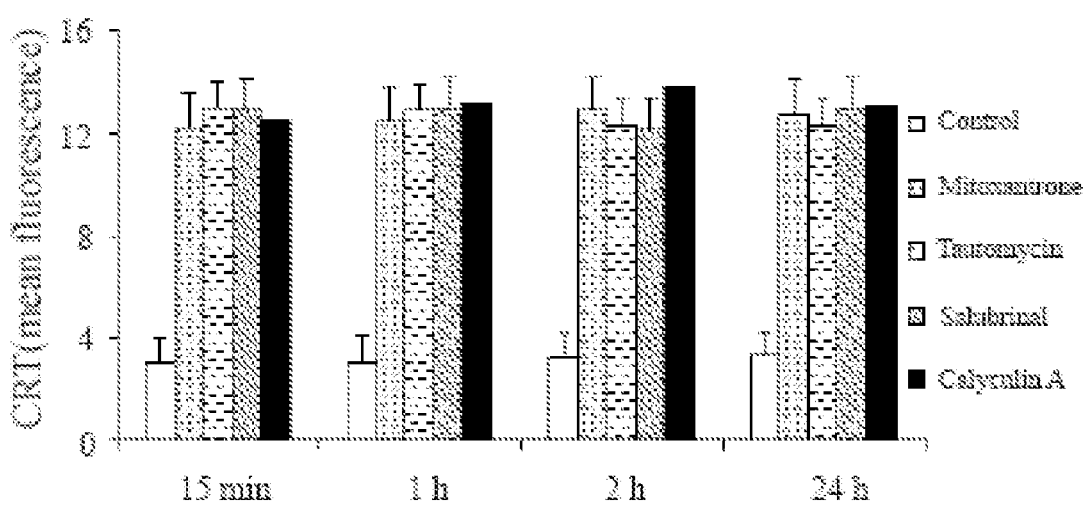

FIG. 5E: Kinetics of CRT exposure determined by FACS analysis after incubation of cells with the indicated agents.

Figure 5F:
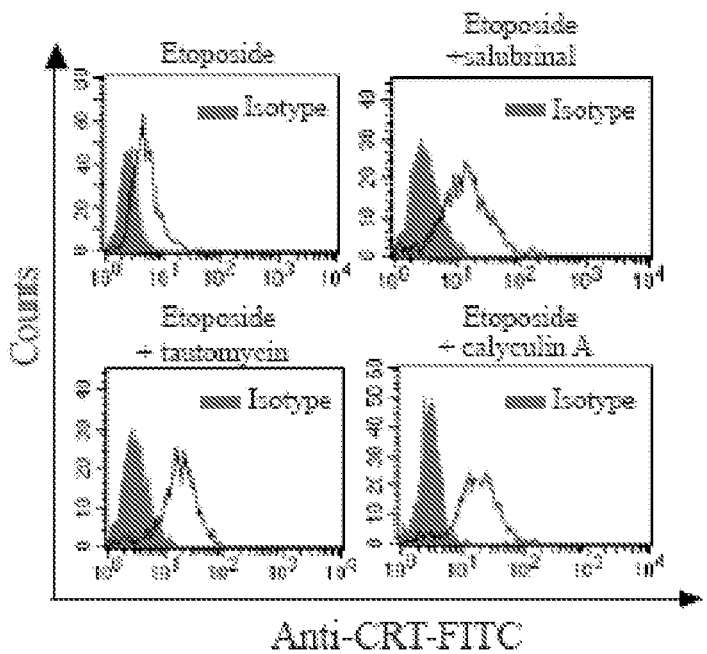
Figure 5G:
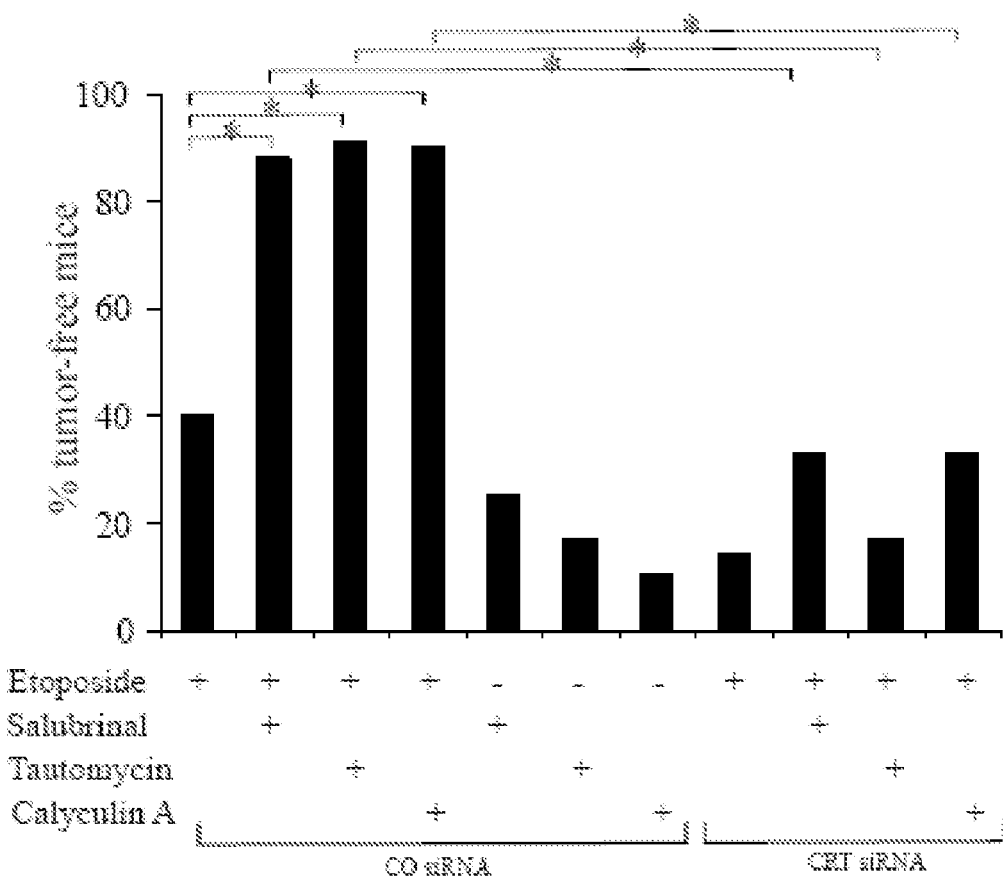

FIG. 5F-FIG. 5G: PP1/GADD34 inhibitors render cell immunogenic via CRT. Tumour cells were first transfected with a control siRNA or a CRT-specific siRNA and then treated in vitro with etoposide, alone or in combination with PP1/GADD34 inhibitors. Two hours later, the surface CRT was detected to demonstrate the effective expression of CRT on control siRNA-transfected cells treated with etoposide alone or etoposide plus PP1/GADD34 inhibitors (FIG. 5F), and later, the cells were injected as in FIG. 1A to determine their capacity to inhibit the growth of live tumour cells inoculated one week later (FIG. 5G). The results represent the % of tumour free mice (comprising a total of 12 to 18 mice per group).

Figure 6A:
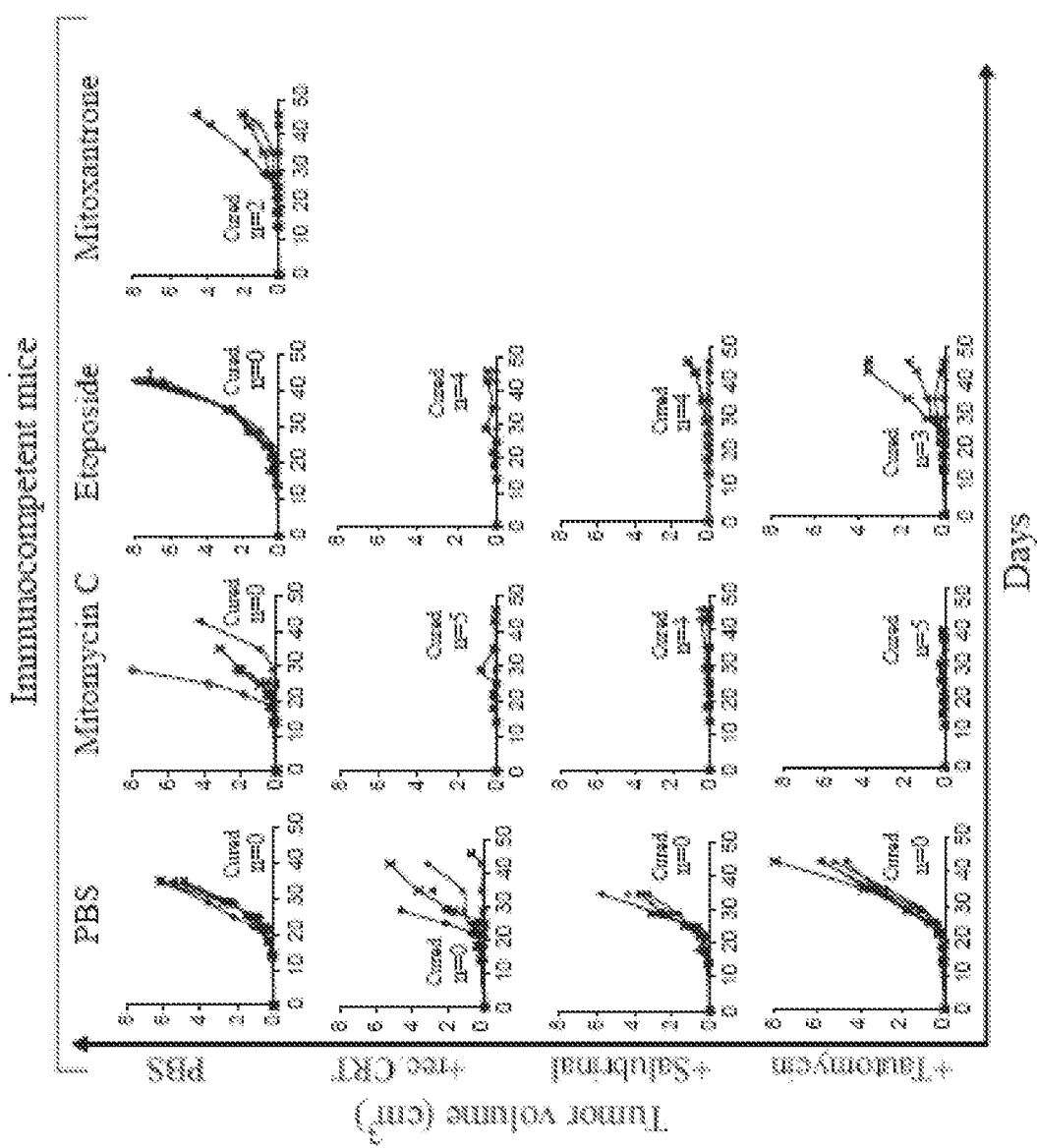
Figure 6B:
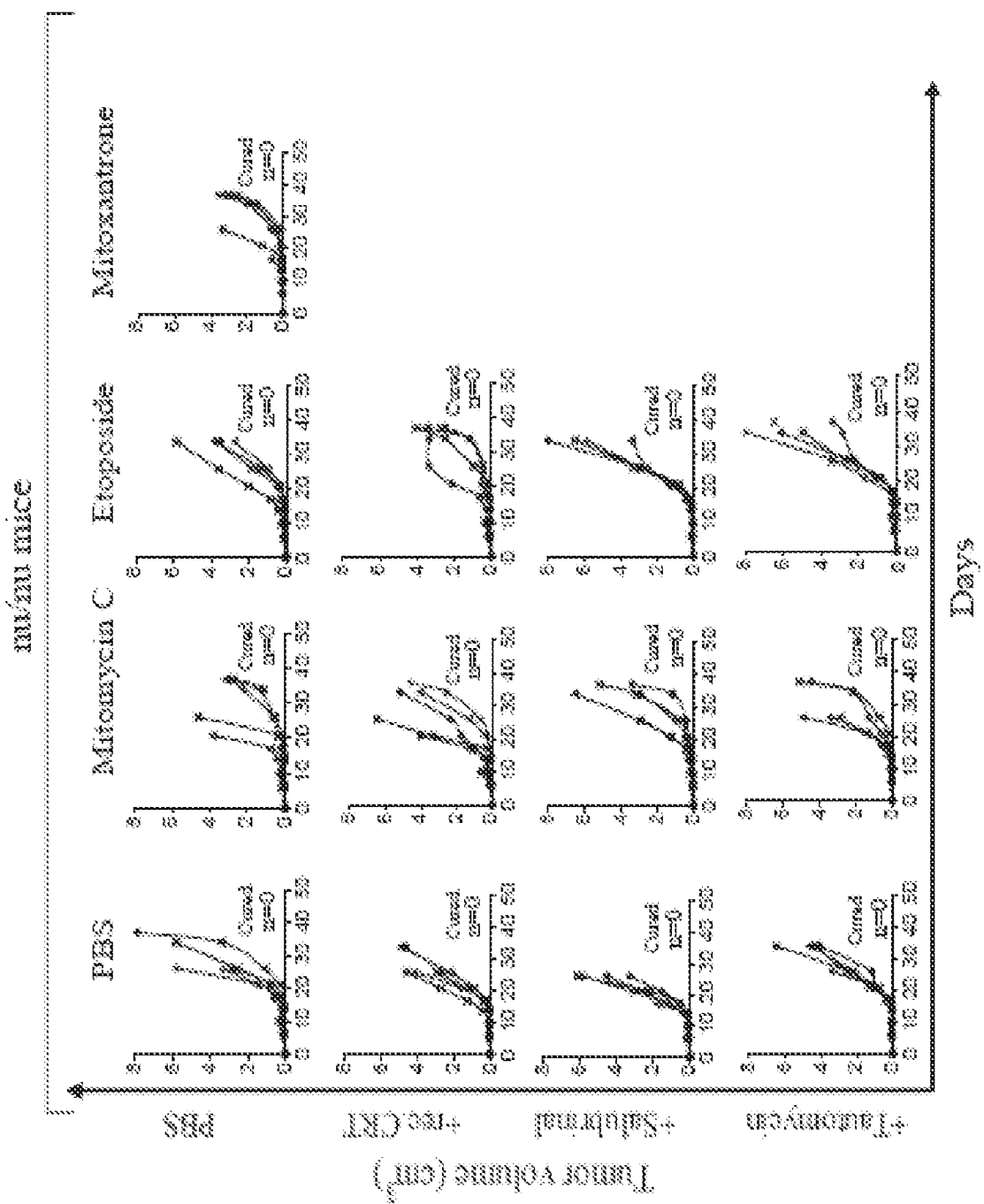
Figure 6C:
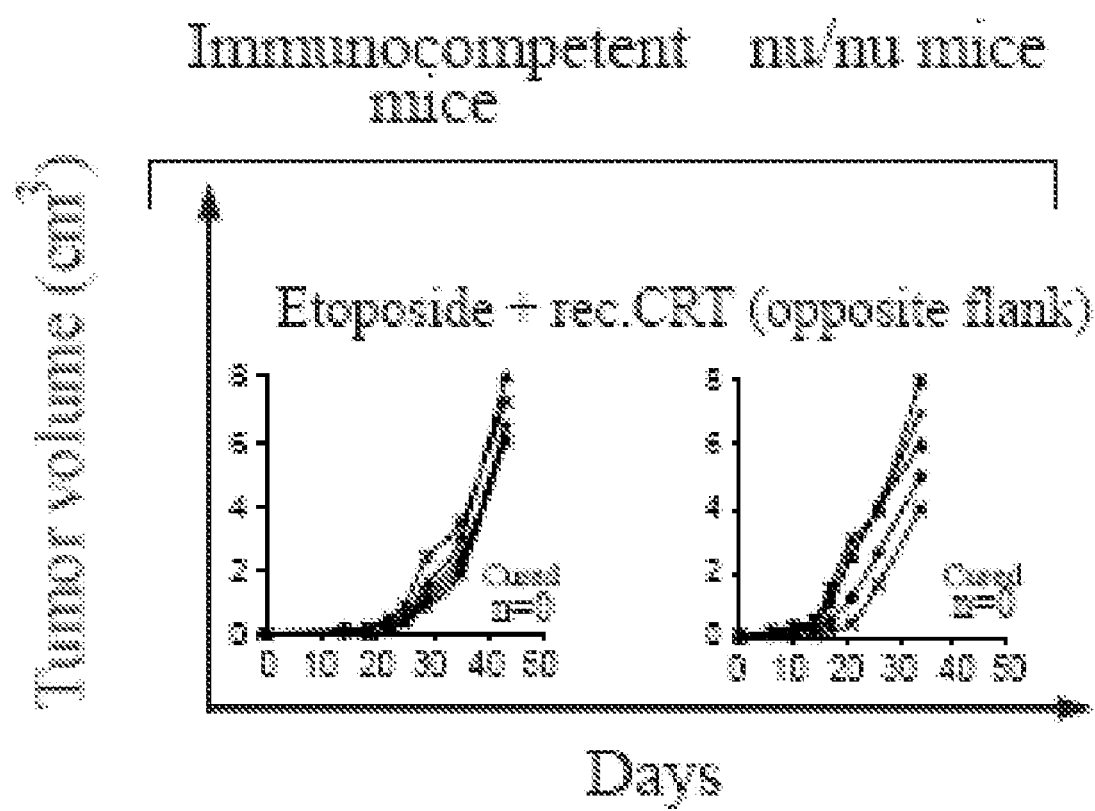

FIG. 6: FIG. 6A, FIG. 6B, FIG. 6C, Therapeutic effect of CRT or PP1/GADD34 inhibitors injected into tumours.

CT26 tumours established in immunocompetent wild type (FIG. 6A) or athymic nu/nu Balb/c mice (FIG. 6B) were injected locally with the indicated combinations of mitoxantrone, etoposide, mitomycin C, rCRT, salubrinal or tautomycin, followed by monitoring of tumour growth. Each curve represents one mouse. Numbers in the lower right corner of each graph indicate the number of mice that manifest complete tumour involution at day 45. FIG. 6C. Identical experimental setting using intratumoural etoposide plus contralateral subcutaneous injection of rec.CRT. The graphs depict one representative experiment out of two, comprising 5 mice/group.

Figure 7A:
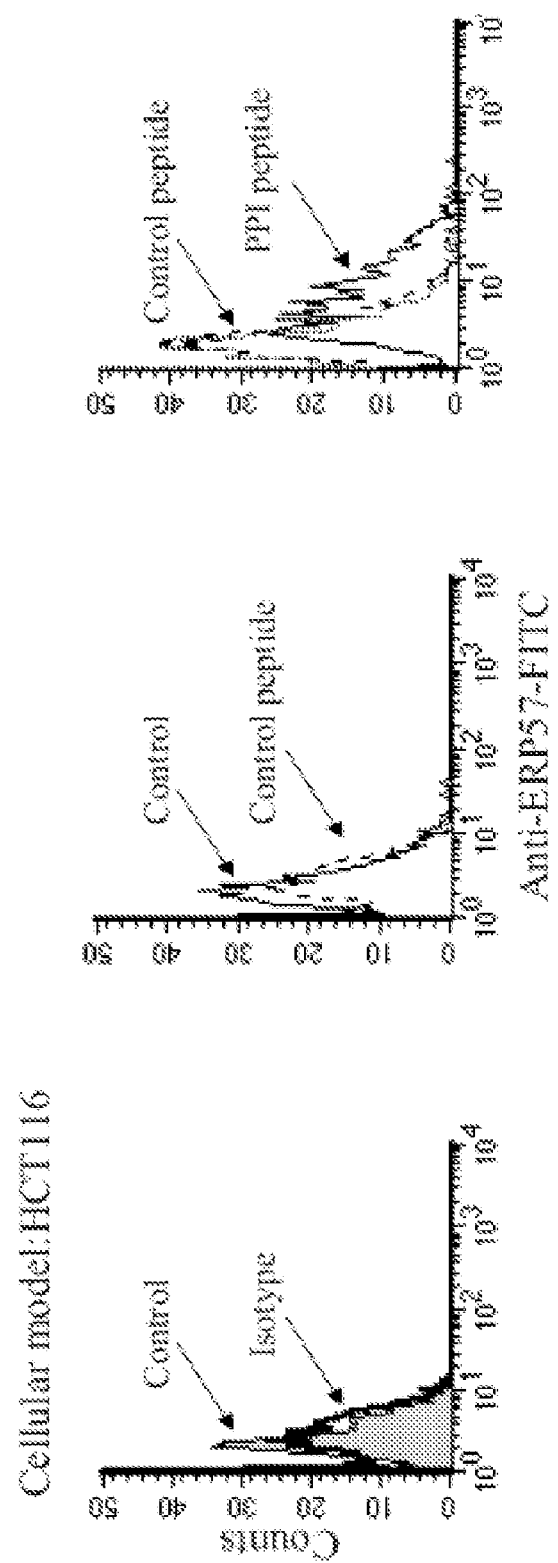
Figure 7B:
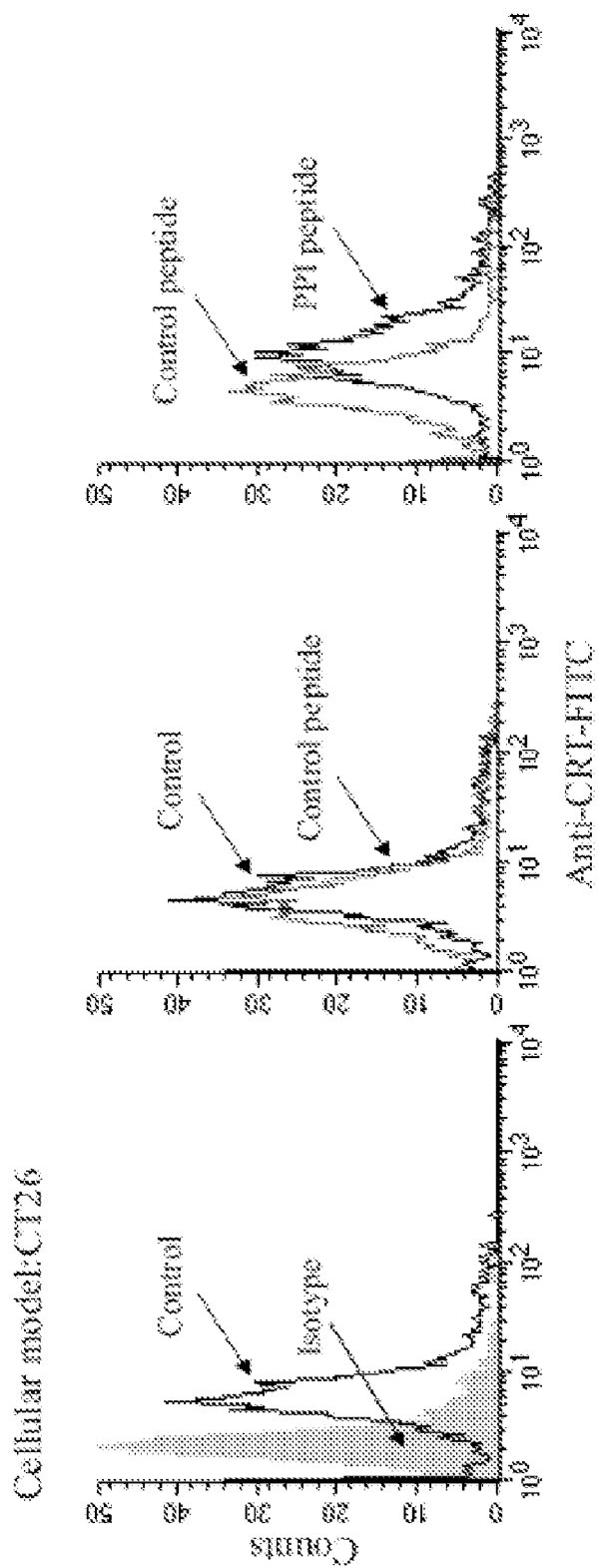

FIG. 7: FIG. 7A, FIG. 7B; Expression of ERp57/CRT in the presence or absence of a PP1/GADD34 inhibitory peptide.

HCT116 cells (FIG. 7A) or CT26 cells (FIG. 7B) were cultured in complete mediums supplemented with 10% fetal calf serum alone or in the presence of the control peptide (VKKKKIKREIKI-lkaravafsekv) (SEQ ID NO: 17) or the PP1/GADD34 inhibitory peptide (VKKKKIKREIKI-lkarkvrfsekv, SEQ ID NO: 4. denominated PP1 peptide) for 2 hours. Cells were washed twice with PBS and fixed in PFA (4% w/v) for 5 min. Cells were stained with an antibody against calreticulin (pAb from Abeam, ab2907) at 1:200 dilution or isotype control, in staining buffer (PBS, 1% FCS) for 30 min on ice, followed by washing. An anti-rabbit Alexa fluor 488 immunoglobulin conjugate (Molecular Probes-Invitrogen) diluted at 1:500 was added for an additional 30 min on ice before washing and analysed by flow cytometry (FACScan, Becton Dickinson). Propidium Iodide (50 µg/ml, Becton Dickinson) was added to the samples to label and exclude permeabilized (dead) cells.

Figure 8:
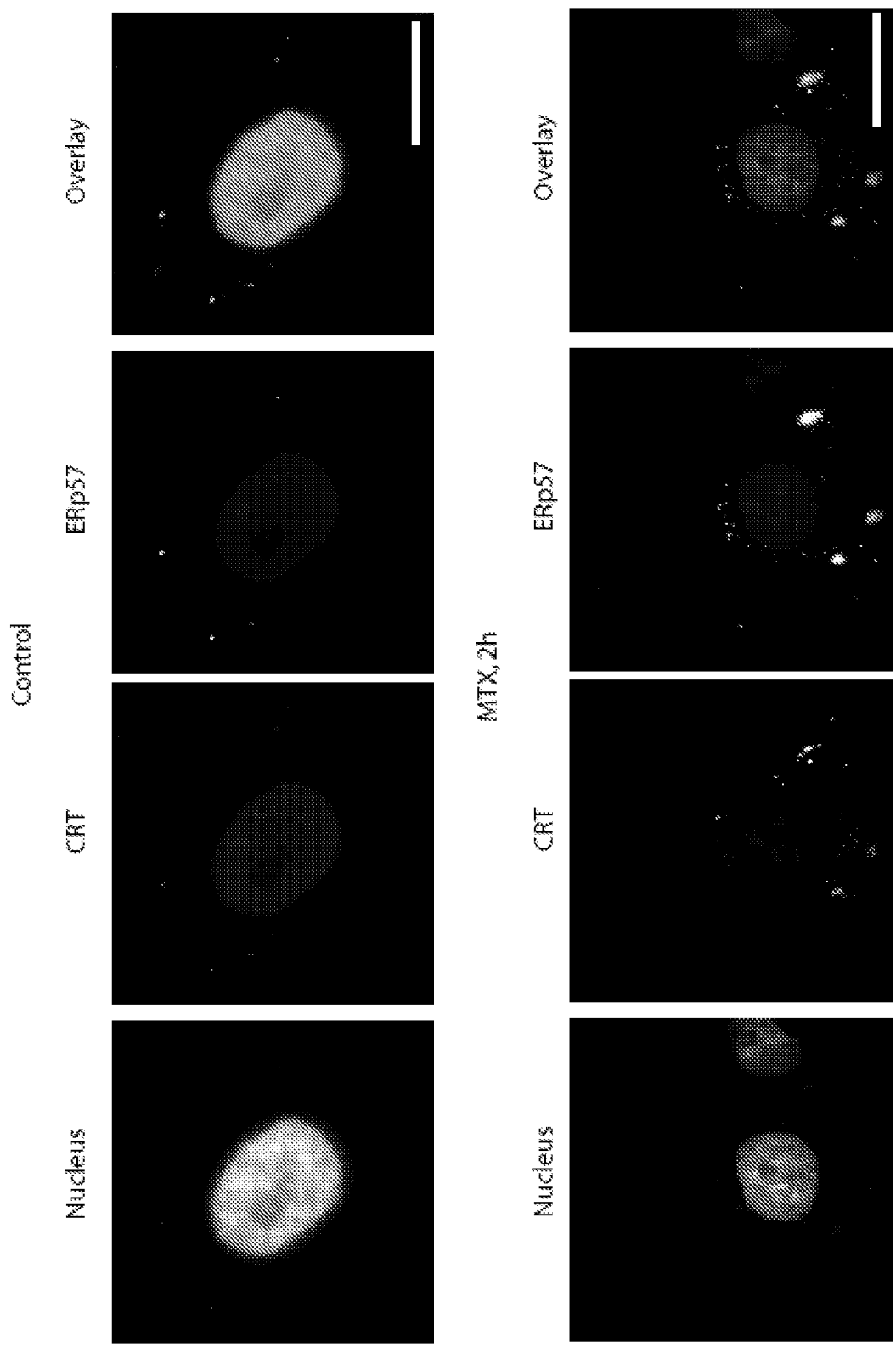

FIG. 8: Calreticulin and Erp57 co-localise on the surface of MTX-treated cells.

HeLa cells were cultured on cover slips and treated with or without 1 µM mitoxantrone (MTX) for two hours. HeLa Cells were stained for the detection of calreticulin (CRT) (mAb from Abcam, ab22683) and for ERp57 (pAb from Abcam, ab10827) revealed by goat anti-mouse Alexa fluor 568 and anti-rabbit Alexa fluor 488 immunoglobulin conjugates (Molecular Probes-Invitrogen). Nuclei were labelled with DAPI mounting medium (Vectashield). Fluorescence microscopy was analyzed with a Leica IRE2 equipped with a DC300F camera at 63× magnification. Size bars denote 10 µm.

Figure 9:
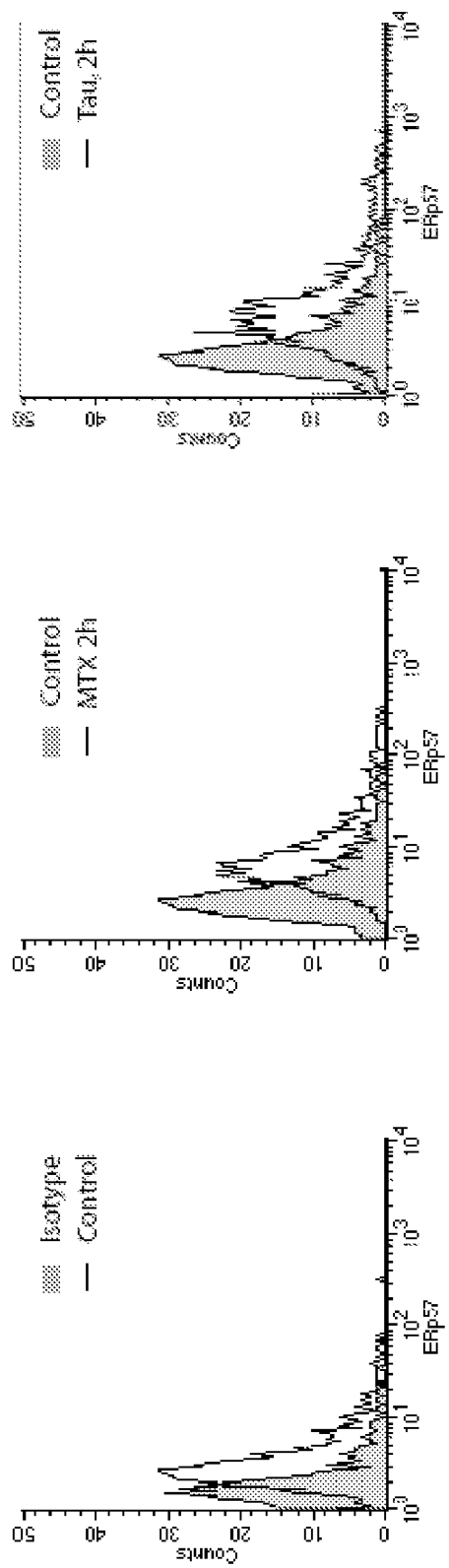

FIG. 9: Flow cytometric detection of Erp57.

HeLa cells were treated with or without mitoxantrone (MTX, 1 µM) or tautomycin (Tau, 150 nM, Sigma) for 2 h. Cells were washed twice with PBS and fixed in PFA (4% w/v) for 5 min. HeLa cells were stained with an antibody against Erp57 (pAb from Abcam, ab10827) at 1:200 dilution or isotype control, in staining buffer (PBS, 1% FCS) for 30 min on ice, followed by washing. An anti-rabbit Alexa fluor 488 immunoglobulin conjugate (Molecular Probes-Invitrogen) diluted at 1:500 was added for an additional 30 min on ice before washing and analysed by flow cytometry (FACScan, Becton Dickinson). Propidium Iodide (50 µg/ml, Becton Dickinson) was added to the samples to label and exclude permeabilized (dead) cells. The CellQuest software was used to analyse the mean fluorescence intensity (MFI) and the percentage of ERp57 positive cells.

FIG. 10: Immunofluorescence and confocal microscopy analysis of KDEL receptor on HeLa cells treated with anthracyclins.

Figure 10A:
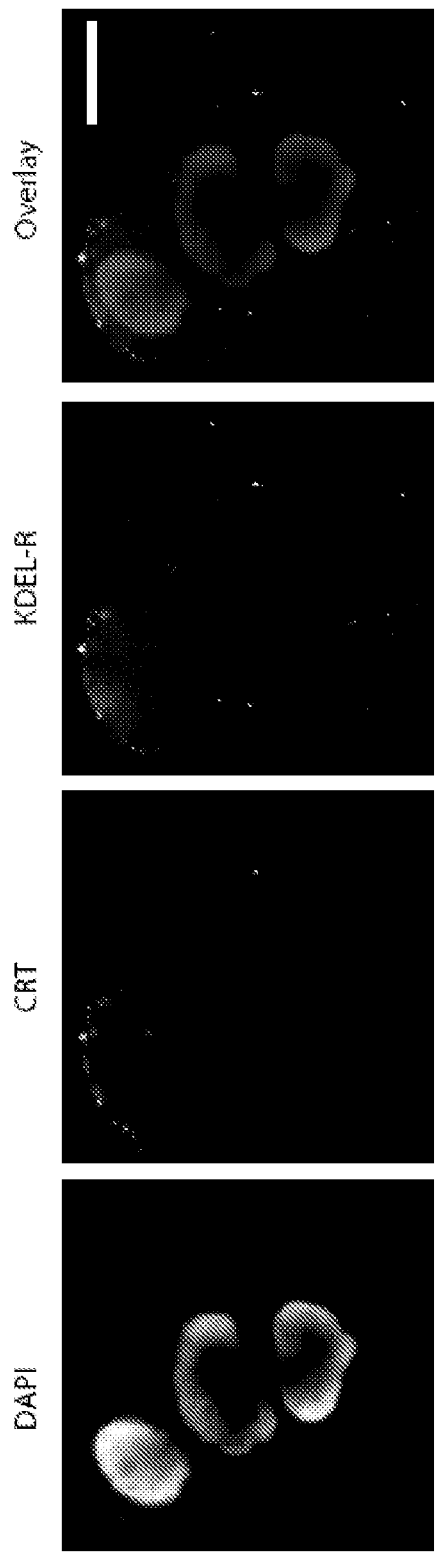
Figure 10B:
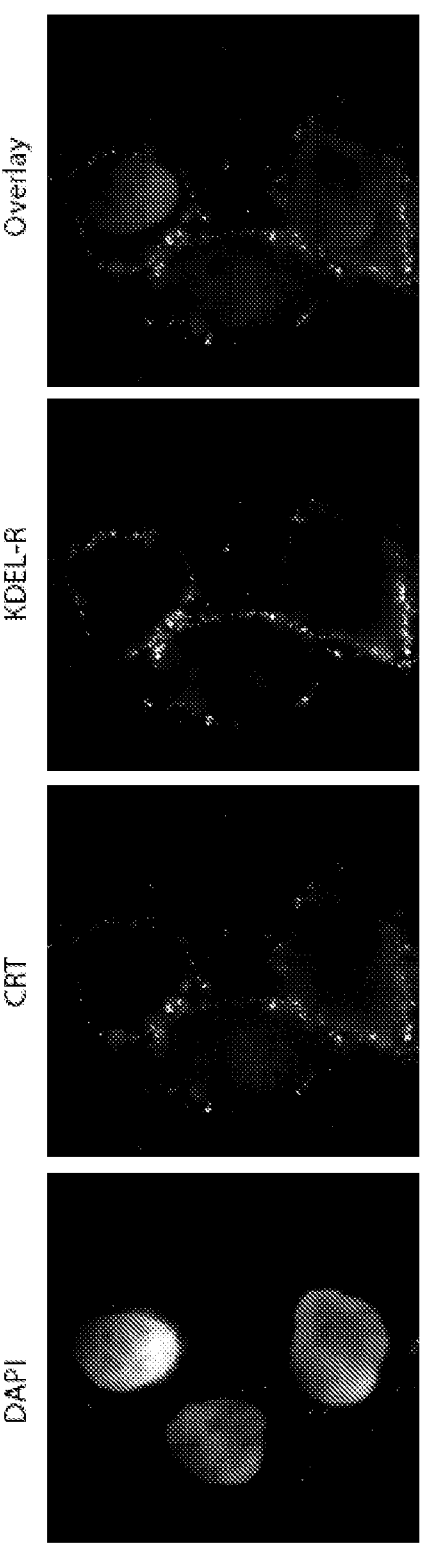

FIG. 10(A) Control and FIG. 10(B) MTX treated HeLa cells HeLa cells were cultured on cover slips and treated without (A) or with (B)1 µM mitoxantrone (MTX, Sigma) for 2 h. Cells were fixed with Paraformadehyde (4% w/v) on ice for 5 min. Cells were stained for the detection of KDEL-Receptor (KDEL-R) (mAb from Abcam, ab12224) and CRT (pAb from Abcam, ab2907) by goat anti-mouse Alexa fluor 568 and anti-rabbit Alexa fluor 488 immunoglobulin conjugates (Molecular Probes-Invitrogen). Nuclei were labelled with DAPI mounting medium (Vectashield). Fluorescence microscopy was analyzed with a Leica IRE2 equipped with a DC300F camera. Size bars: 10 µm.

Figure 11:
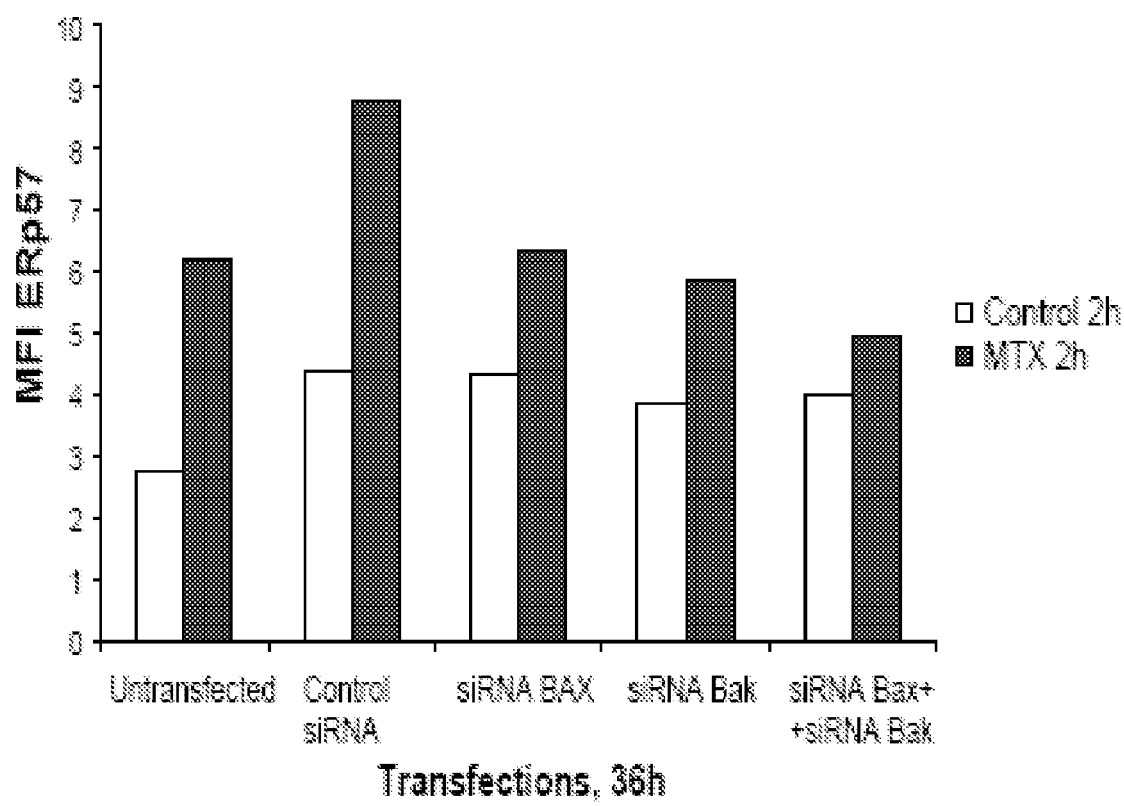

FIG. 11: Requirement of Bax and Bak for the exposure of ERp57.

HeLa cells were cultured in 24-well plates and transfected at 80% confluence with Oligofectamine reagent (Invitrogen), in the presence of 20 nM of siRNAs specific for human Bax (sense 5'-GGUGCCGGAACUGAUCAGATT-3'—SEQ ID NO: 5, anti-sense: 5'UCUGAUCAGUUCCGGCACCTT-3'—SEQ ID NO: 6) and/or Bak (sense, 5'-ACCGACGCKAT-GACTCAGAGTTC-3'—SEQ ID NO: 7, anti-sense, 5'-ACACGGCACCAATTGATG-3'—SEQ ID NO: 8) and an irrelevant sequence (sense 5'-GCCGGUAUGCCGG-UUAAGU-3'—SEQ ID NO: 9, anti-sense: 5'-ACUUAAC-CGGCAUACCGGC-3'—SEQ ID NO: 10) as a control. siRNA effects were controlled by immunoblots with suitable antibodies specific for Bax and Bak. Following 36 h of transfection, the cells were treated with MTX (1 µM) for 2 h. The MFI of surface Erp57 positive cells was analysed as described in FIG. 9.

Figure 12:
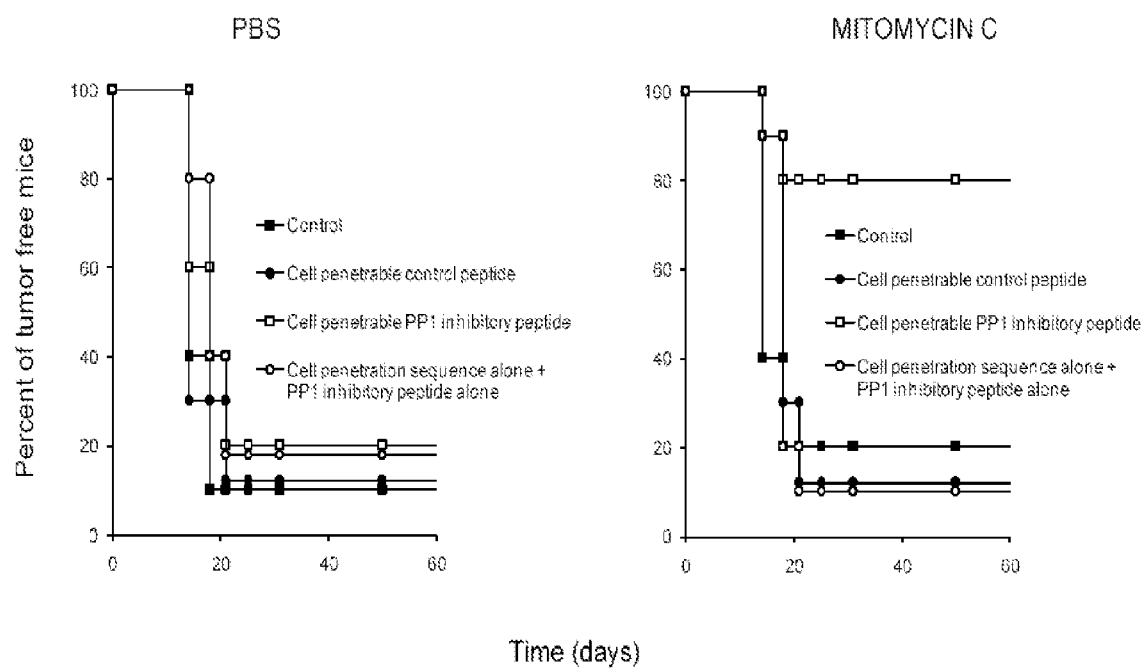

FIG. 12: In vivo synergistic therapeutic effects of the combination of PP1/GADD34 inhibitory peptides together with mitomycin C against established CT26 colon cancer.

CT26 cells were injected se in BALB/c mice. At a size of 20 mm$^2$, the palpable tumors were directly inoculated in situ with 10 micrograms of either of the three following peptides (see below) alone or together with a systemic treatment with mitomycin C (as described in Obeid et al. Nat Med 2007) or PBS.

1. Cell-penetrable PP1 inhibitory peptide VKKK-KIKREIKI-LKARKVRFSEKV (SEQ ID NO: 4)
2. Cell-penetrable control peptide VKKKKIKREIKI-LKARAVRFSEKV (SEQ ID NO: 18)
3. Cell penetration sequence VKKKKIKREIKI (SEQ ID NO: 3) alone admixed together with PP1-inhibitory peptide LKARKVRFSEKV (SEQ ID NO: 2) alone.

The tumor sizes were monitored twice a week and a survival curve is shown for a representative experiment (out of two yielding similar results). 5 animals/group were included in this experiment.

The inhibition of PP1/GADD34 (which induces ecto-CRT) synergizes with the cell death inducer mitomycin C which per se, cannot promote CRT exposure on tumor cell surface (not shown here). The relevant peptide has to be fused with a cell penetrable peptide to enter the cytosol.

Experimental Part
Materials and Methods
Cell Lines and Cell Death Induction.

CT26 cells were cultured at 37° C. under 5% CO2 in RPMI 1640 medium supplemented with 10% FCS, penicillin, streptomycin, 1 mM pyruvate and 10 mM HEPES in the presence of doxorubicin (DX; 24 h, 25 µM), mitoxantrone (Mitox; 24 h, 1 µM, Sigma), idarubicin (24 h, 1 µM, Aventis, France), mitomycin C (30 µM, 48 h; Sanofi-Synthelabo, France), and/ or zVAD-fmk (50 µM, 24 h; Bachem), tunicamycin (24 h, 65 µM), thapsigargin (24 h, 30 µM), brefeldin A (24 h, 50 µM, Sigma), etoposide (48 h, 25 µM, Tava classics), MG132 (48 h, 10 µM), ALLN (48 h, µM), betulinic acid (24 h, 10 µM), Hoechst 33343 (24 h, 0.2 µM), camptothecine (24 h, 15 µM), lactacystin (48 h, 60 µM), BAY 11-8072 (24 h, 30 µM), staurosporine (24 h, 1.5 µM), bafilomycin A1 (48 h, 300 nM), arsenic trioxide (24 h, 30 µM), C2-ceramide (C2-C; 24 h, 60 µM), calyculin A (48 h, 30 nM), or tautomycin (48 h, nM, Sigma) and/or salubrinal (48 h, µM, Calbiochem).

Cell Death Assays.

Cells were trypsinized and subjected to cytofluorometric analysis with a FACS Vantage after staining with 4,6-diamino-2-phenylindole (DAPI, 2.5 mM, 10 min, Molecular Probes) for determination of cell viability, and Annexin V conjugated with fluorescein isothiocyanate (Bender Medsystems) for the assessment of phosphatidylserine exposure (Zamzami, N. & Kroemer, G. *Methods Mol. Biol.* 282, 103-16 (2004).

SiRNAs and Manipulation of Surface CRT.

siRNA heteroduplexes specific for CRT (sense strand: 5'-rCrCrGrCUrGrGrGUrCrGrArAUrCrRrArATT-3'—SEQ ID NO: 11), GADD34 (5'-rCrArGrGrArGrCrArGrAUrCrAr-GrAUrArGrATT-3'—SEQ ID NO: 12), PPICalpha (5'-rGr-CUrGrGrCrCUrAUrArArGrAUrCrArGrATT-3'—SEQ ID NO: 13) or an unrelated control (5'-rGrCrCrGrGUrAUrGr-CrCrGrGUUrArArGUTT-3'—SEQ ID NO: 14) were designed in our laboratory and synthesized by Sigma-Proligo. CT26 cells were transfected by siRNAs at a final concentration of 100 nM using HiPerFect (Qiagen). Thirty six hours post-transfection CT26 cells were assessed for total CRT content by immunoblotting. To restore CRT expression, cells were exposed to rCRT, produced as described (Culina, S., Lauvau, G., Gubler, B. & van Endert, P. M. Calreticulin promotes folding of functional human leukocyte antigen class I molecules in vitro. *J Biol Chem* 279, 54210-5 (2004), at 3 µg/10$^6$ cells in PBC on ice for 30 min, followed by three washes.

Fluorescence Detection of Cell Surface CRT.

CT26 cells (on a glass slide or in 12-well plates) were first washed with FACS buffer (1×PBS, 5% fetus bovine serum, and 0.1% sodium azide) and then incubated with rabbit anti-mouse CRT antibody (1:100, Stressgen) in FACS buffer at 4° C. for 30 min. Cells reacted with anti-rabbit IgG (H+L) Alexa fluor 488-conjugates (1:500) in FACS buffer at 4° C. for 30 min. After washing three times with FACS buffer, surface CRT was detected by cytofluorometric analysis on a FACS Vantage. In some experiments, cells were fixed with 4% paraformaldehyde, counterstained with Hoechst (2 µM; Sigma), followed by fluorescence microscopic assessment with a Leica IRE2 microscope equipped with a DC300F camera.

Immunoblot Analyses.

Cells were washed with cold PBS at 4° C. and lysed in a buffer containing 50 mM Tris HCl pH 6.8, 10% glycerol and 2% SDS. Primary antibodies detecting CRT (dilution 1/2000, Stressgen), CD47 (dilution 1/500, BD Biosciences), EIF2alpha, EIF2alpha-P and PP1c∝ (dilution 1/2000, Cell Signaling Technology), and GADD34 (dilution 1/2000, Abcam), were revealed with the appropriate horseradish peroxidase-labeled secondary antibody (Southern Biotechnologies Associates) and detected by ECL (Pierce). Anti-actin or anti-GAPDH (Chemicon) was used to control equal loading.

Anti-Tumour Vaccination and Treatment of Established Tumours.

All animals were maintained in specific pathogen-free conditions and all experiments followed the FELASA guidelines.

$3 \times 10^6$ treated CT26 cells were inoculated s.c. in 200 ml of PBS into BALB/c six-week-old female mice (Charles River, France), into the lower flank, while $5 \times 10^5$ untreated control cells were inoculated into the contralateral flank. For the tumourigenicity assay, $3 \times 10^6$ treated or untreated CT26 cells were injected s.c. into nu/nu mice (IGR animal facility). To assess the specificity of the immune response against CT26, we injected either $5 \times 10^5$ or $5 \times 10^6$ of CT26 (for the mice immunized in a standard protocol or vaccination protocol, respectively). Tumours were evaluated weekly, using a caliper. In a series of experiments, BALB/c (wild type or nu/nu) carrying palpable CT26 tumours (implanted 14 days before for wild type or 7 days before for nu/nu mice by injection of 106 tumour cells) received a single intratumoural injection of 100 µM PBS containing the same concentration of anti-cancer agents and PP1/GADD34 inhibitors as those used in vitro, as well as rCRT (15 µg). For the assessment of local immune response, $3 \times 10^5$ cells were injected in 50 µl into the footpad of mice. Five days later, mice were sacrificed and the draining lymph nodes were harvested. $1 \times 10^5$ lymph node cells were cultured for 4 days alone or with $1 \times 10^4$ CT26 cells killed by a freeze-thaw cycle in 200 µl in round-bottom 96-well plates. IFN-γ was determined by ELISA (BD Pharmingen).

Generation of BMDCs

BM cells were flushed from the tibias and femurs of BALB/c mice with culture medium composed of RPMI 1640 medium (Invitrogen Life Technologies) supplemented with 10% heat-inactivated FBS (Invitrogen), sodium pyruvate, 50 µM 2-ME (Sigma), 10 mM HEPES (pH 7.4), and penicillin/streptomycin (Invitrogen). After one centrifugation, BM cells were resuspended in Tris-ammonium chloride for 2 min to lyse RBC. After one more centrifugation, BM cells ($1 \times 10^6$ cells/ml) were cultured in medium supplemented with 100 ng/ml recombinant mouse FLT3 ligand (R&D systems) in 6-well plates (Costar Corning). After 7 days, the non-adherent and loosely adherent cells were harvested with Versene, washed and transferred in 12-well plates ($1.5 \times 10^6$ cells/plate) for cocultures with tumour cells.

Phagocytosis Assays.

In 12-well plates, $25 \times 10^6$ adherent CT26 cells were labelled with Celltracker Green (Calbiochem) and then incubated with drugs. In some experiments viable CT26 were coated with 2 µg/$10^6$ cells of chicken anti-CRT antibody (ABR affinity bioreagents) or an isotype control for 30 min prior to washing and feeding to dendritic cells Cs. Alternatively CT26 cells were coated with 2 µg/$10^6$ cells of rCRT on ice for 30 min and washed twice prior to addition to dendritic cells. Cells were then harvested, washed three times with medium supplemented with FBS and cocultured with immature DC for 2 hours at a ratio of 1:1 and 1:5. At the end of the incubation, cells were harvested with versene, pooled with non-adherent cells present in the supernatant, washed and stained with CD11c-FITC antibody. Phagocytosis was assessed by FACS analysis of double positive cells. Phagocytic indexes refer to the ratio between values obtained at 4° C. and values obtained at 37° C. of co-incubation between DC and tumour cells.

Statistical Analyses.

Data are presented as arithmetic means±standard deviation (SD) or percentages. All statistical analyses were performed using JMP software (SAS Institute Inc.). The Student's t-test was used to compare continuous variables (comparison of tumour growth), the Chi square test for non-parametrical variables (comparison of animal cohorts). For all tests, the statistical significance level was set at 0.05.

Biochemical Methods.

The purification of plasma membrane proteins, mass spectroscopy and the generation of cytoplasts are detailed below.

Biotinylation of CT26 Cell Surface Proteins.

Biotinylation and recovery of cell surface proteins were performed with a method adapted from Gottardi et al. (Gottardi, C. J., Dunbar, L. A. & Caplan, M. J. Biotinylation and assessment of membrane polarity: caveats and methodological concerns. *Am J Physiol* 268, F285-95 (1995)) and Hanwell et al. (Hanwell, D., Ishikawa, T., Saleki, R. & Rotin, D. Trafficking and cell surface stability of the epithelial Na+ channel expressed in epithelial Madin-Darby canine kidney cells. *J Biol Chem* 277, 9772-9 (2002)). Briefly, $20 \times 10^6$ CT26 cells grown on 75 cm² flask were placed on ice and washed three times with ice-cold PBS-$Ca^{2+}$—$Mg^{2+}$ (PBS with 0.1 mM CaCl2 and 1 mM MgCl2). Membrane proteins were then biotinylated by a 30-min incubation at 4° C. with NHS-SS-biotin 1.25 mg/ml (Pierce) freshly diluted into biotinylation buffer (10 mM triethanolamine, 2 mM CaCl2, 150 mM NaCl, pH 7.5) with gentle agitation. CT26 cells were rinsed with PBS-$Ca^{2+}$—$Mg^{2+}$+glycine (100 mM) and washed in this buffer for 20 min at 4° C. to quench unreacted biotin. The cells were then rinsed twice with PBS-$Ca^{2+}$—$Mg^{2+}$, scraped in cold PBS, and pelleted at 2,000 rpm at 4° C. The pellets were solubilized for 45 min in 500 µl of lysis buffer (1% Triton X-100, 150 mM NaCl, 5 mM EDTA, 50 mM Tris, pH 7.5) containing protease inhibitors. The lysates were clarified by centrifugation at 14,000×g for 10 min at 4° C., and the supernatants were incubated overnight with packed streptavidin-agarose beads to recover biotinylated proteins. The beads were then pelleted by centrifugation, and aliquots of supernatants were taken to represent the unbound, intracellular pool of proteins. Biotinylated proteins were eluted from the beads by heating to 100° C. for 5 min in SDS-PAGE sample buffer before loading onto a 10% SDS-PAGE gel as described above. To ensure the absence of leakage of biotin into the cells, we systematically verified the absence of the intracellular protein actin and GAPDH in biotinylated extracts.

2D Gel Electrophoresis Analysis and Protein Identification by Mass Spectrometry.

Purified proteins were precipitated using the Ettan 2-D clean up kit (GE Healthcare) were subsequently resuspended in urea buffer (7M urea, 2M thiourea, 2% Chaps, 1% Sulfobetaine SB3-10, 1% Amidosulfobetaine ASB14, 50 mM DTT). For the first dimension of protein separation, isoelectric focusing (IEF) was performed using 18-cm immobilized nonlinear pH gradient strips (pH 3 to 10; GE Healthcare) on a IPGphor II electrophoresis unit (GE Healthcare). Proteins (100 µg) were loaded by in-gel rehydratation for 9 h, using low voltage (30V) then run using a program in which the voltage was set for 1 h at 100 V, 2 h at 200 V, 1 h at 500 V, 1 h at 1,000 V, 2 hrs, 2 hrs voltage gradient 1,000-8,000V and 4 h at 8,000 V. Prior to the second-dimension electrophoresis, IPG gel strips were equilibrated for 10 min at room temperature in 1% dithiothreitol to reduce the proteins and sulfhydryl groups were subsequently derivatized using 4% iodoacetamide (both solutions were prepared in 50 mM Tris [pH 8.8]-6 M urea-30% glycerol-2% SDS-2% bromophenol blue). Strips were transferred to 1.0-mm-thick 10% (wt/vol) polyacrylamide gels (20 by 20 cm), and the second-dimension gels were run at 50 µA for 6 h. Gels were stained with Sypro Ruby (BioRad) and visualized using a Typhoon 9200 scanner (GE Healthcare). The Investigator HT analyser (Genomic Solutions Inc) was used for matching and analysis of visualized protein spots among differential gels. Background subtraction was used to normalize the intensity value representing the amount of protein per spot.

Differentially expressed spots were excised from the gels with an automatic spot picker (Investigator ProPic, Genomic Solutions Inc.), placed in Eppendorf tubes, and destained by washing for 5 min with 50 µL of 0.1 M NH4HCO3. Then 50 µL of 100% acetonitrile were added incubated for other 5 min. The liquid was discarded, the washing steps were repeated one more time and gel plugs were shrunk by addition of pure acetonitrile. The dried gel pieces were reswollen with 4.0 ng/µL trypsin (Promega, Madison, Wis.) in 50 mM NH4HCO3 and digested overnight at 37° C. Peptides were concentrated with ZipTip®µC18 pipette tips. Co-elution was performed directly onto a MALDI target with 1 µL of alpha-cyano-4-hydroxycinnamic acid matrix (5 µg/mL in 50% acetonitrile, 0.1% TFA). MALDI-MS and MALDI-MS/MS were performed on an Applied Biosystems 4700 Proteomics Analyzer with TOF/TOF ion optics. Spectra were acquired in positive MS reflector mode and calibrated either externally using five peaks of standard (ABI4700 Calibration Mixture) or internally using porcine trypsin autolysis peptide peaks (842.51, 1045.56 and 2211.10 $[M+H]^+$ ions). Mass spectra were obtained from each sample spot by 30 sub-spectra accumulation (each consisting of 50 laser shots) in a 750 to 4000 mass range. Five signal-to-noise best peaks of each spectrum were selected for MS/MS analysis. For MS/MS spectra, the collision energy was 1 keV and the collision gas was air (Medzihradszky, K. F. et al. The characteristics of peptide collision-induced dissociation using a high-performance MALDI-TOF/TOF tandem mass spectrometer. *Anal Chem* 72, 552-8 (2000)).

MS and MS/MS data were interpreted using the GPS Explorer software (Version 2.1, Applied Biosystems) which acts as an interface between the Oracle database containing raw spectra and a local copy of the MASCOT search engine (Version 1.8). Peptide mass fingerprints obtained from MS analysis were used for protein identification in Swiss Prot non-redundant database. All peptide mass values are considered monoisotopic and mass tolerance was set<50 ppm. Trypsin was given as the digestion enzyme, 1 missed cleavage site was allowed, methionine was assumed to be partially oxidized and serine, threonine and tyrosine partially phosphorylated. Mascot (Matrix Science) scores greater than 71 were considered to be significant ($p<0.005$). For MS/MS analysis, all peaks with a signal-to-noise ratio greater than 5 were searched against the Swiss Prot database using the same modifications as the MS database. Fragment tolerance less than 0.3 Da was considered.

Preparation of Cytoplasts.

Trypsinized CT26 cells were enucleated as described in the publication of Andreau, K. et al. Contagious apoptosis facilitated by the HIV-1 envelope. Fusion-induced cell-to-cell transmission of a lethal signal. *J. Cell Sci.* 117, 5643-53 (2004). Briefly, cells were treated in 2 ml of complete RPMI medium containing cytochalasin B (10 µg/ml; Sigma) and DNase I (80 U/ml; Sigma). Cell suspension was adjusted to a final concentration of $5 \times 10^6$/ml and incubated at 37° C. for 45 minutes before being layered onto a previously prepared discontinuous Ficoll (Pharmacia) density gradient (3 ml of 100%, in 1 ml of 90% and 3 ml of 55% Ficoll Paque layer containing 5 µg/ml cytochalasin B and 40 U/ml DNase I; gradients were prepared in ultracentrifuge tubes and pre-equilibrated at 37° C. in a CO2 incubator overnight). Gradients containing cell suspensions were centrifugated in a pre-warmed SW41 Beckman rotor at 25 000 rpm for 20 minutes at 30° C. The cytoplasts-enriched fraction was collected from the interface between 90 and 100% Ficoll layers, washed in complete RPMI medium, and incubated at 37° C. The cells were incubated with MTX, CA, Sal and TA for the period of time indicated in the experiment. Then the cell surface CRT was detected (see materials and methods) and the viability was determined by with propidium iodine staining (2 µg/ml, Sigma) for 5 min followed by cytofluorometric analysis. Alternatively cythoplasts were cocultured with immature DC for 2 hours at a ratio of 1:1 and 1:5. At the end of the incubation, cells were harvested with versene, pooled with non-adherent cells present in the supernatant, washed and stained with CD11c-FITC antibody. Phagocytosis was assessed by FACS analysis of double positive cells.

Different examples are given in order to complete and illustrate the invention of the present application.

EXAMPLE 1

CRT Exposure Defines Immunogenic Cell Death

Dying CT26 tumour cells exposed to a panel of ~20 distinct apoptosis inducers (all of which induced ~70±10% apoptosis, as determined by double staining with the vital dye DAPI and the PS-binding dye Annexin V, FIG. 1A) were injected into one flank of immunocompetent BALB/c mice, followed by rechallenge of the animals with live tumour cells injected into the opposite flank 8 days later. Protection against tumour growth then was interpreted as a sign of anti-tumour vaccination (FIG. 1B) because such protection was not observed in athymic (nu/nu) BALB/c mice (Casares, N. et al. *J. Exp. Med.* 202, 1691-701 (2005). and data not shown). Most apoptosis inducers, including agents that target the endoplasmic reticulum (ER) (thapsigargin, tunicamycin, brefeldin), mitochondria (arsenite, betulinic acid, C2 ceramide) or DNA (Hoechst 33342, camptothecin, etoposide, mitomycin C), failed to induce immunogenic apoptosis, while anthracyclins (doxorubicin, idarubicin, mitoxantrone) elicited immunogenic cell death (FIGS. 1B,C). To identify changes in the plasma membrane proteome, we affinity-purified biotinylated surface proteins from cells that were either untreated or short-term (4 h) treated with doxorubicin or doxorubicin plus Z-VAD-fmk, a pan-caspase inhibitor that reduces the immunogenicity of doxorubicin-elicited cell death (Casares, N. et al. *J. Exp. Med.* 202, 1691-701 (2005). and FIG. 1B). Comparison of 2D electrophoreses (FIG. 2A), followed by mass spectroscopic analyses, led to the identification of CRT (FIG. 2B) as a protein that was strongly (by a factor of 6) induced by doxorubicin, but less so (by a factor of 1.8) by doxorubicin combined with Z-VAD-fmk. Another protein whose surface exposure was specifically induced by doxorubicin were identified as ERP57 (FIG. 2A), a CRT-interacting chaperone (Bedard, K., Szabo, E., Michalak, M. & Opas, M. *Int Rev Cytol* 245, 91-121 (2005). Immunoblot analyses of 2D gels (not shown) and conventional electrophoreses of purified plasma membrane surface proteins (FIG. 2C) confirmed the surface exposure of CRT after treatment with anthracyclins. This CRT surface exposure was also detectable by immunofluorescence staining of anthracyclin-treated live cells (FIG. 2D) and was not accompanied by a general increase in the abundance of intracellular CRT (FIGS. 2C,D). The induction of CRT exposure by anthracyclins was a rapid process, detectable as soon as 1 h after treatment (FIG. 1S A,B), and hence preceded the apoptosis-associated phosphatidylserine (PS) exposure (FIG. 1S C,D). CRT exposure did not correlate with alterations in CD47 expression (FIG. 2C). Of note, there was a strong positive linear correlation ($p<0.001$) between the appearance of CRT at the cell surface (measured at 4 h) and the immunogenicity elicited by the panel of 20 distinct apoptosis inducers (FIG. 2E).

EXAMPLE 2

Requirement of CRT for Dc-Mediated Recognition of Dying Tumour Cells

In view of the established role of CRT as an "eat me" signal (Gardai, S. J. et al. *Cell* 123, 321-34 (2005); Ogden, C. A. et al. *J Exp Med* 194, 781-95 (2001)), we decided to further investigate the possible implication of CRT in the phagocytosis of anthracyclin-treated tumour cells by DC, a cell type that is stringently required for mounting an immune response against apoptotic tumour cells (Steinman, R. M., Turley, S., Mellman, I. & Inaba, K. *J Exp Med.* 191, 411-6 (2000); Casares, N. et al. *J. Exp. Med.* 202, 1691-701 (2005)). Anthracyclin-treated tumour cells acquired the property to be phagocytosed by DC quickly, well before the manifestation of apoptotic changes, within a few hours after treatment with doxorubicin or mitoxantrone (FIG. 3A, FIG. 2S A), correlating with the rapid induction of CRT (FIG. 3B, FIGS. 1S A, B) and the acquisition of immunogenicity (FIG. 2S B). The presence of CRT on the surface of tumour cells treated with a panel of distinct cell death inducers strongly correlated with their DC-mediated phagocytosis, suggesting that CRT is important in mediating the uptake of tumour cells by DC (FIG. 3B). Accordingly, blockade of the CRT present on the surface of mitoxantrone-treated cancer cells by means of a specific antibody from avian origin (which cannot interact with mouse Fc receptors) inhibited their phagocytosis by DC (FIG. 3C). Similarly, knockdown of CRT with a specific siRNA (FIGS. 3D, E) suppressed the phagocytosis of anthracyclin-treated tumour cells (FIG. 2F). Addition of recombinant CRT protein (rCRT), which binds to the surface of the cells, could reverse the defect induced by the CRT-specific siRNA, both at the level of CRT expression (FIG. 3E) and phagocytosis by DC (FIG. 3F). Of note, rCRT alone could not promote DC maturation ex vivo over a large range of concentrations. Hence, surface CRT elicits phagocytosis by DC.

EXAMPLE 3

Requirement of CRT for Immunogenicity of Dying Tumour Cells

The knock-down of CRT compromised the immunogenicity of mitoxantrone-treated CT26 cells, and this defect was restored when rCRT was used to complement the CRT defect induced by the CRT-specific siRNA. This result was obtained in two distinct experimental systems, namely (i) when CT26 tumour cells were injected into the flank of Balb/c mice (or MCA205 cells were injected into C57B1/6 mice, not shown) to assess the efficacy of anti-tumour vaccination (FIG. 4A) and (ii) when the tumour cells were injected into the foot pad to measure interferon-γ production by T cells from the popliteal lymph node (FIG. 4B). In this latter system, absorption of rCRT to the plasma membrane surface greatly enhanced the immunogenicity of cells that usually fail to induce an immune response such as mitomycin-treated cells (FIG. 4C). Similarly, etoposide-treated cells coated with rCRT elicited a vigorous anti-tumour immune response in vivo, in conditions in which sham-coated cells treated with etoposide were poorly immunogenic (FIG. 4E). However, absorption of rCRT to the cell surface without prior treatment with cell death inducers failed to elicit an anti-cancer immune response and live rCRT-pretreated cells inoculated into mice formed tumours, both in immunocompetent (FIG. 4E) and immunodeficient mice (not shown). Thus, CRT critically determines the immunogenicity of cell death in vivo but does not determine cell death as such.

EXAMPLE 4

Inhibitors of PP1/GADD34 Induce CRT Exposure and Induce Immunogenicity

Since anthracyclin-induced CRT exposure was a rather rapid process (within 1 h, FIGS. 1SA, 1SB), we suspected that anthracyclins might exert effects that are not mediated by genotoxic stress. In response to mitoxantrone, enucleated cells (cytoplasts) readily (within 1 h) exposed CRT (FIG. 5A) and became preys of DC (not shown) as efficiently as intact cells (FIG. 3A), indicating the existence of a cytoplasmic (non-nuclear) anthracyclin target. Anthracyclins failed to induce immediate mitochondrial stress (not shown), yet caused the rapid phosphorylation of eIF2alpha (FIG. 5B), a protein that is typically hyperphosphorylated in ER stress due to the activation of stress kinases (Zhang, K. & Kaufman, R. J. *J Biol Chem* 279, 25935-8 (2004). Knock-down of the four kinases known to phosphorylate eIF2alpha (GCN2, HRI, PERK, PKR) failed to inhibit the anthracyclin-stimulated CRT exposure (not shown). In contrast, knock-down of either GADD34 or the catalytic subunit of protein phosphatase 1 (PP1) (FIG. 5C), which together form the PP1/GADD34 complex involved in the dephosphorylation of eIF2alpha was sufficient to induce CRT exposure (FIG. 5D and not shown). The CRT exposure triggered by PP1 or GADD34 depletion was not further enhanced by mitoxantrone (FIG. 5D), suggesting that PP1/GADD34 and anthracyclins act on the same pathway to elicit CRT translocation to the cell surface. CRT exposure was efficiently induced by chemical PP1/GADD34 inhibitors, namely tautomycin, calyculin A (which both inhibit the catalytic subunit of PP1) (Gupta, V., Ogawa, A. K., Du, X., Houk, K. N. & Armstrong, R. W. *J Med Chem* 40, 3199-206 (1997)), as well as by salubrinal (which inhibits the PP1/GADD34 complex) (Boyce, M. et al. *Science* 307, 935-9 (2005)) (FIG. 5E). All these PP1/GADD34 inhibitors induced CRT exposure with a similar rapid kinetics as did anthracyclins, both in cells (FIG. 5E) and in cytoplasts. Mitoxantrone and salubrinal induced CRT exposure on a panel of tumour cell lines from murine (MCA205, B16F10, J558) or human origin (HeLa, A549, HCT116). CRT exposure induced by anthracyclins and PP1/GADD34 inhibitors was not affected by inhibitors of transcription, translation or microtubuli, yet was abolished by latrunculin A, an inhibitor of the actin cytoskeleton and exocytosis (FIG. 3S). Inhibition of the PP1/GADD34 complex with salubrinal, calyculin A or tautomycin was not sufficient to induce immunogenic cell death (FIGS. 5F, G) (and the cells, which did not die, formed lethal tumours when injected into animals). However, these inhibitors greatly enhanced However, these inhibitors greatly enhanced CRT exposure (FIG. 5F) and the immunogenic potential of cells succumbing to etoposide (FIG. 5G) or mitomycin C (not shown) and this immunostimulatory effect was abrogated by knocking down CRT (FIG. 5G). Altogether, these results demonstrate that PP1/GADD34 inhibition induces CRT exposure, which in turn can stimulate the anti-tumour immune response.

EXAMPLE 5

Immunogenic Chemotherapy by In Vivo Application of CRT or PP1/GADD34 Inhibitors A single intratumoural injection of mitoxantrone into established 14-day-old CT26 tumours was able to cause their permanent regression in some but not all cases, if the tumours were established in immunocompetent BALB/c mice (FIG. 6A). However, there was no cure by mitoxantrone if the tumours were carried by immunodeficient nu/nu mice (FIG. 6B). The intratumoural injection of rCRT, salubrinal, tautomycin, etoposide or mitomycin C had no major therapeutic effect, neither in immunocompetent nor in nu/nu mice. However, the combination of a cell death inducer (etoposide or mitomycin C) plus rCRT was able to cause tumour regression, in immunocompetent (but not in immunodeficient) animals. To obtain a therapeutic effect, rCRT had to be injected into the tumour. rCRT injected into a distant site did not ameliorate the antitumoural effects of intratumorally injected etoposide (FIG. 6C). Similarly, etoposide or mitomycin C could be combined with drugs that induce CRT exposure (salubrinal or tautomycin), leading to stable disease or complete tumour regression in immunocompetent (but not in athymic) hosts (FIGS. 6A, B). Live CT26 cells failed to grow in animals that had been cured from CT26 tumours, indicating the establishment of a permanent anti-tumour immune response. Similar results were obtained when established MCA205 sarcomas (in C57Bl/6 mice) or PRO colon carcinomas (in BDIX rats) were treated by local injections of weakly immunogenic cell death inducers plus rCRT or PP1/GADD34 inhibitors (not shown). These results delineate a strategy of immunogenic chemotherapy for the cure of established cancer.

The invention claimed is:

1. A method for treating colon cancer in a mammal in need of treatment comprising the administration of a protein phosphatase inhibitor of the PP1/GADD34 complex, in combination with a product for the treatment of colon cancer wherein the protein phosphatase inhibitor is a fragment of GADD34 consisting of VKKKKIKREIKI-LKARKVRFSEKV (SEQ ID NO: 4).

2. The method according to claim 1, wherein said product is selected from a chemotherapeutic agent, a hormone, an immunotherapeutic agent, a specific kinase inhibitor, an antiangiogenic agent or a monoclonal antibody.

3. The method according to claim 2, wherein said product is a chemotherapeutic agent.

4. The method according to claim 2, wherein said product is selected from an anthracyclin or a tyrosine kinase inhibitor.

5. The method according to claim 4, wherein said anthracyclin is selected from doxorubicin, daunorubicin, idarubicin or mitoxantrone.

6. The method according to claim 2, wherein said product is an immunotherapeutic agent.

7. The method according to claim 2, wherein said product is a specific kinase inhibitor.

8. The method according to claim 2, wherein said product is an antiangiogenic agent.

9. The method according to claim 2, wherein said product is a monoclonal antibody.

10. The method according to claim 2, wherein said product is a hormone.

* * * * *

UNITED STATES PATENT AND TRADEMARK OFFICE
CERTIFICATE OF CORRECTION

PATENT NO. : 8,129,340 B2
APPLICATION NO. : 12/438833
DATED : March 6, 2012
INVENTOR(S) : Guido Kroemer et al.

It is certified that error appears in the above-identified patent and that said Letters Patent is hereby corrected as shown below:

Title page,
(73) Assignees, "Institut Gustave Roussy, Villejuif Cedex (FR); Institut National de la Sante et de la Recherche Medicale (Inserm), Paris Cedex (FR)" should read --Institut Gustave Roussy, Villejuif Cedex (FR); INSERM (Institut National de la Sante et de la Recherche Medicale), Paris Cedex (FR)--.

Column 1,
Line 41, "type of" should read --types of--.

Column 4,
Line 24, "surface o" should read --surface of--.

Column 6,
Line 24, "ERP57" should read --ERp57--.
Line 30, "ERP57" should read --ERp57--.
Line 64, "Erp57" should read --ERp57--.

Column 7,
Line 23, "ecto-Erp57" should read --ecto-ERp57--.
Line 62, "DC few" should read --DC a few--.

Column 12,
Line 36, "Erp57" should read --ERp57--.
Line 37, "Erp57" should read --ERp57--.
Line 41, "Erp57" should read --ERp57--.
Line 49, "Erp57" should read --ERp57--.

Column 13,
Line 28, "diluant" should read --diluent--.

Signed and Sealed this
Twelfth Day of June, 2012

David J. Kappos
*Director of the United States Patent and Trademark Office*

Column 15,
Line 21, "anti-Erp57" should read --anti-ERp57--.
Line 23, "Erp57" should read --ERp57--.

Column 21,
Line 8, "bean quantitative" should read --be a quantitative--.

Column 22,
Line 33, "ERP57" should read --ERp57--.

Column 24,
Line 31, "from Abeam" should read --from Abcam--.
Line 40, "Erp57" should read --ERp57--.
Line 52, "Erp57" should read --ERp57--.
Line 57, "Erp57" should read --ERp57--.

Column 25,
Line 32, "Erp57" should read --ERp57--.
Line 37, "se in" should read --sc in--.

Column 27,
Line 14, "106 tumour" should read --$10^6$ tumour--.

Column 30,
Line 48, "were identified as ERP57" should read --was identified as ERp57--.

Column 32,
Lines 51-52, "animals). However, these inhibitors greatly enhanced However," should read --animals). However,--.